(12) United States Patent
Gulati

(10) Patent No.: US 10,561,704 B2
(45) Date of Patent: Feb. 18, 2020

(54) COMPOSITIONS AND METHODS FOR TREATING NEUROPSYCHIATRIC DISORDERS USING AN ENDOTHELIN-B RECEPTOR AGONIST

(71) Applicant: MIDWESTERN UNIVERSITY, Downers Grove, IL (US)

(72) Inventor: Anil Gulati, Naperville, IL (US)

(73) Assignee: MIDWESTERN UNIVERSITY, Downers Grove, IL (US)

( * ) Notice: Subject to any disclaimer, the term of this patent is extended or adjusted under 35 U.S.C. 154(b) by 0 days.

(21) Appl. No.: 14/903,574

(22) PCT Filed: Jul. 8, 2014

(86) PCT No.: PCT/US2014/045748
§ 371 (c)(1),
(2) Date: Jan. 7, 2016

(87) PCT Pub. No.: WO2015/006324
PCT Pub. Date: Jan. 15, 2015

(65) Prior Publication Data
US 2016/0151450 A1    Jun. 2, 2016

Related U.S. Application Data

(60) Provisional application No. 61/902,935, filed on Nov. 12, 2013, provisional application No. 61/843,702, filed on Jul. 8, 2013.

(51) Int. Cl.
| | | |
|---|---|---|
| *A61K 38/00* | (2006.01) | |
| *A61K 38/16* | (2006.01) | |
| *A61K 38/10* | (2006.01) | |
| *A61K 45/06* | (2006.01) | |

(52) U.S. Cl.
CPC ............. *A61K 38/10* (2013.01); *A61K 45/06* (2013.01)

(58) Field of Classification Search
None
See application file for complete search history.

(56) References Cited

U.S. PATENT DOCUMENTS

| | | |
|---|---|---|
| 3,954,987 A | 5/1976 | Simpson |
| 3,983,121 A | 9/1976 | Murthi et al. |
| 4,088,659 A | 5/1978 | Bhati et al. |
| 4,761,417 A | 8/1988 | Maroko |
| 5,055,470 A | 10/1991 | Boissard et al. |
| 5,922,681 A | 7/1999 | Doherty et al. |
| 6,372,226 B2 | 4/2002 | Aoki et al. |
| 6,545,048 B1 | 4/2003 | Patterson et al. |
| 7,030,082 B2 | 4/2006 | Soltero et al. |
| 8,623,823 B2 * | 1/2014 | Gulati ............... A61K 38/2285 514/13.5 |
| 9,493,524 B2 * | 11/2016 | Gulati ............... A61K 38/2285 |
| 2002/0082285 A1 | 6/2002 | Lebwohl |
| 2003/0100507 A1 | 5/2003 | Gulati |
| 2003/0104976 A1 | 6/2003 | Davar et al. |
| 2003/0232787 A1 | 12/2003 | Dooley |
| 2003/0236235 A1 | 12/2003 | Gulati |
| 2004/0063719 A1 | 4/2004 | Adams et al. |
| 2004/0138121 A1 | 7/2004 | Gulati |
| 2004/0176274 A1 | 9/2004 | Davar et al. |
| 2010/0004166 A1 | 1/2010 | Pittner et al. |
| 2012/0093798 A1 | 4/2012 | Gulati |

FOREIGN PATENT DOCUMENTS

| | | |
|---|---|---|
| EP | 0410114 A2 | 1/1991 |
| JP | 2010-536868 A | 12/2010 |
| WO | WO-2002/43654 A2 | 6/2002 |
| WO | WO-03/009805 A2 | 2/2003 |
| WO | WO-2004/037235 A2 | 5/2004 |
| WO | WO-2004/045592 A2 | 6/2004 |
| WO | WO-2008/043102 A2 | 4/2008 |
| WO | WO-2009/026282 A2 | 2/2009 |
| WO | WO-2009/026828 A1 | 3/2009 |
| WO | WO-2012/138043 A2 | 10/2012 |

OTHER PUBLICATIONS

Rebello, et al. "Elevated levels of endothelin-1 following unilateral cerebral-ischemia in rats," *Faseb Journal* 9:A937-A (1995).
Schiffrin, et al. "Clinical significance of endothelin in cardiovascular disease," Curr Opin Cardiol 12:354-367 (1997).
Ahmed, et al. "Curcuminoids Enhance Memory in an Amyloid-Infused Rat Model of Alzheimer's Disease," Neuroscience 169:1296-1306 (2010).
Andres et al. "Human neural stem cells enhance structural plasticity and axonal transport in the ischaemic brain," Brain 134:1777-1789 (2011).
Asano, et al. "Endothelin: a potential modulator of cerebral vasospasm," European journal of pharmacology 190:365-372 (1990).
Bacigaluppi et al., "Delayed post-ischaemic neuroprotection following systemic neural stem cell transplantation involves multiple mechanisms," Brain : a journal of neurology 132:2239-2251 (2009).
Baquer, et al. "A metabolic and functional overview of brain aging linked to neurological disorders," Biogerontology 10:377-413 (2009).

(Continued)

*Primary Examiner* — Olga N Chernyshev
(74) *Attorney, Agent, or Firm* — Marshall, Gerstein & Borun LLP

(57) ABSTRACT

The present invention relates to compositions and methods for treating neuropsychiatric disorders in vertebrates and humans. More specifically, the present invention provides for use of IRL-1620, an endothelin-B receptor agonist, in appropriate doses to be a neuroprotective and a neuroregenerative agent. Accordingly, in one aspect the disclosure provides a method of treating a neuropsychiatric disorder comprising administering to a patient in need thereof a therapeutically effective amount of an endothelin-B receptor agonist to treat the neuropsychiatric disorder. In some embodiments, the endothelin-B receptor agonist is co-administered with an additional agent to treat the neuropsychiatric disorder. In some embodiments, the additional agent is selected from the group consisting of an antidepressant, an anti-inflammatory agent, a CNS stimulant, a neuroleptic, and an anti-proliferative agent.

8 Claims, 30 Drawing Sheets

Specification includes a Sequence Listing.

(56) References Cited

OTHER PUBLICATIONS

Barone, et al. "Selective antagonism of endothelin-A-receptors improves outcome in both head trauma and focal stroke in rat," Journal of cardiovascular pharmacology 36:S357-361 (2000).

Barone, et al. "The endothelin receptor antagonist SB 217242 reduces cerebral focal ischemic brain injury," Journal of cardiovascular pharmacology 26 Suppl 3:S404-407 (1995).

Bath, et al. "ABC of arterial and venous disease, Acute stroke," BMJ 320:920-923 (2000).

Bell, et al. "Neurovascular mechanisms and blood-brain barrier disorder in Alzheimer's disease," Acta neuropathologica 118:103-113 (2009).

Bredesen, et al. "Cell death in the nervous system," Nature 443:796-802 (2006).

Breier, et al. "The role of vascular endothelial growth factor in blood vessel formation," Trends in cell biology 6:454-456 (1996).

Briyal, et al. "Endothelin-A receptor antagonist BQ123 potentiates acetaminophen induced hypothermia and reduces infarction following focal cerebral ischemia in rats," European journal of pharmacology 644:73-79 (2010).

Briyal, et al. "Effect of combination of endothelin receptor antagonist (TAK-044) and aspirin in middle cerebral artery occlusion model of acute ischemic stroke in rats," Methods Find Exp Clin Pharmacol 29:257-263 (2007).

Briyal, et al. "Repeated administration of centhaquin to pregnant rats did not affect postnatal development and expression of endothelin receptors in the brain, heart or kidney of pups," Arzneimittel-Forschung 62:670-676 (2012b).

Briyal, et al. "Endothelin-A receptor antagonists prevent amyloid-beta-induced increase in ETA receptor expression, oxidative stress, and cognitive impairment," Journal of Alzheimer's disease : JAD 23:491-503 (2011).

Briyal, et al. "Repeated administration of exendin-4 reduces focal cerebral ischemia-induced infarction in rats," Brain research 1427:23-34 (2012a).

Carmichael, "Cellular and molecular mechanisms of neural repair after stroke: making waves," Annals of neurology 59:735-742 (2006).

Casadesus, et al. "Indices of metabolic dysfunction and oxidative stress," Neurochemical research 32:717-722 (2007).

Chen, et al. "Niaspan increases angiogenesis and improves functional recovery after stroke," Annals of neurology 62:49-58 (2007).

Chuquet, et al. "Selective blockade of endothelin-B receptors exacerbates ischemic brain damage in the rat," Stroke; a journal of cerebral circulation 33:3019-3025 (2002).

Cirrito, et al. "Synaptic activity regulates interstitial fluid amyloid-beta levels in vivo," Neuron 48:913-922 (2005).

Cutler, et al. "Involvement of oxidative stress-induced abnormalities in ceramide and cholesterol metabolism in brain aging and Alzheimer's disease," Proceedings of the National Academy of Sciences of the United States of America 101:2070-2075 (2004).

de la Torre, "Impaired brain microcirculation may trigger Alzheimer's disease," Neuroscience and biobehavioral reviews 18:397-401 (1994).

de la Torre, et al. "Hippocampal nitric oxide upregulation precedes memory loss and A beta 1-40 accumulation after chronic brain hypoperfusion in rats," Neurological research 25:635-641 (2003).

Deb, et al. "Pathophysiologic mechanisms of acute ischemic stroke: An overview with emphasis on therapeutic significance beyond thrombolysis," Pathophysiology 17:197-218 (2010).

Dembowski, et al. "Phenotype, intestinal morphology, and survival of homozygous and heterozygous endothelin B receptor-deficient (spotting lethal) rats," *J Pediatr Surg* 35:480-488 (2000).

Dimyan, et al. "Neuroplasticity in the context of motor rehabilitation after stroke," Nature reviews Neurology 7:76-85 (2011).

Ding, et al. "Magnetic resonance imaging investigation of axonal remodeling and angiogenesis after embolic stroke in sildenafil-treated rats," Journal of Cerebral Blood Flow and Metabolism, 28:1440-1448 (2008).

Donnan, et al. "Stroke," Lancet 371:1612-1623 (2008).

Ehrenreich, et al. "Endothelin b receptor deficiency is associated with an increased rate of neuronal apoptosis in the dentate gyrus," Neuroscience 95:993-1001 (2000).

Ehrenreich, "The astrocytic endothelin system: toward solving a mystery focus on distinct pharmacological properties of ET-1 and ET-3 on astroglial gap junctions and Ca(2+) signaling" The American journal of physiology 277:C614-615 (1999).

Ehrenreich, et al. "Endothelin B receptor-deficient rats as a subtraction model to study the cerebral endothelin system," Neuroscience 91:1067-1075 (1999).

Ellman, "Tissue sulfhydryl groups," Archives of biochemistry and biophysics 82:70-77 (1959).

Ethell, "An amyloid-notch hypothesis for Alzheimer's disease," The Neuroscientist 16:614-617 (2010).

Feigin, et al. "Worldwide stroke incidence and early case fatality reported in 56 population-based studies: a systematic review," Lancet Neurol 8:355-369 (2009).

Fisher, et al., The International Agenda for Stroke, in *1st Global Conference on Healthy Lifestyles and Noncommunicable Diseases Control* (Association AH ed), American Heart Association, Moscow (2011).

Font, et al., "Angiogenesis, neurogenesis and neuroplasticity in ischemic stroke," *Current cardiology reviews* 6:238-244 (2010).

Gil-Mohapel, et al., "Hippocampal cell loss and neurogenesis after fetal alcohol exposure: insights from different rodent models," *Brain Res Rev* 64:283-303 (2010).

Goligorsky, et al. "Co-operation between endothelin and nitric oxide in promoting endothelial cell migration and angiogenesis," Clinical and experimental pharmacology & physiology 26:269-271 (1999).

Gora-Kupilas, et al., "The neuroprotective function of vascular endothelial growth factor (VEGF)," *Folia neuropathologica / Association of Polish Neuropathologists and Medical Research Centre, Polish Academy of Sciences* 43:31-39 (2005).

Goto, et al., "Endothelin activates the dihydropyridine-sensitive, voltage-dependent Ca2+ channel in vascular smooth muscle," *Proceedings of the National Academy of Sciences of the United States of America* 86:3915-3918 (1989).

Gulati, et al. "Cardiovascular effects of centrally administered endothelin-1 and its relationship to changes in cerebral blood flow," Life sciences 58:437-445 (1996).

Gulati, et al. "Effect of centrally administered endothelin agonists on systemic and regional blood circulation in the rat: role of sympathetic nervous system," Neuropeptides 31:301-309 (1997).

Gulati, et al., "Cardiovascular effects of centrally administered endothelin-1 in rats," Journal of cardiovascular pharmacology 26 Suppl 3:S244-246 (1995).

Gupta, et al. "Effect of endothelin antagonist (TAK-044) on cerebral ischemic volume, oxidative stress markers and neurobehavioral parameters in the middle cerebral artery occlusion model of stroke in rats," Life sciences 77:15-27 (2005).

Han, et al., "Cerebrovascular dysfunction in amyloid precursor protein transgenic mice: contribution of soluble and insoluble amyloid-beta peptide, partial restoration via gamma-secretase inhibition," *The Journal of neuroscience : the official journal of the Society for Neuroscience* 28:13542-13550 (2008).

Hardy, et al. "The amyloid hypothesis of Alzheimer's disease: progress and problems on the road to therapeutics," Science 297:353-356 (2002).

Hawkins, et al. "The blood-brain barrier/neurovascular unit in health and disease," Pharmacological reviews 57:173-185 (2005).

Hensley, et al., "A model for beta-amyloid aggregation and neurotoxicity based on free radical generation by the peptide: relevance to Alzheimer disease," *Proceedings of the National Academy of Sciences of the United States of America* 91:3270-3274 (1994).

Hermann, et al., "Implications of vascular endothelial growth factor for postischemic neurovascular remodeling," *Journal of cerebral blood flow and metabolism : official journal of the International Society of Cerebral Blood Flow and Metabolism* 29:1620-1643 (2009).

Hoehn, et al. "VEGF mRNA expressed in microvessels of neonatal and adult rat cerebral cortex," Brain Res Mol Brain Res 101:103-108 (2002).

(56) References Cited

OTHER PUBLICATIONS

Iadecola, et al. "Threats to the mind: aging, amyloid, and hypertension," *Stroke; a journal of cerebral circulation* 40:S40-44 (2009).
International preliminary report on patentability from PCT/US2014/045748 dated Jan. 12, 2016.
International search report from PCT/US2014/045748 dated Nov. 13, 2014.
Janson, et al., "Increased risk of type 2 diabetes in Alzheimer disease," *Diabetes* 53:474-481 (2004).
Johnson, et al., "Cognitive profiles in dementia: Alzheimer disease vs healthy brain aging," *Neurology* 71:1783-1789 (2008).
Kakkar, et al., "A modified spectrophotometric assay of superoxide dismutase," *Indian journal of biochemistry & biophysics* 21:130-132 (1984).
Kaundal, et al., "Targeting endothelin receptors for pharmacotherapy of ischemic stroke: current scenario and future perspectives," *Drug Discov Today* 17:793-804 (2012).
Kitazono, et al., "Enhanced responses of the basilar artery to activation of endothelin-B receptors in stroke-prone spontaneously hypertensive rats," *Hypertension* 25:490-494 (1995).
Kohzuki, et al., "Endothelin receptors in ischemic rat brain and Alzheimer brain," *Journal of cardiovascular pharmacology* 26 Suppl 3:S329-331 (1995).
Kojima, et al. Circulating levels of endothelin and atrial natriuretic factor during postnatal life Acta Paediatr 81:676-677 (1992).
Koyama, et al., "Endothelins reciprocally regulate VEGF-A and angiopoietin-1 production in cultured rat astrocytes: implications on astrocytic proliferation," *Glia* 60:1954-1963 (2012).
Koyama, et al. "I.c.v administration of an endothelin ET(B) receptor agonist stimulates vascular endothelial growth factor-A production and activates vascular endothelial growth factor receptors in rat brain," Neuroscience 192:689-698 (2011).
Laziz I, et al. "Endothelin as a neuroprotective factor in the olfactory epithelium," Neuroscience 172:20-29 (2011).
Lee, et al., "The endothelin receptor-B is required for the migration of neural crest-derived melanocyte and enteric neuron precursors," *Dev Biol* 259:162-175 (2003).
Leonard, et al., "Endothelin B receptor agonist, IRL-1620, enhances angiogenesis and neurogenesis following cerebral ischemia in rats," *Brain research* 1528:28-41 (2013).
Leonard, et al., "Endothelin B receptor agonist, IRL-1620, provides long-term neuroprotection in cerebral ischemia in rats," *Brain research* 1464:14-23 (2012).
Leonard, et al., "Endothelin B receptor agonist, IRL-1620, reduces neurological damage following permanent middle cerebral artery occlusion in rats," *Brain research* 1420:48-58 (2011).
Leonard, et al., "Repeated administration of ET(B) receptor agonist, IRL-1620, produces tachyphylaxis only to its hypotensive effect," *Pharmacological research : the official journal of the Italian Pharmacological Society* 60:402-410 (2009).
Levin, "Endothelins," The New England journal of medicine 333:356-363 (1995).
Li, et al., "The requirement of extracellular signal-related protein kinase pathway in the activation of hypoxia inducible factor 1 alpha in the developing rat brain after hypoxia-ischemia," *Acta neuropathologica* 115:297-303 (2008).
Liu, et al., "Contralesional axonal remodeling of the corticospinal system in adult rats after stroke and bone marrow stromal cell treatment," *Stroke; a journal of cerebral circulation* 39:2571-2577 (2008).
Loo, et al. "Cortical expression of endothelin receptor subtypes A and B following middle cerebral artery occlusion in rats," Neuroscience 112:993-1000 (2002).
Lopes, et al., "Neurodegeneration in an Abeta-induced model of Alzheimer's disease: the role of Cdk5," *Aging cell* 9:64-77 (2010).
Lowry, et al, "Protein measurement with the Folin phenol reagent," *The Journal of biological chemistry* 193:265-275 (1951).
Ly, et al. "Neuroprotection and thrombolysis: combination therapy in acute ischaemic stroke," Expert Opin Pharmacother 7:1571-1581 (2006).

Malik, et al., "Neurogenesis continues in the third trimester of pregnancy and is suppressed by premature birth," *The Journal of neuroscience : the official journal of the Society for Neuroscience* 33:411-423 (2013).
Mark, et al., "A role for 4-hydroxynonenal, an aldehydic product of lipid peroxidation, in disruption of ion homeostasis and neuronal death induced by amyloid beta-peptide," *Journal of neurochemistry* 68:255-264 (1997).
Mathers, et al., "Global and regional causes of death," *Br Med Bull* 92:7-32 (2009).
Meier-Ruge, et al. "Changes in brain glucose metabolism as a key to the pathogenesis of Alzheimer's disease," Gerontology 40:246-252 (1994).
Micieli, et al., "Safety and efficacy of alteplase in the treatment of acute ischemic stroke," *Vasc Health Risk Manag* 5:397-409 (2009).
Minami, et al. "Endothelin-1-like immunoreactivity in cerebral cortex of Alzheimer-type dementia" Progress in neuro-psychopharmacology & biological psychiatry 19:509-513 (1995).
Morris, "Developments of a water-maze procedure for studying spatial learning in the rat," *Journal of neuroscience methods* 11:47-60 (1984).
Murphy, "Plasticity during stroke recovery: from synapse to behaviour," *Nature reviews Neuroscience* 10:861-872 (2009).
Murray, et al., "Membrane-mediated amyloidogenesis and the promotion of oxidative lipid damage by amyloid beta proteins," *The Journal of biological chemistry* 282:9335-9345 (2007).
Murray, et al., "Promotion of oxidative lipid membrane damage by amyloid beta proteins," *Biochemistry* 44:12606-12613 (2005).
Nitta, et al. "β-Amyloid protein-induced Alzheimer's disease animal model," Neuroscience letters 170:63-66 (1994).
Niwa, et al. "Exogenous Aβ1-40 reproduces cerebrovascular alterations resulting from amyloid precursor protein overexpression in mice," *Journal of cerebral blood flow and metabolism : official journal of the International Society of Cerebral Blood Flow and Metabolism* 20:1659-1668 (2000).
Niwa, et al., "Aβ-peptides enhance vasoconstriction in cerebral circulation," *American journal of physiology Heart and circulatory physiology* 281:H2417-2424 (2001).
Niwa, et al., "Cerebrovascular autoregulation is profoundly impaired in mice overexpressing amyloid precursor protein," *American journal of physiology Heart and circulatory physiology* 283:H315-323 (2002).
Nowacka, et al., "Vascular endothelial growth factor (VEGF) and its role in the central nervous system: a new element in the neurotrophic hypothesis of antidepressant drug action," *Neuropeptides* 46:1-10 (2012).
Nunomura, et al., "Oxidative damage is the earliest event in Alzheimer disease," *Journal of neuropathology and experimental neurology* 60:759-767 (2001).
Ogunshola, et al. "Neuronal VEGF expression correlates with angiogenesis in postnatal developing rat brain," Brain research Developmental brain research 119:139-153 (2000).
Ohkawa, et al. "Assay for lipid peroxides in animal tissues by thiobarbituric acid reaction," Analytical biochemistry 95:351-358 (1979).
Paris, et al. "Nilvadipine antagonizes both Abeta vasoactivity in isolated arteries, and the reduced cerebral blood flow in APPsw transgenic mice," Brain research 999:53-61 (2004).
Patel, et al., "Therapeutic potential of endothelin receptor antagonists in experimental stroke," *Journal of cardiovascular pharmacology* 26 Suppl 3:S412-415 (1995).
Quinn, "Comparing rat's to human's age: how old is my rat in people years?" Nutrition 21:775-777 (2005).
Rebello, et al. "Systemic hemodynamic and regional circulatory effects of centrally administered endothelin-1 are mediated through ETA receptors," *Brain research* 676:141-150 (1995a).
Riechers, et al. "Endothelin B receptor deficient transgenic rescue rats: a rescue phenomenon in the brain," Neuroscience 124:719-723 (2004).
Roger, et al. "Heart disease and stroke statistics—2012 update: a report from the American Heart Association," *Circulation* 125:e2-e220 (2012).

(56) References Cited

OTHER PUBLICATIONS

Rosenstein, et al., "VEGF in the nervous system," *Organogenesis* 6:107-114 (2010).
Rubinsztein, "The roles of intracellular protein-degradation pathways in neurodegeneration," *Nature* 443:780-786 (2006).
Schinelli, "Pharmacology and physiopathology of the brain endothelin system: an overview," *Curr Med Chem* 13:627-638, (2006).
Schneider, et al, "Contrasting actions of endothelin ET(A) and ET(B) receptors in cardiovascular disease," *Annu Rev Pharmacol Toxicol* 47:731-759 (2007).
Search Report from European Application No. 14823205.1 dated Jan. 4, 2017.
Shin, et al., "Age-dependent cerebrovascular dysfunction in a transgenic mouse model of cerebral amyloid angiopathy," *Brain : a journal of neurology* 130:2310-2319 (2007).
Sims, et al., "Mitochondria, oxidative metabolism and cell death in stroke," *Biochimica et biophysica acta* pp. 80-91 (2009).
Smith, et al. "Soluble beta-amyloid (A beta) 40 causes attenuation or potentiation of noradrenaline-induced vasoconstriction in rats depending upon the concentration employed," Neuroscience letters 367:129-132 (2004).
Steinwachs, et al., "The future of cardiology: utilization and costs of care," *J Am Coll Cardiol* 35:91B-98B (2000).
Strong, et al. "Preventing stroke: saving lives around the world," Lancet Neurol 6:182-187 (2007).
Suo, et al. "Soluble Alzheimers beta-amyloid constricts the cerebral vasculature in vivo," Neuroscience letters 257:77-80 (1998).
Tirapelli, et al., "Functional characterization and expression of endothelin receptors in rat carotid artery: involvement of nitric oxide, a vasodilator prostanoid and the opening of K+ channels in ETB-induced relaxation," *British journal of pharmacology* 146:903-912 (2005).
Toda, et al., "Cerebral blood flow regulation by nitric oxide: recent advances," *Pharmacological reviews* 61:62-97 (2009).
Trollmann, et al., "HIF-1-regulated vasoactive systems are differentially involved in acute hypoxic stress responses of the developing brain of newborn mice and are not affected by levetiracetam," *Brain research* 1199:27-36 (2008).
Tsukahara, et al., "Molecular and functional characterization of the non-isopeptide-selective ETB receptor in endothelial cells," Receptor coupling to nitric oxide synthase. *The Journal of biological chemistry* 269:21778-21785 (1994).
Tsukuda, et al., "Cognitive deficit in amyloid-β-injected mice was improved by pretreatment with a low dose of telmisartan partly because of peroxisome proliferator-activated receptor-γ activation," *Hypertension* 54:782-787 (2009).
Vidovic, et al., "Deficiency in endothelin receptor B reduces proliferation of neuronal progenitors and increases apoptosis in postnatal rat cerebellum," *Cellular and molecular neurobiology* 28:1129-1138 (2008).
Viossat, et al., "Elevated tissue endothelin content during focal cerebral ischemia in the rat," *Journal of cardiovascular pharmacology* 22 Suppl 8:S306-309 (1993).
Virgintino, et al. "VEGF expression is developmentally regulated during human brain angiogenesis," Histochem Cell Biol 119:227-232 (2003).
Weller, et al., "Cerebral amyloid angiopathy: amyloid beta accumulates in putative interstitial fluid drainage pathways in Alzheimer's disease," *The American journal of pathology* 153:725-733 (1998).
Written opinion from PCT/US2014/045748 dated Nov. 13, 2014.
Yagami, et al. "Effects of endothelin B receptor agonists on amyloid beta protein (25-35)-induced neuronal cell death," Brain research 948:72-81 (2002).
Yagami, et al. "Effects of an endothelin B receptor agonist on secretory phospholipase A2-IIA-induced apoptosis in cortical neurons," Neuropharmacology 48:291-300 (2005).
Yoshizawa, et al. "Cerebrospinal fluid endothelin-1 in Alzheimer's disease and senile dementia of Alzheimer type," Neuropeptides 22:85-88 (1992).
Zhang, et al. "Astrocytes in Alzheimer's disease express immunoreactivity to the vaso-constrictor endothelin-1," Journal of the neurological sciences 122:90-96 (1994).
Zhang, et al. "A selective endothelin ET(A) receptor antagonist, SB 234551, improves cerebral perfusion following permanent focal cerebral ischemia in rats," Brain research 1045:150-156 (2005).
Zhang, et al., "Neurorestorative therapies for stroke: underlying mechanisms and translation to the clinic," *Lancet Neurol* 8:491-500 (2009).
Zhang, et al., "Synergistic effect of an endothelin type A receptor antagonist, S-0139, with rtPA on the neuroprotection after embolic stroke," *Stroke; a journal of cerebral circulation* 39:2830-2836 (2008).
Zlokovic, "New therapeutic targets in the neurovascular pathway in Alzheimer's disease," *Neurotherapeutics : the journal of the American Society for Experimental NeuroTherapeutics* 5:409-414 (2008).
Area-Gomez et al., "Mitochondria-associated ER membranes and Alzheimer Disease," Curr Opin Genet Dev. 38:90-96 (2016).
Briyal et al., "IRL-1620 prevents beta amyloid (Aβ) induced oxidative stress and cognitive impairment," Journal of Clinical PHarmacology 51(9):1349, Abstract No. 1123022 (2011).
Cali et al., "Enhanced parkin levels favor ER-mitochondria crosstalk and guarantee $Ca^{2+}$ transfer to sustain cell bioenergetics," Biochimica et Biophysica Acta 1832:495-508 (2013).
Cuervo, "Autophagy: In Sickness and in Health," Trends Cell Biol 14:70-77 (2004).
Hara et al., "Suppression of Basal Autophagy in Neural Cells Causes Neurodegenerative Disease in Mice," Nature 441:885-889 (2006).
Kopito et al., "Conformational Disease," Nat Cell Biol 2:E207-209 (2000).
Matus et al., "Protein Folding Stress in Neurodegenerative Diseases: A Glimpse Into the ER," Curr Opin Cell Biol 23:239-252 (2011).
Merkwirth et al., "Loss of Prohibitin Membrane Scaffolds Impairs Mitochondrial Architecture and Leads to Tau Hyperphosphorylation and Neurodegeneration," PLOS Genetics 8(11):e1003021, 13 pages (2012).
Nassif et al., "Autopagy impairment: a crossroad between neurodegeneration and tauopathies," BMC Biology 10(78), 4 pages (2012).
Rao et al., "Misfolded proteins, endoplasmic reticulum stress and neurodegeneration," Curr Opin Cell Biol. 16(6):653-662 (2004).
Selkoe, "Folding Proteins in Fatal Ways," Nature 426:900-904 (2003).
Taylor et al., "Toxic Proteins in Neurodegenerative Disease," Science 296:1991-1995 (2002).
Abo-Zena et al., "Hypertensive Urgency Induced by an Interaction of Mirtazapine and Clinidine," Pharmacotherapy 20:476-478 (2000).
Arya, "Centhaquin," Drugs of the Future 9(2):104-105 (1984).
Backo et al., "Clonidine-Induced Hypertension in a Patient with a Spinal Lesion," Ann Pharmacother 36:1396-1398 (2002).
Bajpai et al., "Fourier transform infrared spectra and normal mode analysis of 1-(3-methyl phenyl piperazin-1-yl)-2-(quinolin-2-yl)ethane (Centhaquin): a potent centrally acting anti-hypertensive agent," J. Molecular Structure 516:15-21 (2000).
Bell et al., Effect of endothelin-1 and sarafotoxin S6c on blood flow in a rat tumor, J. Cardiovasc. Pharmacol., 26(Suppl. 3):S222-5 (1995).
Bell et al., Modification of blood flow in the HSN tumour and normal tissues of the rat by the endothelin ETb receptor agonist, IRL 1620, Int. J. Cancer, 80:295-302 (1999).
Bennett, "The LANSS Pain Scale: the Leeds assessment of neuropathic symptoms and signs," Pain. 92:147-157 (2001).
Bhatnagar et al., "Effect of Centhaquine on Spontaneous and Evoked Norepinephrine Release from Isolated Perfused Rabbit Heart," Drug Res. 35(I):693-697 (1985).
Bomber et al., Propranolol hydrochloride enhancement of tumor perfusion and uptake of gallium-67 in a mouse sarcoma, J. Nucl. Med., 27(2):243-5 (1986).
Bonvallet et al., "BQ123, an $ET_A$-receptor antagonist, attenuates hypoxic pulmonary hyertension in rats," Am J Physiol 266:H1327-1331 (1994).

(56) References Cited

OTHER PUBLICATIONS

Bork, "Powers and Pitfalls in Sequence Analysis: The 70% Hurdle," Genome Res. 10(4):398-400 (2000).
Bousquet et al., "Pharmacological Tools for the Study of the Central Vasomotor Control," Biochem Pharmacol 32:1459-1465 (1983).
Brasch et al., Assessing tumor angiogenesis using macromolecular MR imaging contrast media, JMRI, 7:68-74 (1997).
Brenner, "Errors in genome annotation," Trends in Genetics, 15(4):132-3 (1999).
Brondani et al., "Levels of vascular cell adhesion molecule-1 and endothelin-1 in ischemic stroke: A longitudinal prospective study," Clin Biochem 40:282-284 (2007).
Brooks et al., Identification and function of putative ETB receptor subtypes in the dog kidney, J. Cardiovasc. Pharmacol., 26(Suppl 3):S322-5 (1995).
Carlsson, "Assessment of Chronic Pain. I. Aspects of the Reliability and Validity of the Visual Analogue Scale," Pain 16:87-101 (1983).
Carpy et al., "Structure of 1-(3-Methylphenyl)-4-(2-β-quinolylethyl)piperazone: Centhaquin," Acta Crystallographica C47:227-229 (1991).
Carrier et al., "Enhancement of Alpha-1 and Alpha-2 Adrenerigic Agonist-Induced Vasoconstriction by Removal of Endothelium in Rat Aorta," J Pharmacol Exp Ther 232:682-687 (1985).
Chakrabarti et al., "Therapeutic potential of endothelin receptor antagonists in diabetes," Expert Opinion on Investigational Drugs 9(12):2873-2888 (2000).
Chan et al., "Effects of endothelin-1 on portal-systemic collaterals of common bile duct-ligated cirrhotic rats," European Journal of Clinical Investigation 34(4):290-296 (2004).
Charu et al., "Inhaled corticosteroids and long term outcome in adults with asthma," Thorax 61:1011-1012 (2006).
Chen et al., "Physical Conditioning Decreases Norepinephrine-Induced Vasoconstriction in Rabbits—Possible Roles of Norepinephrine-Evoked Endothelium-Derived Relaxing Factor," Circulation 90:970-975 (1994).
Consigny, "Endothelin-1 increases arterial sensitivity to 5-hydroxytryptamine," Eur J Pharmacol 186:239-245 (1990).
Cowburn et al., "Selective or non-selective endothelin receptor antagonists for chronic heart failure: what do we know so far?", Journal of Clinical and Basic Cardiology 2(1):41-44 (1999).
D'Angelo et al., "In vivo evidence for endothelin-1-mediated attenuation of $\alpha_1$-adrenergic stimulation," Am J Physiol Heart Circ Physiol 290:H1251-1258 (2006).
Dillon et al., "A bioassay of Treatment of Hemorrhagic Shock," Archives of Surgery, 93(4):537-555, plus abstract (1966).
Doerks et al., Protein annotation: detective work for function prediction, Trends Genet., 14(6):248-50 (1998).
Fagura et al., "Pharmacological classification of α1-adrenoceptors mediating contractions of rabbit isolated ear artery: comparison with rat isolated thoracic aorta," Br J Pharmacol 120:247-258 (1997).
Gondre et al., "Endothelin-1-Induced Alterations in Phenylephrine-Induced Contractile Responses are Largely Additive in Physiologically Diverse Rabbit Vasculature," J Pharmacol Exp Ther 286:635-642 (1998).
Graf et al., Determination of optimal time window for liver scanning with CT during arterial portography, Radiology, 190:43-7 (1994).
Gulati et al., "Effect of Repeated Administration of Centhaquin, a Centrally Acting Hypotensive Drug, on Adrenergic, Cholinergic (Muscarinic), Dopaminergic, and Serotonergic Receptors in Brain Regions of Rat," Drug Development Research 23:307-323 (1991).
Gulati et al., "Effect of Repeated Administration of Clonidine on Adrenergic, Cholinergic (Muscarinic), Dopaminergic, and Serotonergic Receptors in Brain Regions of Rats," Drug Development Research 22:141-152 (1991).
Gulati et al., "Endothelin antagonizes the hypotension and potentiates the hypertension induced by clonidine," Eur J Pharmacol 230:293-300 (1993).
Gulati et al., "Role of sympathetic nervous system in cardiovascular effects of centrally administered endothelin-1 in rats," Am J Physiol 273:H1177-1186 (1997).
Gulati, "Evidence for Antagonistic Activity of Endothelin for Clonidine Induced Hypotension and bradycardia," Life Sci 50:153-160 (1992).
Guyenet et al. "Inhibition of Sympathetic Preganglionic Neurons by Catecholamines and Clonidine: Mediation by an α-Adrenergic Receptor," J Neurosci 1:908-917 (1981).
Harvey et al., Imaging of tumour therapy responses by dynamic CT, Eur. J. Radiology, 30:221-6 (1999).
Hegde et al., "Attenuation in Rat Brain Nitric Oxide Synthase Activity in the Coarctation Model of Hypertension," Pharmacol Res 36:109-114 (1997).
Hickey et al., "Characterization of a coronary vasoconstrictor produced by cultured endothelial cells," Am J Physiol 248:C550-556 (1985).
Hunyor et al., "Clonidine overdose," Br Med J 4:23 (1975).
Ikeda et al., "A New Endothelin Receptor Antagonist, TAK-044, Shows Long-Lasting Inhibition of Both $ET_A$- and $ET_B$-Mediated Blood Pressure Responses in Rats," J Pharmacol Exp Ther 270:728-733 (1994).
International Search Report in international application No. PCT/US2008/073581, dated Jul. 15, 2009.
International Search Report in international application No. PCT/US2010/032942, dated Jan. 24, 2011.
International Search Report in international application No. PCT/US2010/033083, dated Jan. 25, 2011.
Ishikawa et al., "Biochemical and pharmacological profile of a potent and selective endothelin B-receptor antagonist, BQ-788," Proc Natl Acad Sci USA 91(11):4892-4896 (1994).
Ishizuka et al., Endothelin-1 enhances vascular cell adhesion molecule-1 expression in tumor necrosis factor alpha-stimulated vascular endothelial cells, Eur. J. Pharmacol., 369(2):237-45 (1999).
Jarajapu et al. "The $\alpha_{1A}$-adrenoceptor subtype mediates contraction in rat femoral resistance arteries," Eur J Pharmacol 422:127-135 (2001).
Katayama, Current trends in the treatment of acute ischemic stroke, Nichiidaishi, 65(3):4-9 (1999).
Kennedy et al., "Centrally Acting Imidazolines Stimulate Vascular Alpha 1A-Adrenergic Receptors in Rat-Tail Artery," Cell Mol Neurobiol 26:645-657 (2006).
Kobinger et al. "Kreislaufuntersuchungen mit 2-(2,6-Dichlorphenylamino)-2-imidazolin-hydrochlorid," Arzneimittelforschung 17:292-300 (1967).
Kobinger, "Central α-Adrenergic Systems as Targets for Hypotensive Drugs," Rev Physiol Biochem Pharmacol 81:39-100 (1978).
Kuwaki et al., "Modulatory Effects of Rat Endothelin on Central Cardiovascular Control in Rats," Jpn J Physiol 40:97-116 (1990).
Langer et al, "Recent Developments in Noradrenergic Neurotransmission and its Relevance to the Mechanism of Action of Certain Antihypertensive Agents," Hypertension 2:372-382 (1980).
Meller et al., "The Possible Role of Flia in Nociceptive Processing and Hyperalgesia in the Spinal Cord of the Rat," Neuropharmacol. 33:1471-8 (1994).
Murti et al., "Synthesis and OSAR of 1-aryl-4-(β-2-quinolyl/1-isoquinolylethyl)piperazines and some related compounds as hypotensive agents," Indian Journal of Chemistry 28B:934-942 (1989).
Muruganandham et al., Diltiazem enhances tumor blood flow: MRI study in a murine tumor, Int. J. Radiation Oncology Biol. Phys., 43(2):413-21 (1999).
Naftchi et al., "Autonomic Dysreflexia: Pharmacological Management of Hypertensive Crises in Spinal Cord Injured Patients," J Spinal Cord Med 20:355-360 (1997).
Nakayama et al., "Potentiation by endothelin-1 of 5-hydroxytryptamine-induced contraction in coronary artery of the pig," Br J Pharmacol 104:978-986 (1991).
Ngo et al., The Protein Folding Problem and Tertiary Structure Prediction, Chapter 14 in Computational Complexity Protein Structure Prediction and the Levinthal Paradox, pp. 492-495 (1995).
Nowicki et al., "Endothelin-1 in Human Intestine Resected for Necrotizing Enterocolitis," J Pediatr 146:805-810 (2005).

(56) References Cited

OTHER PUBLICATIONS

Nv et al., N-Suc-[Glu9, Ala11, 15]ET-1(8-21) increases blood perfusion and enhances paclitaxel delivery to the tumor, 96th Annual Meeting of the American Association for Cancer Research, Abstract 5741 (2005).
Ouchi et al., "Central effect of endothelin on blood pressure in conscious rats," Am J Physiol 256:H1747-H1751 (1989).
Pacher et al., "Measurement of cardiac function using pressure-volume conductance catheter technique in mice and rats," Nat Protoc 3:1422-1434 (2008).
Pai et al., "Clonidine Poisoning," Pediatrics 58:749-750 (1976).
Pannen et al., "Role of Endothelins and Nitric Oxide in Hepatic Reperfusion Injury in the Rat," Hepatology, 27(3):755-764 (1998).
Patel et al., Endothelin receptor mediated constriction and dilatation in feline cerebral resistance arterioles in vivo, Eur. J. Pharmacol., 307:41-8 (1996).
Phillips, "The challenge of gene therapy and DNA delivery," J. Pharm. Pharmacol., 53(9):1169-74 (2001).
Radovits et al., "Endothelial dysfunction after hypoxia-reoxygenation: Do in vitro models work," Vascul Pharmacol 51:37-43 (2009).
Rai et al., Evidence for the involvement of ET(B) receptors in ET-1-induced changes in blood flow to the rat breast tumor, Cancer Chemother. Pharmacol., 51(1):21-8 (2003).
Recht et al., The sequencing of chemotherapy and radiation therapy after conservative surgery for early-stage breast cancer, NEJM, 334(21):1356-61 (1996).
Ruetten et al., "Effects of the endothelin receptor antagonist, SB 209670, on circulatory failure and organ injury in endotoxic shock in the anaesthetized rat," British Journal of Pharmacology, 118(1):198-204 (1996).
Sakamoto et al., "Distinct Subdomains of Human Endothelin Receptors Determine Their Selectivity to EndothelinA-selective Antagonist and EndothelinB-selective Agonists," J Biol Chem 268:8547-8553 (1993).
Sardanelli et al., Dynamic helical CT of breast tumors, J. Comp. Assisted Tomography, 22(3):398-407 (1998).
Schmitt et al., "Localization of the Hypotensive Effect of 2-(2-6-Dichlorophenylamino)-2-Imidazoline Hydrochloride (St 155, Catapresan)," Eur J Pharmacol 6:8-12 (1969).
Shetty et al. Biochem Biophys Res Commun 191:459-464 (1993).
Skolnick et al., "From genes to protein structure and function: novel applications of computational approaches in the genomic era," Trends Biotechnol., 18(1):34-9 (2000).
Smyth et al., Use of vasoactive agents to increase tumor perfusion and the antitumor efficacy of drug-monoclonal antibody conjugates, J. Natl. Cancer Inst., 79(6):1367-73 (1987).
Sonveaux et al., Endothelin-1 is a critical mediator of myogenic tone in tumor arterioles: implications for cancer treatment, Cancer Res., 64(9):3209-14 (2004).
Souza et al., "Increased Cardiac Sympathetic Drive and Reduced Vagal Modulation Following Endothelin Receptor Antagonism in Healthy Conscious Rats," Clin Exp Pharmacol Physiol 35:751-756 (2008).

Srimal et al., "Pharmacological studies on 2-(2-(4-(3-methylphenyl)-1-Piperazinyl)Ethyl) Quinoline (Centhaquin). I. Hypotensive Activity," Journal of the Italian Pharmac Pharmacol Res 22:319-329 (1990).
Stein et al, "The Discovery of Sulfonamide Endothelin Antagonists and the Development of the Orally Active ETA Antagonist 5-(Dimethylamino)-N-(3,4-dimethyl-5-isoxazolyl)-1-naphthalenesulfonamide," J Med Chem 37:329-331 (1994).
Supplementary European Search Report in counterpart foreign Application No. EP10770318, dated Oct. 23, 2012.
Tabuchi et al., "Endothelin Inhibits Presynaptic Adrenergic Neurotransmission in Rat Mesenteric Artery," Biochem Biophys Res Commun 161:803-808 (1989).
Takagawa et al., Efficacy of the drugs administered to the patients with cerebral vascular diseases from a viewpoint of cerebral blood flow measurement, 48(9):667-93 (1994).
Timmermans et al., "Postsynaptic a1- and a2-Adrenoceptors in the Circulatory System of the Pithed Rat: Selective Stimulation of the a2-Type by B-HT 933," Eur J Pharmacol 63:199-202 (1980).
Troncoso et al., "Hypertensive Urgency with Clonidine and Mirtazepine," Psychosomatics 45:449-450 (2004).
U'Prichard et al., "Binding Characteristics of a Radiolabeled Agonist and Antagonist at Central Nervous System Alpha Noradrenergic Receptors," Mol Pharmacol 13:454-473 (1977).
van Zwieten et al., "The Hypotensive Activity and Side Effects of Methyldopa, Clonidine, and Guanfacine," Hypertension 6:II28-33 (1984).
Vazquez-Prado et al., "Activiation of Endothelin ETA Receptors Induces Phosphorylation of ?1b-Adrenoreceptors in Rat-1 Fibroblasts," J Biol Chem 272:27330-27337 (1997).
Watts, "5-Hydroxytryptamine-Induced Potentiation of Endothelin-1- and Norepinephrine-Induced Contraction Is Mitogen-Activated Protein Kinase Pathway Dependent," Hypertension 35:244-248 (2000).
Watts, "The love of a lifetime: 5-HT in the cardiovascular system," Am J Physiol Regul Integr Comp Physiol R252-R256 (2009).
Wells, "Additivity of Mutational Effects in Proteins," Biochem., 29(37):8509-17 (1990).
Wiklund et al., "Inhibition of adrenergic neuroeffector transmission by endothelin in the guinea-pig femoral artery," Acta Physiol Scand 134:311-312 (1988).
Williamson et al., "Pain: a review of three commonly used pain rating scales," J. Clin Nurs. 14:798-804 (2005).
Wise, et al. "New clinical guidelines for stroke published," BMJ 320:823 (2000).
Wu et al., "Recent discovery and development of endothelin receptor antagonists," Exp. Opin. Ther. Patents 10(11):1653-1668 (2000).
Yanagisawa et al., "A Novel potent vasoconstrictor peptide produced by vascular endothelial cells," Nature 332:411-415 (1988).
Zuccarello, M., et al., "Endothelin B Receptor Antagonists Attenuate Subarachnoid Hemorrhage-Induced Cerebral Vasospasm," Stroke, Journal of the American Heart Association, Sep. 1998, vol. 29, No. 9, pp. 1924-1929.

\* cited by examiner

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: IRL-1620
<220> FEATURE:
<221> NAME/KEY: MISC_FEATURE
<222> LOCATION: (1)..(1)
<223> OTHER INFORMATION: N-succinyl group at N-terminus

<400> SEQUENCE: 1

Asp Glu Glu Ala Val Tyr Phe Ala His Leu Asp Ile Ile Trp
1               5                   10
```

COMPOSITIONS AND METHODS FOR TREATING NEUROPSYCHIATRIC DISORDERS USING AN ENDOTHELIN-B RECEPTOR AGONIST

CROSS REFERENCE TO RELATED APPLICATIONS

This application is a U.S. National Phase of International Application No. PCT/US2014/45748 filed Jul. 8, 2014, incorporated herein by reference, which claims the priority benefit under 35 U.S.C. § 119(e) of U.S. Provisional Patent Application No. 61/843,702, filed Jul. 8, 2013, and U.S. Provisional Patent Application No. 61/902,935, filed Nov. 12, 2013, the disclosures of which are incorporated herein by reference in their entirety.

INCORPORATION BY REFERENCE OF MATERIAL SUBMITTED ELECTRONICALLY

This application contains, as a separate part of disclosure, a Sequence Listing in computer-readable form (filename: 48812_SeqListing.txt; created Jul. 8, 2014, 659 bytes—ASCII text file) which is incorporated by reference in its entirety.

FIELD OF THE INVENTION

The present invention relates to compositions and methods for treating neuropsychiatric disorders in vertebrates and humans. More specifically, the present invention provides for use of an endothelin-B receptor agonist as a neuroprotective and a neuroregenerative agent.

BACKGROUND OF THE INVENTION

Endothelin (ET) is an endogenous peptide which has been implicated in numerous physiological and pathological phenomena within the body. Acting upon two distinct receptors, $ET_A$ and $ET_B$, ET influences a range of processes from regulation of blood pressure to neurotransmitters and hormones (Kojima et al., 1992; Levin, 1995; Schiffrin et al., 1997; Schneider et al., 2007). Although most widely studied for their actions on cardiovascular system, ET receptors are widespread throughout the body, including the brain. $ET_B$ receptors, specifically, are located in abundance on neurons and glial cells, as well as endothelial lining of the cerebral vasculature (Schinelli, 2006). The exact function of these receptors within the brain, particularly during its development, is not well understood.

Development of the Central Nervous System

A deficiency in $ET_B$ receptors at birth has been shown to result in a decrease in neuronal progenitor cells and an increase in apoptosis within the postnatal dentate gyms and cerebellum of rats (Ehrenreich et al., 2000; Vidovic et al., 2008). Additionally, $ET_B$ knockout model in rats leads to congenital aganglionosis within the gut and associated CNS disturbances (Dembowski et al., 2000). These $ET_B$ knockout rats, which have a 4 week postnatal mortality, serve as models for human Hirschsprung disease. Previous studies have shown that brain $ET_B$ receptor expression is particularly high immediately after birth, but drops down to lower levels by postnatal day 21 (Briyal et al., 2012b). The locations of these receptors and their correlation, or lack thereof, with CNS growth factors during these crucial stages of development remain to be determined.

While it is clear that $ET_B$ receptors are needed for normal CNS development, it remains uncertain which cells or pathways they exert a protective or proliferative influence on. Previous studies have shown that selective stimulation of $ET_B$ receptors produces neuroprotection against oxidative stress and a significant reduction in infarct volume in the brains of adult rats subjected to cerebral ischemia (Leonard et al., 2011; 2012). It was also found that protection and recovery from the ischemic condition was at least partially due to an increase in angiogenesis and neurogenesis within 7 days following infarct and treatment with $ET_B$ receptor agonist, IRL-1620 (Leonard and Gulati, 2013). An increase in vascular and nerve growth factors within the brain of IRL-1620-treated infarcted animals coincided with an increase in the level of $ET_B$ receptors.

Vascular endothelial growth factor (VEGF) is expressed normally in the cerebral microvessels as well as in the neuronal tissue of both neonates and adults (Hoehn et al., 2002). VEGF in the fetal human brain is located on neuroepithelial cells, neuroblasts, radial glial cells and endothelial cells, and its expression appears to be developmentally regulated and correlated with angiogenesis (Virgintino et al., 2003). While VEGF is well known to be necessary for blood vessel growth, recent research has indicated that it also plays a significant role in promoting neurogenesis, neuronal patterning, and neuronal migration (Rosenstein et al., 2010). It has been shown that there is a correlation between VEGF, neuronal growth factor (NGF) and $ET_B$ receptors in the developing brain. $ET_B$ receptors can be stimulated by administering $ET_B$ receptor agonists such as IRL-1620 and growth of the CNS treat diseases can be promoted where CNS has been damaged or has not grown appropriately.

Neurodegenerative Diseases

Neurodegeneration is a term for the progressive loss of structure or function of neurons, including death of neurons. Many neurodegenerative diseases including Amyotrophic lateral sclerosis (ALS), Parkinson's, Alzheimer's, and Huntington's occur as a result of neurodegenerative processes. As research progresses, many similarities appear that relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death (Bredesen et al., 2006; Rubinsztein, 2006).

Alzheimer's disease (AD) is a neurodegenerative disorder characterized by cerebrovascular and neuronal dysfunctions leading to a progressive decline in cognitive functions. Neuropathological hallmarks of AD include beta amyloid (Aβ) plaques and neurofibrillary tangles (Johnson et al., 2008). It has long been speculated that cerebrovascular dysfunction contributes to AD. Aβ has been shown to decrease myogenic response, cerebral blood flow (CBF) and vasodilator responses (Han et al., 2008; Niwa et al., 2000; Paris et al., 2004; Shin et al., 2007). Regulation of CBF tends to be impaired in transgenic mice with high intracerebral levels of Aβ (Niwa et al., 2002). Synthetic Aβ has been shown to impair endothelin (ET) dependent relaxation and enhance vasoconstriction in vivo and in vitro (Niwa et al., 2000; Niwa et al., 2001).

Several studies have demonstrated an involvement of ET in AD. ET is an endogenous vasoregulatory peptide which targets two main receptors—$ET_A$ and $ET_B$. $ET_A$ receptors are mainly located on vascular smooth muscle cells and mediate vasoconstriction, whereas $ET_B$ receptors are mainly located on vascular endothelial cells and mediate vasodilatation (Goto et al., 1989; Tsukahara et al., 1994). ET has been demonstrated to be present in the brain and plays an important role in the regulation of cerebral and systemic blood circulation (Gulati et al., 1997; Gulati et al., 1996; Gulati et al., 1995; Rebello et al., 1995a). It was initially demonstrated that ET-1 concentrations in the cerebrospinal fluid of patients with AD were lower compared to control (Yoshizawa et al., 1992), however, subsequent studies indicate that ET-1 like immunoreactivity was significantly increased in the cerebral cortex (frontal and occipital lobes) of patients that suffered from AD compared to control brains (Minami et al., 1995). Brain samples of AD patients obtained post mortem showed increased expression of ET-1 immunoreactivity in astrocytes (Zhang et al., 1994). It has been suggested that ET-1 released from astrocytes may reach the vascular smooth muscle cells and induce vasoconstriction. ET binding sites in the human brains with AD were found to be decreased which could be due to loss of neurons in the cortex (Kohzuki et al., 1995).

The mechanism by which soluble Aβ interferes with vascular function is not fully understood. A possible mechanism by which soluble Aβ interferes with vascular function may be mediated through ET-1 which plays a central role in the regulation of cardiovascular functions and regional blood flow (Gulati et al., 1997; Gulati et al., 1996; Gulati et al., 1995). It was previously found that specific $ET_A$ receptor antagonists (BMS182874 and BQ123) prevent Aβ induced oxidative stress and cognitive deficits (Briyal et al., 2011). Specific $ET_A$ receptor antagonists reduced escape latencies and also increased preference for the target quadrant. On the other hand, a nonspecific $ET_A/ET_B$ receptor antagonist (TAK-044) did not produce any improvement in spatial memory deficit or loss of preference for the target quadrant (Briyal et al., 2011). This lack of improvement with the non-specific $ET_A/ET_B$ antagonist indicated to us the specific involvement of $ET_B$ receptors in AD.

ET binding sites in the brain are predominantly of $ET_B$ receptors, and $ET_B$ receptor agonists have been shown to be anti-apoptotic against neurotoxicity of Aβ (Yagami et al., 2002). Complete deficiency or blockade of $ET_B$ receptors leads to exacerbation of ischemic brain damage, possibly due to the shift in ET vasomotor balance (Chuquet et al., 2002; Ehrenreich et al., 1999). It has been demonstrated that activation of $ET_B$ receptors with intravenous IRL-1620, a highly selective $ET_B$ agonist, results in a significant elevation in CBF in normal rats and reduction in neurological deficit and infarct volume of stroked rats (Leonard et al., 2011; Leonard and Gulati, 2009). It was further found that the efficacy of IRL-1620 in a rat model of stroke was completely antagonized by BQ788 indicating an involvement of $ET_B$ receptors (Leonard et al., 2011; 2012).

Stroke and Cerebrovascular Disorders

Stroke is the rapid loss of brain function due to disturbance in the blood supply to the brain, which can be due to ischemia or a hemorrhage (Sims and Muyderman, 2009). It is the second leading cause of death and the fourth leading cause of disability worldwide (Mathers et al., 2009; Strong et al., 2007). It is also a predisposing factor for epilepsy, falls and depression (Fisher and Norrving, 2011) and is a foremost cause of functional impairments, with 20% of survivors requiring institutional care after 3 months and 15%-30% being permanently disabled (Steinwachs et al., 2000).

Stroke is divided into two broad categories: Ischemic strokes, caused by sudden occlusion of arteries supplying the brain, either due to a thrombus at the site of occlusion or formed in another part of the circulation. According to recent data released by the American Heart Association, 87% of strokes are classified as ischemic (Deb et al., 2010; Feigin et al., 2009; Roger et al., 2012). Hemorrhagic strokes, caused by bleeding from one of the brain's arteries into the brain tissue (subarachnoid hemorrhage) or arterial bleeding in the space between meninges (intra-cerebral hemorrhage).

The outcome after a stroke depends on the site and severity of brain injury. A very severe stroke can cause sudden death. Stroke affected area of the brain cannot function, which may result in an inability to move one or more limbs on one side of the body, inability to understand or formulate speech, or an inability to see one side of the visual field (Bath and Lees, 2000; Donnan et al., 2008). Early recognition of stroke is most important in order to expedite diagnostic tests and treatments.

Despite the severity of ischemic stroke, the only currently available FDA-approved pharmacological treatment is recombinant tissue plasminogen activator (rtPA), which dissolves the clot and restores blood flow to the brain. This treatment is complicated by the relatively short window of time between infarct and treatment (3-4 h) and the increased risk of subarachnoid hemorrhage (Micieli et al., 2009). A large number of other agents, broadly classified as neuroprotective and aiming to slow or stop the secondary damage associated with the ischemic cascade following stroke, have shown promise in the initial stages of research but have thus far failed to demonstrate efficacy in clinical trials (Ly et al., 2006). A new approach is therefore needed, one which has the potential to address both the restoration of blood flow and attenuate secondary damage to the penumbral area.

Following both ischemic stroke and subarachnoid hemorrhage, ET levels in the blood and ET immunoreactivity in the tissues are elevated (Asano et al., 1990; Rebello et al., 1995b; Viossat et al., 1993). A demonstration that the increase in ET levels coincides with a decrease in regional blood flow in the ischemic areas of the brain following experimental stroke led to the investigation of several ET antagonists in the treatment of focal ischemic stroke (Patel et al., 1995). Although some ETA specific and ETA/B non-specific antagonists have shown promise in experimental stroke models, others have not (Barone et al., 2000; Barone et al., 1995; Briyal and Gulati, 2010; Briyal et al., 2007; Briyal et al., 2012a; Gupta et al., 2005; Kaundal et al., 2012; Zhang et al., 2008; Zhang et al., 2005). Overall, this approach has not been useful. It has been demonstrated that $ET_B$ receptors, which increase VEGF and NGF in the brain, are overexpressed at the time of birth and their expression decreases with maturity of the brain (Briyal et al., 2012b). It appears that $ET_B$ receptors present in large number in the CNS play a key role in its development. This fundamental information demonstrates the possible involvement of $ET_B$ receptor in the brain development to generate neurovascular plasticity of the brain that has been damaged following cerebral ischemia. It was found that stimulation of $ET_B$ receptors with intravenous IRL-1620, a highly selective $ET_B$ agonist, resulted in a significant elevation in cerebral blood flow in normal rats (Leonard and Gulati, 2009). In addition, functional $ET_B$ receptors have been shown to enhance proliferation of neuronal progenitors and to protect against apoptosis in the dentate gyms, olfactory epithelium, and cortical neurons (Ehrenreich et al., 1999; Laziz et al., 2011; Lee et al., 2003; Yagami et al., 2005). The evidence that a deficiency in $ET_B$ receptors leads to a poorer outcome following cerebral ischemia (Chuquet et al., 2002) and complete deficiency or blockade of $ET_B$ receptors leads to exacerbation of ischemic brain damage (Ehrenreich et al., 1999) led to the investigation of the role of $ET_B$ receptors in a model of ischemic stroke. When a majority of research on ET and stroke thus far has focused on antagonizing $ET_A$ receptors selectively or non-selectively in order to prevent excessive vasoconstriction, the effect of selectively activating ETB receptors in a focal stroke model was examined (Leonard et al., 2011; 2012; Leonard and Gulati, 2013).

In clinical practice at present there are two basic treatments, preventive treatment using long term antiplatelet or anticoagulant agents to reduce the risk of stroke, or acute treatment by fibrinolytics. However, less than 2% of patients are able to receive fibrinolytics (Font et al., 2010). Extensive research is being conducted in search of neuroprotective agents for possible use in acute phase of stroke, and of agents that can be used for neurorepair in later stages of stroke.

SUMMARY OF THE INVENTION

The present invention relates to compositions and methods for treating neuropsychiatric disorders in vertebrates and humans. More specifically, the present invention provides for use of IRL-1620, an endothelin-B receptor agonist, in appropriate doses to be a neuroprotective and a neuroregenerative agent.

Accordingly, in one aspect the disclosure provides a method of treating a neuropsychiatric disorder comprising administering to a patient in need thereof a therapeutically effective amount of an endothelin-B receptor agonist to treat the neuropsychiatric disorder.

In some embodiments, the endothelin-B receptor agonist is co-administered with an additional agent to treat the neuropsychiatric disorder. In some embodiments, the additional agent is selected from the group consisting of an antidepressant, an anti-inflammatory agent, a CNS stimulant, a neuroleptic, and an anti-proliferative agent.

In additional embodiments, the endothelin-B receptor agonist is selected from the group consisting of IRL-1620, BQ-3020, $[Ala^{1,3,11,15}]$-Endothelin, Sarafotoxin S6c, endothelin-3, and a mixture thereof.

The present disclosure contemplates that in further embodiments, the neuropsychiatric disorder is selected from the group consisting of a cerebrovascular disease, stroke, cerebral ischemia, cerebral hemorrhage, head trauma, brain injury, a brain tumor, multiple sclerosis and demyelinating diseases, dementia, vascular dementia, Alzheimer's disease, Parkinson's disease, Huntington's disease, ataxia, motor neuron disease, Amyotrophic lateral sclerosis, drug intoxication, alcoholism, chronic brain infections, brain abscess, white matter disease, Binswanger's disease, Moyamoya disease, perinatal hypoxia, cerebral asphyxia, intracranial birth injury, congenital malformation of the brain, mood disorders, and depression.

In some embodiments, the endothelin-B receptor agonist is administered at a dose ranging from 0.0001 to 0.5 mg/kg. In further embodiments, the endothelin-B receptor agonist is administered repeatedly at intervals of 1 to 6 hours after every two to five days.

In any of the embodiments of the disclosure, it is contemplated that the patient is a mammal. In some embodiments, the mammal is a human.

In another aspect, the disclosure provides a composition comprising (a) an endothelin-B receptor agonist, (b) an agent used to treat a neuropsychiatric disorder, and optionally (c) an excipient.

The disclosure also provides, in an additional aspect, an article of manufacture comprising (a) a packaged composition comprising an endothelin-B receptor agonist and an agent for a neuropsychiatric disorder; (b) an insert providing instructions for a simultaneous or sequential administration of the endothelin-B receptor agonist and the agent for the neuropsychiatric disorder to treat a patient in need thereof; and (c) a container for (a) and (b). In some embodiments, the endothelin-B receptor agonist is IRL-1620.

DETAILED DESCRIPTION OF THE INVENTION

Figure 1:
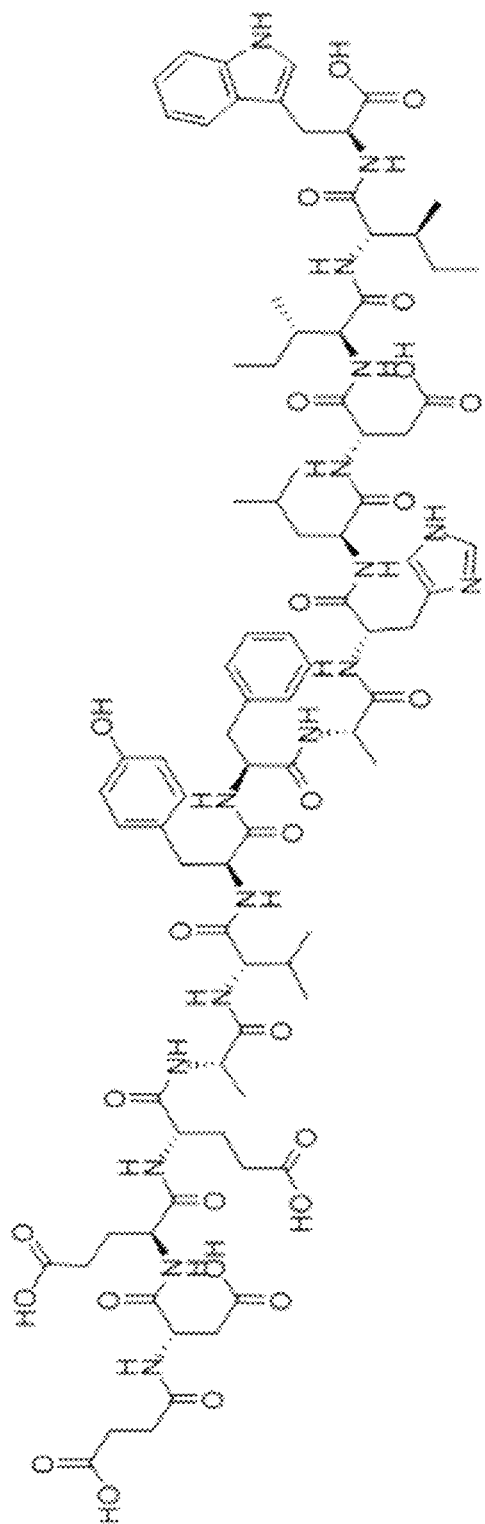
FIG. 1. Structure of IRL-1620 (Suc-Asp-Glu-Glu-Ala-Val-Tyr-Phe-Ala-His-Leu-Asp-Ile-Ile-Trp; SEQ ID NO: 1).
Figure 2A:
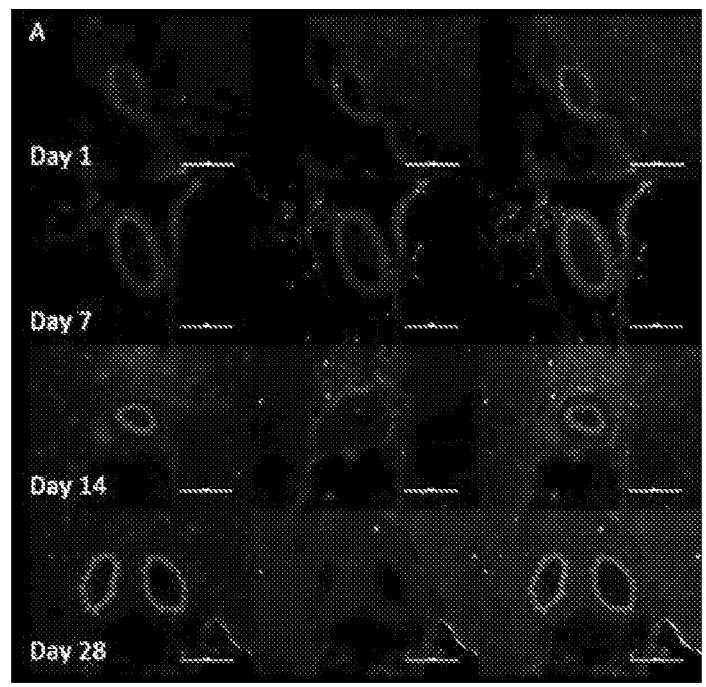
FIG. 2. Expression of vascular endothelial growth factor and endothelin B receptors in the vasculature of the postnatal rat brain. A) Representative images of blood vessels in the rat cortex at postnatal days 1, 7, 14 and 28, stained for VEGF (red) and $ET_B$ receptors (green). Scale bar=10 µm. B) Intensity of VEGF in the rat brain vasculature at postnatal days 1, 7, 14 and 28. C) Number of VEGF-positive vessels per 20 µm-thick rat brain slice at postnatal days 1, 7, 14 and 28. D) Intensity of $ET_B$ receptors in the rat brain vasculature at postnatal days 1, 7, 14 and 28. *$P<0.05$ vs. day 1; #$P<0.01$ vs. day 7. Values are expressed as mean±SEM. 30 male pups were divided into following groups: Day 1 (N=10); Day 7 (N=10); Day 14 (N=5); Day 28 (N=5).
Figure 2B:
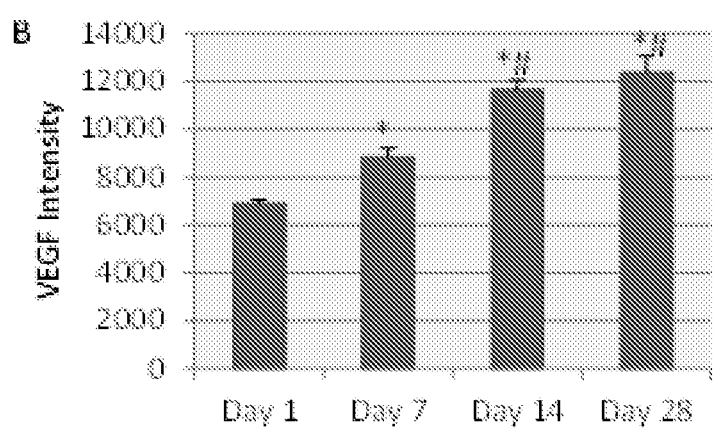
Figure 2C:
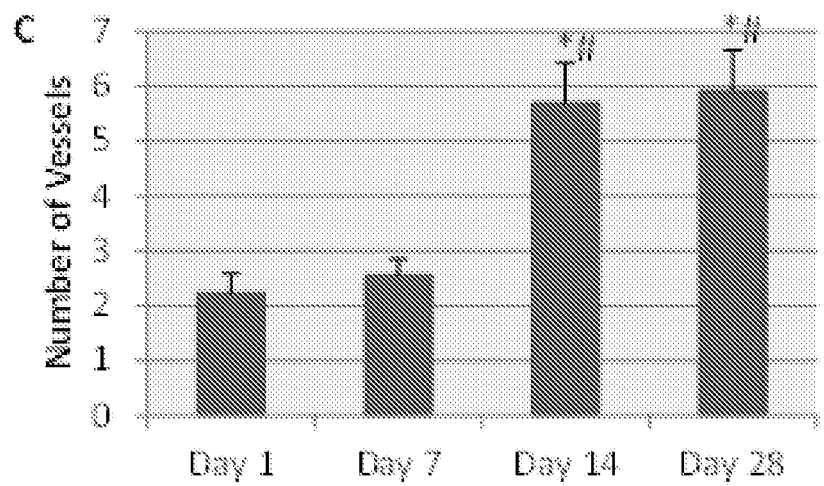
Figure 2D:
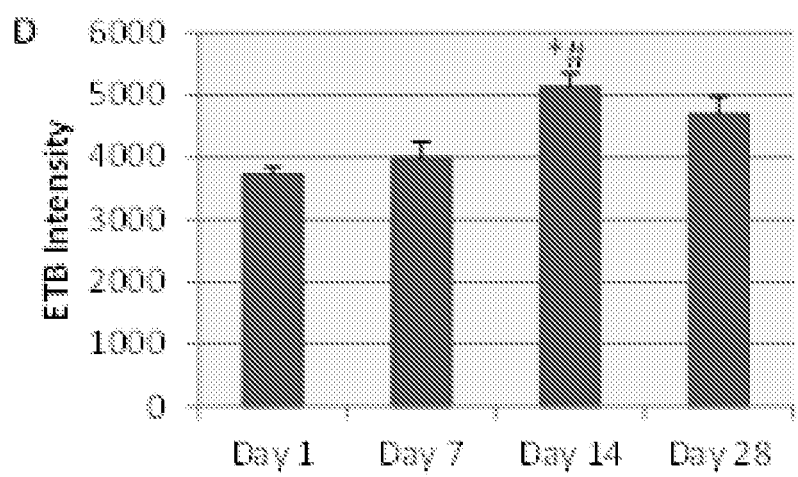
Figure 3A:
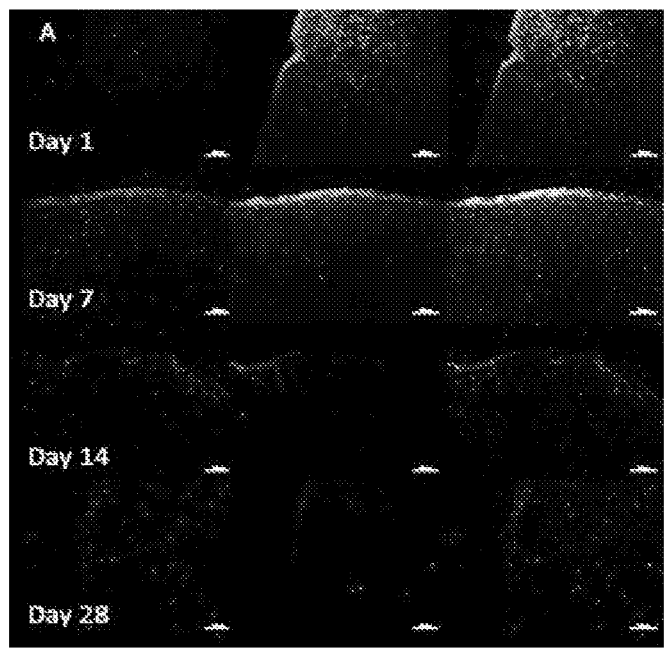
FIG. 3. Expression of nerve growth factor and endothelin B receptors in the cortex and subventricular zone of the postnatal rat brain. A) Representative images of the rat cortex at postnatal days 1, 7, 14 and 28, stained for NGF (red) and $ET_B$ receptors (green). Scale bar=100 µm. B) Representative images of the rat SVZ at postnatal days 1, 7, 14 and 28, stained for NGF (red) and $ET_B$ receptors (green). Scale bar=100 µm. C) Intensity of NGF in the cortex and SVZ of the rat brain at postnatal days 1, 7, 14 and 28. D) Number of NGF-positive cells per 100 µm² in the cortex and SVZ of the rat brain at postnatal days 1, 7, 14 and 28. E) Intensity of $ET_B$ receptors in the cortex and SVZ of the rat brain at postnatal days 1, 7, 14 and 28. *$P<0.001$ vs. day 1; #$P<0.01$ vs. day 7. Values are expressed as mean±SEM. 30 male pups were divided into following groups: Day 1 (N=10); Day 7 (N=10); Day 14 (N=5); Day 28 (N=5).
Figure 3B:
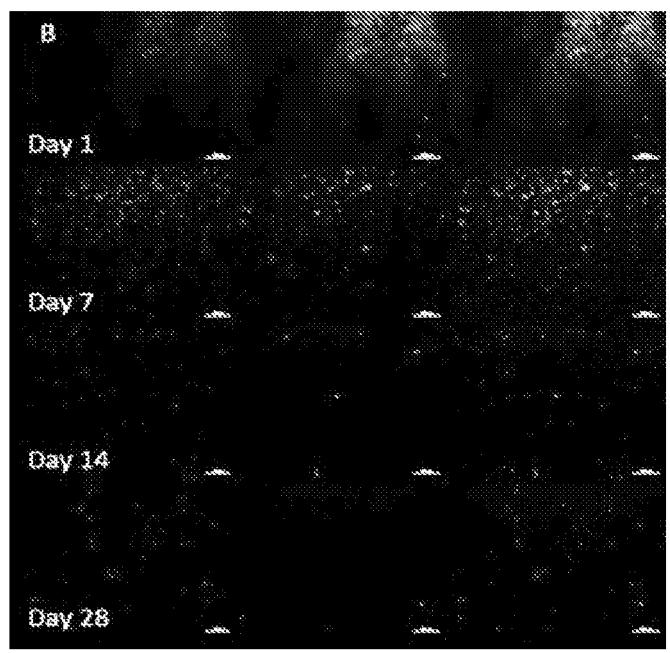
Figure 3C:
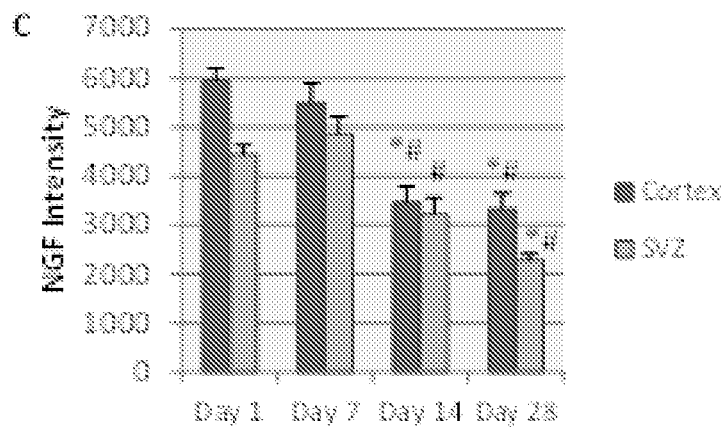
Figure 3D:
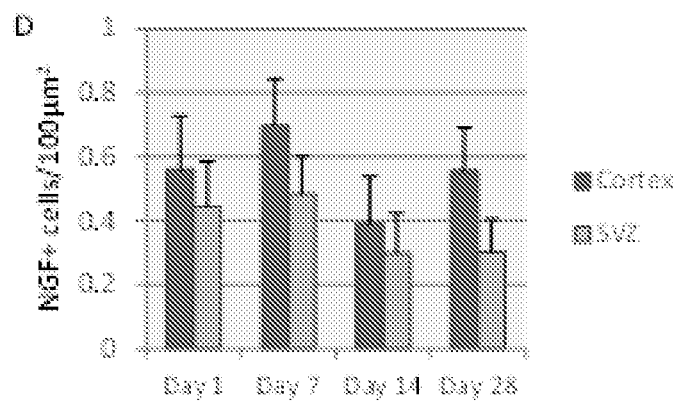
Figure 3E:
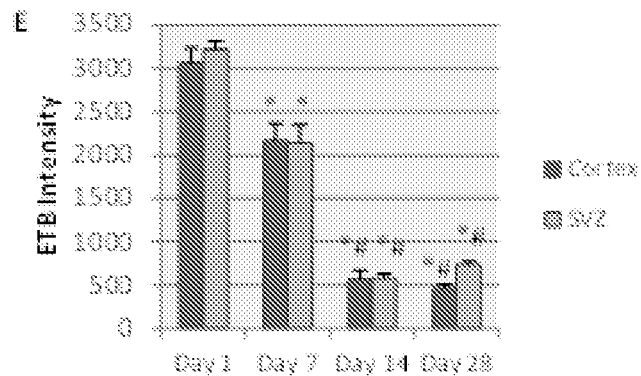
Figure 4A:
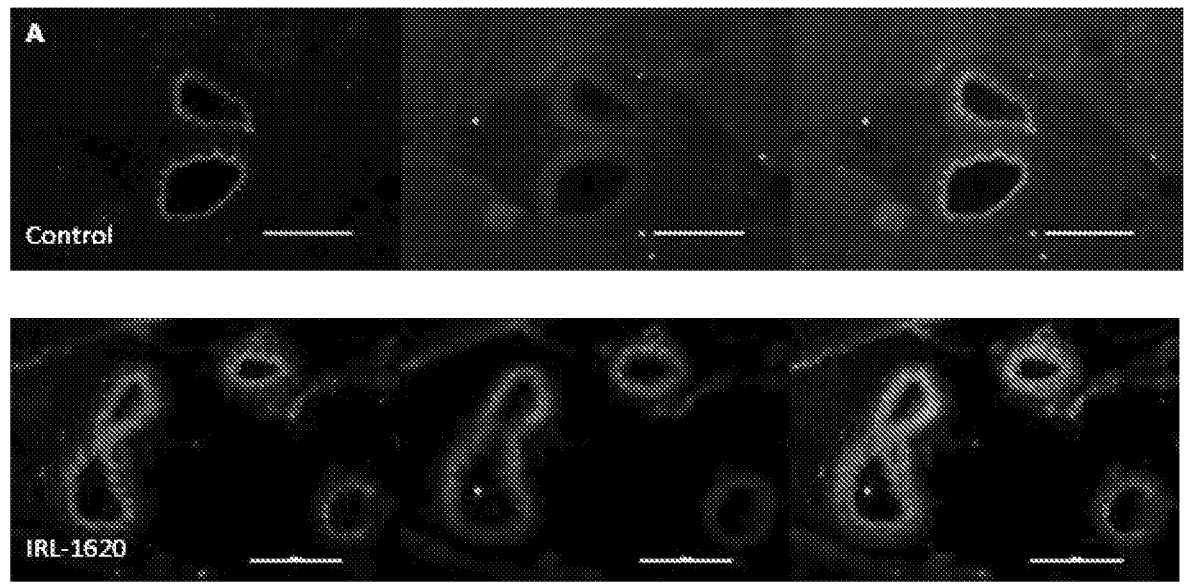
FIG. 4. Effect of $ET_B$ receptor agonist, IRL-1620, on vascular endothelial growth factor and $ET_B$ expression in the postnatal rat brain. Rat pups were administered either saline (control; N=5) or IRL-1620 (5 µg/kg, IV; N=5) on postnatal day 21. Pups were then sacrificed on postnatal day 28 and brains removed for analysis. A) Representative images of blood vessels in the control and IRL-1620-treated rat cortex at postnatal day 28, stained for VEGF (red) and $ET_B$ receptors (green). Scale bar=10 µm. B) Intensity of VEGF in the rat brain vasculature at postnatal day 28. C) Number of VEGF-positive vessels per 20 µm-thick rat brain slice at postnatal day 28. D) Intensity of $ET_B$ receptors in the rat brain vasculature at postnatal day 28. *$P<0.05$ vs. Control. Values are expressed as mean±SEM.
Figure 4B:
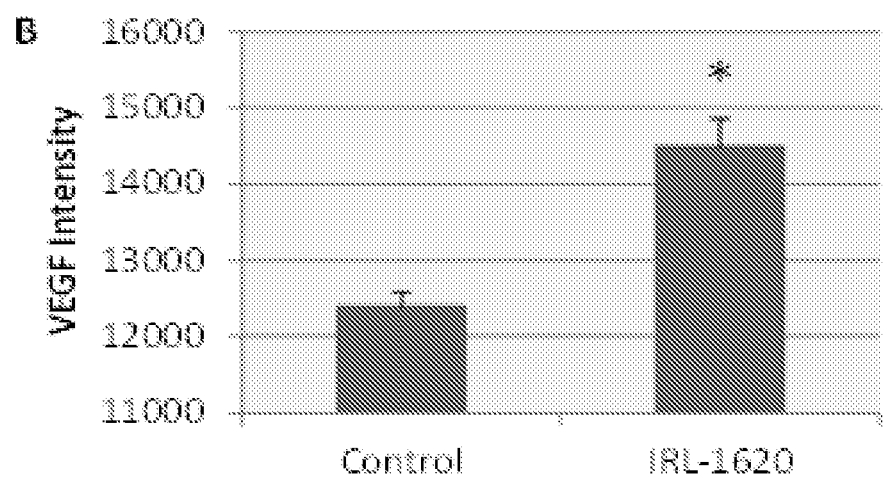
Figure 4C:
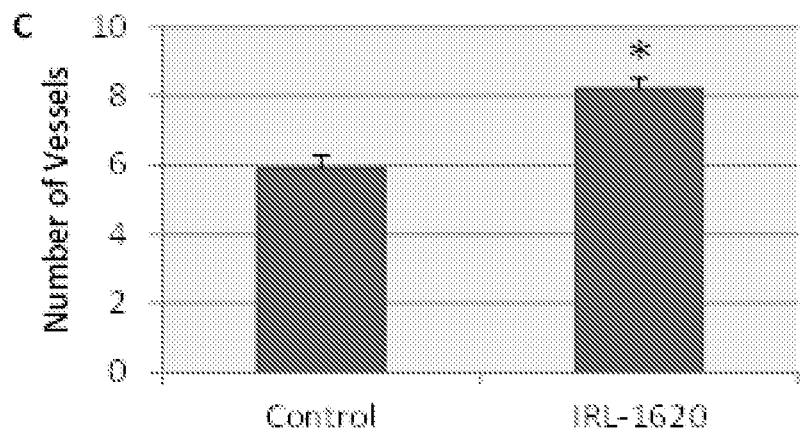
Figure 4D:
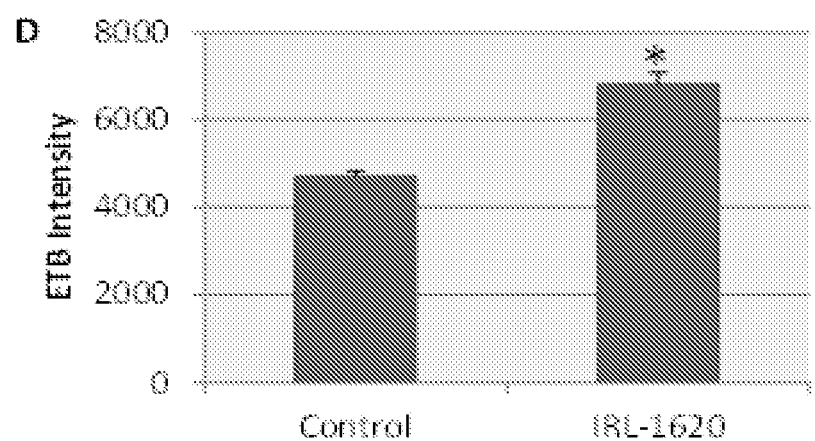
Figure 5A:
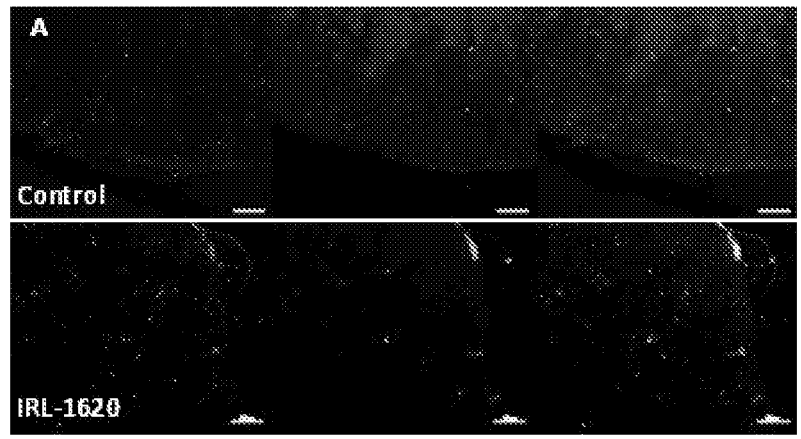
FIG. 5. Effect of $ET_B$ receptor agonist, IRL-1620, on nerve growth factor and $ET_B$ expression in the postnatal rat brain. Rat pups were administered either saline (control; N=5) or IRL-1620 (5 µg/kg, IV; N=5) on postnatal day 21. Pups were then sacrificed on postnatal day 28 and brains removed for analysis. A) Representative images of the cortex of control and IRL-1620-treated rat brains at postnatal day 28, stained for NGF (red) and $ET_B$ receptors (green). Scale bar=100 µm. B) Representative images of the SVZ of control and IRL-1620-treated rat brains at postnatal day 28, stained for NGF (red) and $ET_B$ receptors (green). Scale bar=100 µm. C) Intensity of NGF in the cortex and SVZ of the rat brain at postnatal day 28. D) Number of NGF-positive cells per 100 µm² in the cortex and SVZ of the rat brain at postnatal day 28. E) Intensity of $ET_B$ receptors in the cortex and SVZ of the rat brain at postnatal day 28. *P<0.05 vs. Control. Values are expressed as mean±SEM.
Figure 5B:
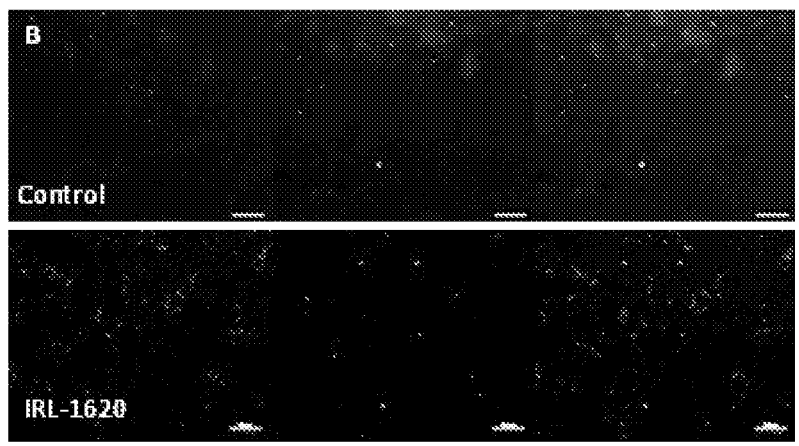
Figure 5C:
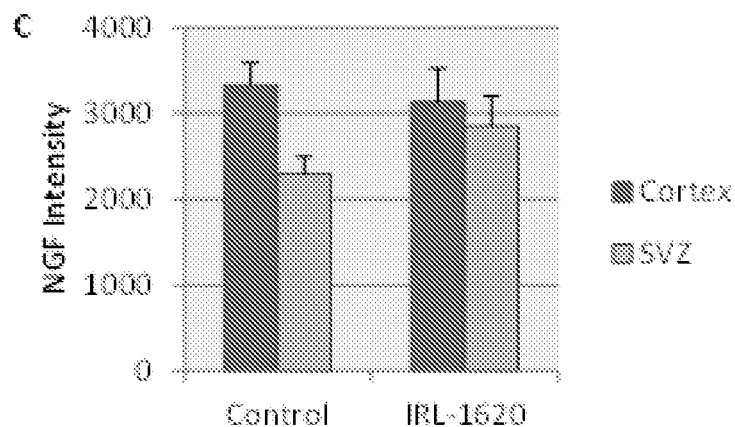
Figure 5D:
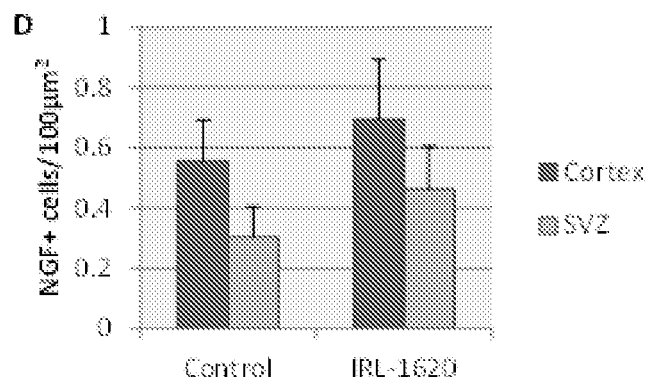
Figure 5E:
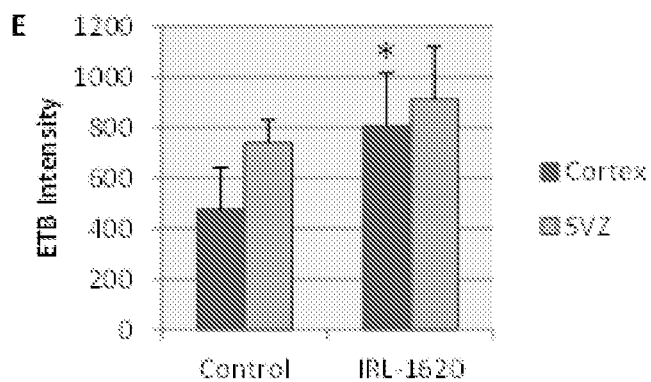
Figure 6A:
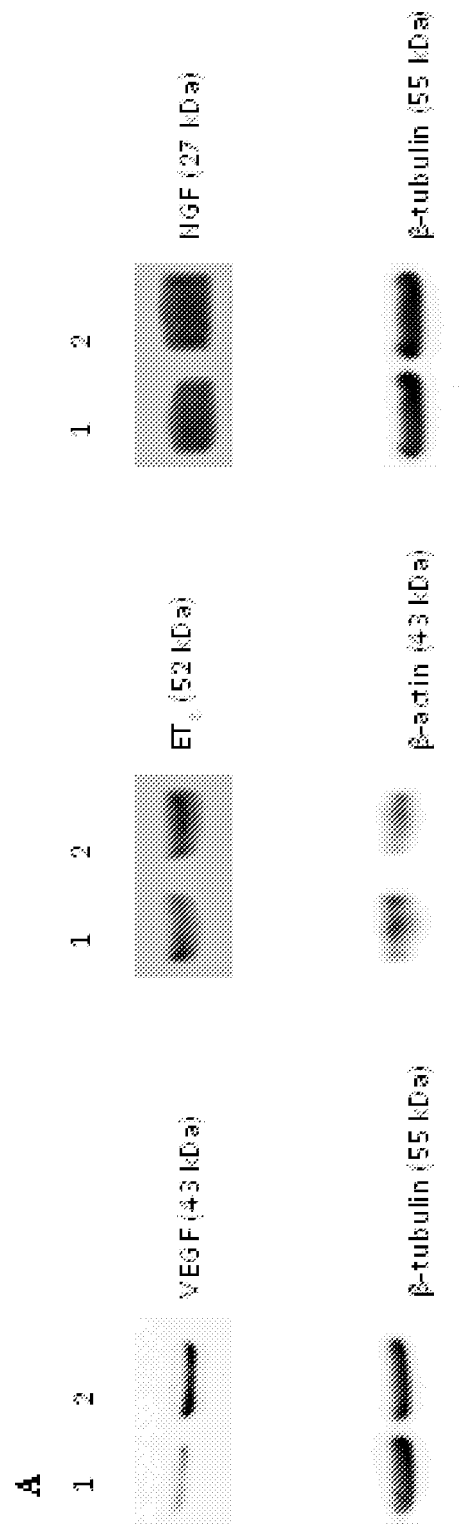
FIG. 6. Effect of $ET_B$ receptor agonist, IRL-1620, on protein levels of vascular growth factor, nerve growth factor and $ET_B$ receptors in the postnatal rat brain. Rat pups were administered either saline (control; N=5) or IRL-1620 (5 µg/kg, IV; N=5) on postnatal day 21. Pups were then sacrificed on postnatal day 28 and brains removed for analysis. A) Representative blots of VEGF, $ET_B$ and NGF protein expression in the control and IRL-1620 treated rat brains at postnatal day 28 with either β-tubulin or β-actin as protein loading controls. Lane 1=Control; Lane 2=IRL-1620. B) Fold change in the expression of VEGF in the rat brain at postnatal day 28. C) Fold change in the expression of $ET_B$ receptors in the rat brain at postnatal day 28. D) Fold change in the expression of NGF in the rat brain at postnatal day 28. *P<0.05 vs. Control. Values are expressed as mean±SEM.
Figure 6B:
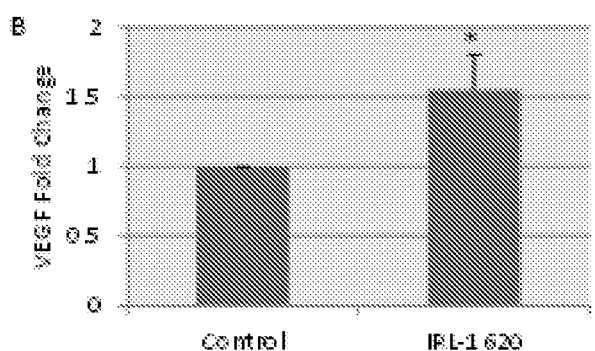
Figure 6C:
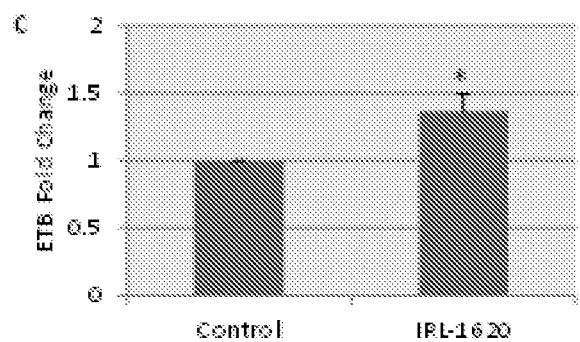
Figure 6D:
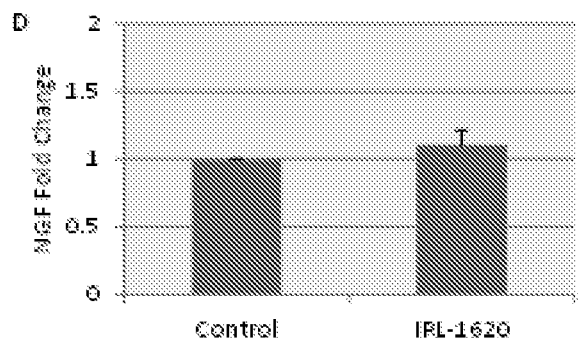

The present disclosure provides compositions and methods for treating a neuropsychiatric disorder. It is disclosed herein that an endothelin-B receptor agonist functions as neuroprotective and a neuroregenerative agent. The compositions and methods of the disclosure generally relate to administering an endothelin-B receptor agonist to a patient in need thereof to treat a neuropsychiatric disorder.

Accordingly, in one aspect the disclosure provides a method of treating a neuropsychiatric disorder comprising administering to a patient in need thereof a therapeutically effective amount of an endothelin-B receptor agonist to treat the neuropsychiatric disorder.

In some embodiments, the endothelin-B receptor agonist is selected from the group consisting of IRL-1620, BQ-3020, [Ala$^{1,3,11,15}$]-Endothelin, Sarafotoxin S6c, endothelin-3, and a mixture thereof.

In some embodiments, the present disclosure contemplates that $ET_B$ receptor agonists such as IRL-1620 (FIG. 1) can be used to treat various neuropsychiatric disorders such as cerebrovascular diseases, stroke, cerebral ischemia, cerebral hemorrhage, head trauma, brain injury, brain tumors, multiple sclerosis and demyelinating diseases, dementia, vascular dementia, Alzheimer's disease, Parkinson's disease, Huntington's disease, ataxias, motor neuron disease, Amyotrophic lateral sclerosis, drug intoxication, alcoholism, chronic brain infections, brain abscess, white matter disease, Binswanger's disease, Moyamoya disease, perinatal hypoxia, cerebral asphyxia, intracranial birth injury, congenital malformation of the brain, mood disorders, and depression.

In some embodiments, the endothelin-B receptor agonist is co-administered with an additional agent to treat the neuropsychiatric disorder. In some embodiments, the additional agent is selected from the group consisting of an antidepressant, an anti-inflammatory agent, a CNS stimulant, a neuroleptic, and an anti-proliferative agent.

General Additional Agents

Examples of antidepressants, CNS stimulants and neuroleptic agents useful in the methods and compositions of the disclosure include, but are not limited to Abilify, Adapin, Adderall, Alepam, Alertec, Aloperidin, Alplax, Alprax, Alprazolam, Alviz, Alzolam, Amantadine, Ambien, Amisulpride, Amitriptyline, Amoxapine, Amfebutamone, Anafranil, Anatensol, Ansial, Ansiced, Antabus, Antabuse, Antideprin, Anxiron, Apo-Alpraz, Apo-Primidone, Apo-Sertral, Aponal, Apozepam, Aripiprazole, Aropax, Artane, Asendin, Asendis, Asentra, Ativan, Atomoxetine, Aurorix, Aventyl, Axoren, Baclofen, Beneficat, Benperidol, Bimaran, Bioperidolo, Biston, Brotopon, Bespar, Bupropion, Buspar, Buspimen, Buspinol, Buspirone, Buspisal, Cabaser, Cabergoline, Calepsin, Calcium carbonate, Calcium carbimide, Calmax, Carbamazepine, Carbatrol, Carbolith, Celexa, Chloraldurat, Chloralhydrat, Chlordiazepoxide, Chlorpromazine, Cibalith-S, Cipralex, Citalopram, Clomipramine, Clonazepam, Clozapine, Clozaril, Concerta, Constan, Convulex, Cylert, Cymbalta, Dapotum, Daquiran, Daytrana, Defanyl, Dalmane, Damixane, Demolox, Depad, Depakene, Depakote, Depixol, Desyrel, Dostinex, dextroamphetamine, Dexedrine, Diazepam, Didrex, Divalproex, Dogmatyl, Dolophine, Droperidol, Desoxyn, Edronax, Effectin, Effexor (Efexor), Eglonyl, Einalon S, Elavil, Elontril, Endep, Epanutin, Epitol, Equetro, Escitalopram, Eskalith, Eskazinyl, Eskazine, Etrafon, Eukystol, Eunerpan, Faverin, Fazaclo, Fevarin, Finlepsin, Fludecate, Flunanthate, Fluoxetine, Fluphenazine, Flurazepam, Fluspirilene, Fluvoxamine, Focalin, Gabapentin,Geodon, Gladem, Glianimon,Guanfacine, Halcion, Halomonth, Haldol, Haloperidol, Halosten, Imap, Imipramine, Imovane, Janimine, Jatroneural, Kalma, Keselan, Klonopin, Lamotrigine, Largactil, Levomepromazine, Levoprome, Leponex, Lexapro, Libotryp Libritabs, Librium, Linton, Liskantin, Lithane, Lithium, Lithizine, Lithobid, Lithonate, Lithotabs, Lorazepam, Loxapac, Loxapine, Loxitane, Ludiomil, Lunesta, Lustral, Luvox, Lyrica, Lyogen, Manegan, Manerix, Maprotiline, Mellaril, Melleretten, Melleril, Melneurin, Melperone, Meresa, Mesoridazine, Metadate, Methamphetamine, Methotrimeprazine, Methylin, Methylphenidate, Minitran, Mirapex, Mirapexine, Moclobemide, Modafinil, Modalina, Modecate, Moditen, Molipaxin, Moxadil, Murelax, Myidone, Mylepsinum, Mysoline, Nardil, Narol, Navane, Nefazodone, Neoperidol, Neurontin, Nipolept, Norebox, Normison, Norpramine, Nortriptyline, Novodorm, Nitrazepam, Olanzapine, Omca, Oprymea, Orap, Oxazepam, Pamelor, Parnate, Paroxetine, Paxil, Peluces, Pemoline, Pergolide, Permax, Permitil, Perphenazine, Pertofrane, Phenelzine, Phenytoin, Pimozide, Piportil, Pipotiazine, Pragmarel, Pramipexole, Pregabalin, Primidone, Prolift, Prolixin, Promethazine, Prothipendyl, Protriptyline, Provigil, Prozac, Prysoline, Psymion, Quetiapine, Ralozam, Reboxetine, Redeptin, Resimatil, Restoril, Restyl, Rhotrimine, riluzole, Risperdal, Risperidone, Rispolept, Ritalin, Rivotril, Rubifen, Rozerem, Sediten, Seduxen, Selecten, Serax, Serenace, Serepax, Serenase, Serentil, Seresta, Serlain, Serlift, Seroquel, Seroxat, Sertan, Sertraline, Serzone, Sevinol, Sideril, Sifrol, Sigaperidol, Sinequan, Sinqualone, Sinquan, Sirtal, Solanax, Solian, Solvex, Songar, Stazepin, Stelazine, Stilnox, Stimuloton, Strattera, Sulpiride, Sulpiride Ratiopharm, Sulpiride Neurazpharm, Surmontil, Symbyax, Symmetrel, Tafil, Tavor, Taxagon, Tegretol, Telesmin, Temazepam, Temesta, Temposil, Terfluzine, Thioridazine, Thiothixene, Thombran, Thorazine, Timonil, tissue plasminogen activator (tPA), Tofranil, Tradon, Tramadol, Tramal, Trancin, Tranax, Trankimazin, Tranquinal, Tranylcypromine, Trazalon, Trazodone, Trazonil, Trialodine, Trevilor, Triazolam, Trifluoperazine, Trihexane, Trihexyphenidyl, Trilafon, Trimipramine, Triptil, Trittico, Troxal, Tryptanol,Tryptomer, Ultram, Valium, Valproate, Valproic acid, Valrelease, Vasiprax, Venlafaxine, Vestra, Vigicer, Vivactil, Wellbutrin, Xanax, Xanor, Xydep, Zaleplon, Zamhexal, Zeldox, Zimovane, Zispin, Ziprasidone, Zolarem, Zoldac, Zoloft, Zolpidem, Zonalon, Zopiclone, Zotepine, Zydis, and Zyprexa.

Anti-Inflammatory Agents

Any agents having anti-inflammatory effects can be used in the present invention. The anti-inflammatory agent can be a steroidal anti-inflammatory agent, a nonsteroidal anti-inflammatory agent, or a combination thereof. In some embodiments, anti-inflammatory agents include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofenac, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Anti-Proliferative Agents

Any agents having anti-proliferative effects can be used in the present invention. The anti-proliferative agent can be a natural proteineous agent such as a cytotoxin or a synthetic molecule. In some embodiments, the active agents include antiproliferative substances such as actinomycin D, or derivatives and analogs thereof (synonyms of actinomycin D include dactinomycin, actinomycin IV, actinomycin $I_1$, actinomycin $X_1$, and actinomycin CO, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, prodrugs thereof, co-drugs thereof, and combinations thereof). Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N-1-tetrazolyl)-rapamycin (ABT-578 manufactured by Abbot Laboratories, Abbot Park, Ill.), prodrugs thereof, co-drugs thereof, and combinations thereof.

The present disclosure contemplates that in further embodiments, the neuropsychiatric disorder is selected from the group consisting of a cerebrovascular disease, stroke, cerebral ischemia, cerebral hemorrhage, head trauma, brain injury, a brain tumor, multiple sclerosis and demyelinating diseases, dementia, vascular dementia, Alzheimer's disease, Parkinson's disease, Huntington's disease, ataxia, motor neuron disease, Amyotrophic lateral sclerosis, drug intoxication, alcoholism, chronic brain infections, brain abscess, white matter disease, Binswanger's disease, Moyamoya disease, perinatal hypoxia, cerebral asphyxia, intracranial birth injury, congenital malformation of the brain, mood disorders, and depression.

According to the disclosure, the endothelin-B receptor agonist may be administered at a dose ranging from 0.0001 to 0.5 mg/kg. In further embodiments, the endothelin-B receptor agonist is administered at a dose ranging from about 0.0001 to about 0.5 mg/kg, or from about 0.0001 to about 0.4 mg/kg, or from about 0.0001 to about 0.3 mg/kg, or from about 0.0001 to about 0.2 mg/kg, or from about 0.0001 to about 0.1 mg/kg, or from about 0.001 to about 0.5 mg/kg, or from about 0.001 to about 0.4 mg/kg, or from about 0.001 to about 0.3 mg/kg, or from about 0.001 to about 0.2 mg/kg, or from about 0.001 to about 0.1 mg/kg, or from about 0.01 to about 0.5 mg/kg, or from about 0.01 to about 0.4 mg/kg, or from about 0.01 to about 0.3 mg/kg, or from about 0.01 to about 0.2 mg/kg, or from about 0.01 to about 0.1 mg/kg, or from about 0.0005 to about 0.5 mg/kg, or from about 0.0005 to about 0.4 mg/kg, or from about 0.0005 to about 0.3 mg/kg, or from about 0.0005 to about 0.2 mg/kg, or from about 0.0005 to about 0.1 mg/kg. In additional embodiments, the endothelin-B receptor agonist is administered at a dose of at least about 0.0001 mg/kg, or at least about 0.0002 mg/kg, or at least about 0.0005 mg/kg, or at least about 0.001 mg/kg, or at least about 0.002 mg/kg, or at least about 0.005 mg/kg, or at least about 0.007 mg/kg, or at least about 0.01 mg/kg, or at least about 0.02 mg/kg, or at least about 0.03 mg/kg, or at least about 0.04 mg/kg, or at least about 0.05 mg/kg, or at least about 0.06 mg/kg, or at least about 0.07 mg/kg, or at least about 0.08 mg/kg, or at least about 0.09 mg/kg, or at least about 0.1 mg/kg, or at least about 0.2 mg/kg, or at least about 0.3 mg/kg, or at least about 0.4 mg/kg. In still further embodiments, the endothelin-B receptor agonist is administered at a dose of less than about 0.0001 mg/kg, or less than about 0.0002 mg/kg, or less than about 0.0005 mg/kg, or less than about 0.001 mg/kg, or less than about 0.002 mg/kg, or less than about 0.005 mg/kg, or less than about 0.007 mg/kg, or less than about 0.01 mg/kg, or less than about 0.02 mg/kg, or less than about 0.03 mg/kg, or less than about 0.04 mg/kg, or less than about 0.05 mg/kg, or less than about 0.06 mg/kg, or less than about 0.07 mg/kg, or less than about 0.08 mg/kg, or less than about 0.09 mg/kg, or less than about 0.1 mg/kg, or less than about 0.2 mg/kg, or less than about 0.3 mg/kg, or less than about 0.4 mg/kg, or less than about 0.5 mg/kg.

The endothelin-B receptor agonist, in various embodiments, is administered to a patient repeatedly at intervals of 1 to 6 hours. In some embodiments, the endothelin-B receptor agonist is administered to the patient every 1 to 5 hours, or every 1to 4 hours, or every 1 to 2 hours, or every hour, or every 2 hours, or every 3 hours, or every 4 hours, or every 5 hours, or every 6 hours. In further embodiments, the endothelin-B receptor agonist is administered to the patient every two to five days, or every three to five days, or every two days, or every three days, or every four days, or every five days.

Endothelin B Receptor Ontogeny in the Postnatal Rat Brain

A decrease in expression of $ET_B$ receptors in the brain of rat pups at postnatal day 28 as measured using immunoblotting technique has been reported (Briyal et al., 2012b). In order to determine the location of these receptors and their potential correlation with vascular and neural growth factors in the developing brain, the brains were immunofluorescently labeled of rat pups at postnatal days 1, 7, 14 and 28 with antibodies for $ET_B$ receptors, VEGF and NGF. The intensity of $ET_B$ receptor staining within the vasculature was significantly higher on day 14 compared to day 1 and day 7 of postnatal age (FIG. 2). In contrast, intensity of $ET_B$ staining in the cortex and subventricular zones of developing rat brain decreased significantly at day 14 of postnatal age compared to day 1 and day 7 (P<0.0001; FIG. 3). $ET_B$ intensity was found to be similar at postnatal age of 14 and 28 days. These results indicate that there is indeed a decrease in the expression of $ET_B$ receptors within the neural tissue of the developing rat brain, but not in the neurovasculature.

Vascular Endothelial Growth Factor Ontogeny in the Postnatal Rat Brain

VEGF in the vasculature of the postnatal rat brain was evaluated at day 1, 7, 14 and 28 of postnatal age via immunofluorescent labeling. As illustrated in FIG. 2, the intensity of VEGF staining in the neurovasculature steadily increased from postnatal days 1 through 14. Similarly, the number of VEGF-positive vessels per 20 μm-thick brain slice significantly (P<0.0001) increased from 2.22±0.36 on day 1 to 5.69±0.74 on day 14 of postnatal age (FIG. 2). While both VEGF and $ET_B$ intensity and expression within the cerebral vasculature of the developing rat brain increased with age, there was no significant correlation between the two ($r^2$=0.8279; P=0.0901).

Nerve Growth Factor Ontogeny in the Postnatal Rat Brain

Immunofluorescent labeling was used to determine the expression and distribution of NGF in the postnatal rat brain at days 1, 7, 14 and 28. The intensity of staining for NGF in the cortex of the developing rat brain significantly decreased from day 1 to day 7 (P<0.001) and again from day 7 to day 14 (P<0.01) of postnatal age. There was no significant difference in NGF intensity from postnatal day 14 to day 28 (FIG. 3). NGF intensity within the subventricular zone of the postnatal rat brain decreased between days 7 and 14 (P<0.01), with no further decline between days 14 and 28 (FIG. 3) of postnatal age. Interestingly, average number of cells staining positive for NGF did not significantly alter during the course of experiment in either the cortex or SVZ. There was, however, a significant correlation between a decrease in $ET_B$ receptors and NGF in the cortex of the developing rat brain with age ($r^2$=0.9742; P=0.0130). These results indicate that, as the rat brain matures the overall expression of NGF declines. This decrease may be correlated with the drop in $ET_B$ receptors within the neuronal tissue.

Effect of IRL-1620 on Endothelin B Receptors in the Postnatal Rat Brain

Administration of $ET_B$ receptor agonist, IRL-1620, on postnatal day 21 resulted in a significant increase in $ET_B$ receptors in the 28-day old rat brain as compared to the control group. Overall, protein expression of $ET_B$ receptors, as measured using immunoblotting technique, increased in the animals who had received IRL-1620 (FIG. 6). Upon immunofluorescent labeling of the brain slices, it was found that intensity of $ET_B$ receptor staining was significantly higher in both the cerebral vasculature (FIG. 2) and the cortex (FIG. 3) of IRL-1620-treated animals as compared to control (P<0.05). These results suggest that selective stimulation of $ET_B$ receptors during neonatal development may result in an upregulation of these receptors.

Effect of IRL-1620 on Vascular Endothelial Growth Factor in the Postnatal Rat Brain As seen in FIG. 2, VEGF increases in the cerebral vasculature throughout development in rats. Selective stimulation of $ET_B$ receptors using agonist IRL-1620 leads to a further increase in both the intensity of VEGF staining and the number of VEGF-positive vessels (P<0.05; FIG. 4) within the postnatal rat brain when compared to control animals of the same age. These results were confirmed using immunoblotting technique showing that overall VEGF expression is significantly enhanced within the postnatal brains of rats treated with IRL-1620 (P<0.05; FIG. 6). These findings suggest that selective stimulation of $ET_B$ receptors during development enhances cerebrovascular angiogenesis.

Effect of IRL-1620 on Nerve Growth Factor in the Postnatal Rat Brain

Immunofluorescent labeling of NGF significantly diminishes by postnatal day 14 in the rat brain. Administration of $ET_B$ receptor agonist, IRL-1620, on postnatal day 21 did not alter either intensity of NGF staining nor number of NGF-positive cells within the cortex or subventricular zones of rats as compared to control (FIG. 5). Similarly, overall expression of NGF within the postnatal rat brain as measured via immunoblotting technique was comparable in both control and treated groups (FIG. 6). Selective $ET_B$ receptor stimulation does not appear to have any significant effect on NGF levels within the rat brain during postnatal development.

Experimental Procedure

Animals

Timed pregnant female Sprague-Dawley rats (Harlan, Indianapolis, Ind.) were caged singly in a room controlled for ambient temperature (23±1° C.), humidity (50±10%) and a 12 h light/dark cycle (6:00 am-6:00 pm). Food and water were available ad libitum. All animal care and use for procedures were approved by the Institutional Animal Care and Use Committee (IACUC) of Midwestern University. In order to avoid variation due to hormonal changes, male pups only were separated and utilized for this study. The pups were euthanized via decapitation on postnatal day 1, 7, 14 and 28. The brains were aseptically removed and processed for either immunofluorescent labeling or immunoblot analysis of $ET_B$ receptors, VEGF and NGF.

Study Design and Agent Administration

After 21 days of gestation, 70 male and 65 female pups were born to 10 pregnant female rats. 30 male pups were randomly selected for Study I, and divided into 4 groups as follows: Group 1=male pups euthanized on postnatal day 1 (N=10); Group 2=male pups euthanized on postnatal day 7 (N=10); Group 3=male pups euthanized on postnatal day 14 (N=5); Group 4=male pups euthanized on postnatal day 28 (N=5). An additional 20 male pups were randomly selected for Study II, and divided into 2 groups: Control (N=10) and IRL-1620-treated (N=10). Pups in Study II received 3 doses of either isotonic saline (1 ml/kg) or $ET_B$ receptor agonist IRL-1620 (5 µg/kg; American Peptide Co, Inc., Sunnyvale, Calif.) on postnatal day 21. The doses were given intravenously at 2 hour intervals. All pups were weighed and evaluated for developmental and behavioral characteristics at postnatal day 1, 7, 14 and 28. Developmental and behavioral characteristics included active vs. sluggish behavior, healthy vs. shedding fur, licking, grooming, aggressive behavior, defecation, urination and wet dog shakes.

Immunofluorescent Labeling

Immunofluorescently labeled antibodies were used to determine the expression of $ET_B$ receptors, VEGF and NGF in the developing rat brain. Male rat pups were euthanized via decapitation, and the brains were removed at postnatal day 1, 7, 14 and 28. The brains were washed in isotonic saline and transferred to a 4% paraformaldehyde (PFA)/NaPO$_4$ buffer solution for 2 hours to fix the tissue, followed by suspension in a 20% sucrose/4% PFA solution for 48 hours at 4° C. Brains were then sliced into 20 µm thick coronal sections at −30° C. using a cryostat (Microtome cryostat HM 505 E; Walldorf, Germany). Sections were processed for immunofluorescent staining as described by Loo, et al. (Loo et al., 2002), with minor modifications. The primary antibody for $ET_B$ receptors was an anti-$ET_B$ receptor antibody raised in sheep against the carboxy-terminal peptide of the rat $ET_B$ receptor (1:200; ab50658; Abcam, Cambridge, Mass.). Determination of angiogenic and neurogenic markers was performed using antibodies against VEGF (anti-VEGF; 1:500; ab46154; Abcam) and nerve growth factor (anti-NGF; ab6199; Abcam). Sections were washed in PBS and then blocked with 10% v/v serum in PBS containing 0.3% Triton X-100 for 1 h. Sections were then incubated with the primary antibody overnight at 4° C., and again washed with PBS and incubated with the appropriate secondary antibody for 2 h at room temperature. Double labeling for co-localization was performed sequentially. Sections were rinsed with PBS and mounted on glass slides with Vectashield (Vector Laboratories, Inc., Burlingame, Calif.). Fluorescence was detected using an inverted fluorescent microscope (Nikon Eclipse TiE, Melville, N.Y.). All images for analysis were taken with the same exposure (300 msec for VEGF and NGF; 800 msec for $ET_B$) and objective (Plan Fluor 10×Ph1DL) settings with a multichannel ND acquisition using NIS Elements BR imaging software (Nikon Instruments, Inc., Melville, N.Y.).

Immunofluorescent Analysis

Analyses for NGF were performed specifically in the cortex and SVZ of the rat brain. Overlaying a grid of 100×100 µm squares on each image, the number of cells staining positively for NGF was determined in six randomly selected, non-congruent 100 µm$^2$ sections per brain slice in each area. All cells falling at least 50% inside the 100 µm$^2$ area were counted. For the evaluation of angiogenesis, the total number of VEGF-positive blood vessels was determined per brain slice. Fluorescent intensity for each marker was measured using the unaltered images with NIS Elements BR imaging software (Nikon Instruments, Inc., Melville, N.Y.).

Immunoblotting

Protein levels of VEGF, NGF and $ET_B$ receptors in the postnatal rat brain of animals in Study II were estimated using immunoblotting technique. Animals were decapitated and the brains were removed on postnatal day 28, which is 7 days post administration of either saline or $ET_B$ receptor agonist, IRL-1620. The tissue was homogenized in 10× (w/v) RIPA lysis buffer, and protein concentration was determined according to the Lowry method, using bovine serum albumin as standard (Lowry et al., 1951). Protein (60 µg) was denatured in Laemmli sample buffer and resolved in 10% SDS-PAGE, and then transferred onto nitrocellulose membrane. After blocking, the membranes were incubated with rabbit polyclonal anti-VEGF (1:1000; Abcam, Cambridge, Mass.), anti-NGF (1:500; Abcam, Cambridge, Mass.), or anti-$ET_B$ (1:1000; Sigma-Aldrich) antibodies overnight at 4° C., followed by 1.5 hours incubation with by HRP-conjugated secondary antibodies (1:2000; Cell Signaling Technology, Inc., MA) at room temperature. β-tubulin (1:2000; Cell Signaling Technology, Inc. MA) or β-actin (1:10000; Sigma-Aldrich) were used as loading controls. The labeled proteins were visualized with SuperSignal West Pico Chemiluminescent Substrate (Thermo Scientific) using the Kodak Gel Logic 1500 Imaging System (Carestream Health Inc., New Haven, Conn.). Protein expression was analyzed using Image J (NIH) software.

Statistical Analysis

A power analysis was conducted using GraphPad Instat-2.00. The power was set to 80% (beta=0.8) and the level of significance (alpha) used was 0.05. The power analysis indicated that a sample size of 5 per group was sufficient to achieve the desired power. Data are presented as mean±S.E.M. One-way analysis of variance (ANOVA) followed by Tukey's post-hoc comparison test was used for intergroup comparison. Unpaired t-test was used for comparison of postnatal day 28 control vs. IRL-1620 groups. A P value of less than 0.05 was considered to be significant. The statistical analysis was processed using GraphPad Prism 6.02 (GraphPad, San Diego, Calif.).

The goal of the present study was to determine the ontogeny of $ET_B$ receptors, VEGF and NGF in the postnatal rat brain, as well as to investigate whether or not selective stimulation of $ET_B$ receptors during postnatal development would result in changes in the expression of either the receptors or growth factors. In confirmation of previous studies (Briyal et al., 2012b), it was found that $ET_B$ receptors appear to decrease in the neuronal tissue with postnatal age. Interestingly, both $ET_B$ receptor and VEGF intensity increased within the cerebral vasculature from postnatal day 1 to day 14. NGF, on the other hand, decreased concurrently with $ET_B$ receptors in the cortex and SVZ of the rat brain from postnatal day 1 to day 14. Selective stimulation of $ET_B$ receptors via intravenous IRL-1620 on postnatal day 21 led to a significant increase in $ET_B$ receptors and VEGF, but not NGF. These results suggest that, while the ontogeny of $ET_B$ receptors may be related to both vascular and neuronal growth factors within the developing brain, stimulation of $ET_B$ receptors during postnatal development exerts more influence over angiogenesis than neurogenesis.

While the rat model is commonly used in ontological studies, it is important to recognize that gestation and development, particularly with regards to the brain, differ between rodents and humans. It has been reported that 16.7 rat days are equivalent to 1 human year (Quinn, 2005). Extrapolating this information out onto the timeline of the present study provides the following information: postnatal day 1=21 human days; postnatal day 7=5 human months; postnatal day 14=10 human months; and postnatal day 28=20 human months. This is significant as rapid brain growth for the human begins at the end of the second trimester, peaks at birth and then decreases over the next several years. Rats, however, with a gestational period of only 21 days, experience the most rapid rise in brain growth and development within the first 10 postnatal days (Gil-Mohapel et al., 2010). This period is roughly equivalent to the third trimester in human brain development.

The period of time evaluated by the present study, postnatal rat days 1 to 28, coincide with the first 2 years of equivalent human brain development. As expected, the highest levels of neuronal growth factor along with $ET_B$ receptors were noted in the cortex and SVZ on the first day following birth. These levels decreased significantly with increasing brain maturity from day 1 to day 14. No significant change was noted between days 14 and 28. A decrease in $ET_B$ receptor protein expression with the whole rat brain by postnatal day 21 has been reported (Briyal et al., 2012b). The present data shed light on earlier reports of low levels of neuronal progenitors and increased CNS disturbances in $ET_B$ deficient rat pups (Ehrenreich et al., 2000; Riechers et al., 2004; Vidovic et al., 2008). A significant co-relation was found between the declines in intensity of NGF and $ET_B$ receptor staining in the cerebral cortex of developing brain; however, when IRL-1620 was administered on postnatal day 21, to stimulate $ET_B$ receptors, this co-relation was lost and an increase in $ET_B$ receptor staining was not accompanied with an increase in NGF staining in the cerebral cortex. It is possible that there is a regulatory mechanism that initiates a decrease in $ET_B$ receptor and NGF staining as the brain matures and this regulatory mechanism does not allow IRL-1620 to produce any pharmacologically induced increase in $ET_B$ receptor and NGF staining of the brain that is close to maturity.

$ET_B$ receptor stimulation, therefore, does not appear to increase neurogenesis during late-stage CNS development, although it has been shown to enhance this process during adult neurovascular repair processes (Leonard and Gulati, 2013) indicating a loss of regulatory mechanism following cerebral ischemia. Selective stimulation of $ET_B$ receptors did, however increase the overall expression of $ET_B$ within the whole brain as measured via immunoblotting technique as well as the intensity of $ET_B$ receptor staining of the cerebral vasculature of the developing rat brain, suggesting that such stimulation does enhance angiogenesis during the late postnatal period.

Overall, both VEGF and $ET_B$ intensity within the cerebral vasculature increased throughout the period studied. VEGF is a potent angiogenic factor essential for CNS vascularization, development and repair. Previous research has indicated the VEGF is restricted mainly to cortical neurons early in development, but then switches to maturing glial cells around the blood vessels as the vascular bed begins to stabilize (Ogunshola et al., 2000). While VEGF expression within the neuronal tissue was not specifically determined, the results demonstrate an increase in VEGF around the vasculature as the brain develops. In the earlier stages of CNS development, when NGF levels are high, VEGF may serve as a promoter of neurogenesis, neuronal migration and neuroprotection (Rosenstein et al., 2010). Similar effects are seen in the adult brain following ischemic injury, with increased levels of VEGF promoting cerebrovascular repair (Gora-Kupilas and Josko, 2005; Nowacka and Obuchowicz, 2012). Indeed, previous studies have shown that selective stimulation of $ET_B$ receptors following permanent cerebral ischemia leads to an increase in both VEGF and $ET_B$ expression, coincident with neuroprotection and cerebrovascular repair (Leonard and Gulati, 2013). In the present study, selective stimulation of $ET_B$ receptors at postnatal day 21 resulted in increases in VEGF and $ET_B$ expression both in the cerebral vasculature and the whole brain. These results serve to both confirm the relationship between $ET_B$ receptors and VEGF and to highlight their importance in the developing brain.

Hypoxia-ischemia brain damage during the neonatal period is one of the main factors in brain dysfunction (Li et al., 2008). Premature infants, in particular, often experience episodes of hypoxia-ischemia which can lead to reduced cortical growth and development. These impairments may continue through childhood and adolescence, and can cause dysfunction within the neural micro circuitry leading to epilepsy, neurodevelopmental disorders and psychiatric illnesses (Malik et al., 2013). Episodes of hypoxia-ischemia within the brain are known to increase hypoxia-inducible transcription factor-1, which in turn upregulates VEGF (Trollmann et al., 2008). It has been shown that selective $ET_B$ receptor stimulation upregulates both $ET_B$ receptors and VEGF in the brains of both normal neonates and adult rats subjected to cerebral ischemia. It is possible that early treatment with a selective $ET_B$ receptor agonist may enhance VEGF and neuroprotection, thereby enabling the brains of infants suffering from hypoxic damage to repair this neuronal damage.

The present study indicates that selective stimulation of $ET_B$ receptors enhances VEGF within the developing rat brain. While no similar significant upregulation of NGF was noted in the present study, a correlation in the ontogeny of $ET_B$ receptors and NGF was observed within the cortex and SVZ of postnatal rat pups. It appears that both $ET_B$ receptors and NGF are important in the early phase of development of the CNS. As studies have shown that selective $ET_B$ receptor stimulation is capable of enhancing cerebrovascular repair in the adult brain following ischemia, it would be of interest to determine whether or not similar treatment could significantly improve repair mechanisms within the developing brain subjected to ischemia.

Studies in Animal Model of Alzheimer's Disease

Male Sprague-Dawley rats (Harlan, Indianapolis, Ind.) weighing 280-310 g were allowed to acclimate for at least 4 days before use. Animals were housed in a room with controlled temperature (23±1° C.), humidity (50±10%), and light (6:00 A.M. to 6:00 P.M.). Food and water were available continuously. Animal care and use for experimental procedures were approved by the Institutional Animal Care and Use Committee (IACUC) of Midwestern University. All anesthetic and surgical procedures were in compliance with the guidelines established by the IACUC of Midwestern University.

Agents and Experimental Design

Amyloid-β (1-40) (Tocris Bioscience, Ellisville, Mo., USA), IRL-1620 [N-Succinyl-[Glu9, Ala11,15] endothelin 1] (American Peptide Co, Inc., Sunnyvale, Calif., USA) and BQ788 (American Peptide Co, Inc., Sunnyvale, Calif., USA) were dissolved in sterile saline and all the solutions were freshly prepared before injections. Ketamine (Butler Animal Health Supply, Dublin, Ohio, USA) was administered at a dose of 100 mg/kg, intraperitoneally (i.p.), and xylazine (Lloyd Laboratories, Shenandoah, Iowa, USA) was administered at a dose of 10 mg/kg, i.p. Rats were anesthetized with ketamine (100 mg/kg) and xylazine (10 mg/kg) and a lateral cerebral ventricle was cannulated by placing the rat in a stereotaxic (David Kopf Instruments, Tujunga, Calif., USA) instrument and fixing the cannula (coordinates: 1.0 mm lateral, 1.5 mm caudal to bregma and 4.0 mm deep from the bone). Cannula (Plastics One, Roanoke, Va., USA) was anchored with dental acrylic to three screws placed in the skull. The animals were allowed to recover from surgery for at least seven days. After 7 days, rats were treated with vehicle, Aβ (1-40), $ET_B$ receptor agonist and/or antagonist in the lateral cerebral ventricles using the implanted cannula. Vehicle, Aβ or $ET_B$ receptor agonist and antagonist were injected in a volume of 5 μl over a period of 5 minutes. Aβ (1-40) was used because it is highly soluble compared to Aβ (1-42) and induces endothelial dysfunction of both cerebral and systemic blood vessels in addition to memory deficit (Nitta et al., 1994; Niwa et al., 2000; Smith et al., 2004; Weller et al., 1998). Agents were delivered using 10 μl Hamilton syringe and agent treatments were carried out individually using separate 10 μl syringe. IRL-1620 was administered 1 hour after Aβ injection whereas BQ788 was administered 15 minutes prior to IRL-1620 injection. At the end of the experiment, placement of cannula was confirmed by injecting methylene blue dye (5 μl) and observing the site and extent of staining. All experiments were performed on day 15 (Briyal et al., 2011). Water maze testing was performed from day 15 to day 19 after which animals were euthanized. Animals used for oxidative stress measurements were euthanized on day 15 without being subjected to any behavioral testing. Diabetes mellitus type 2 was induced in rats belonging to the diabetic group by administering freshly prepared streptozotocin at the dose of 45 mg/kg, i.p. Streptozotocin was dissolved in 0.01 M sodium citrate buffer of pH 4.3. On day 3, blood glucose was obtained from the rat-tail and tested for hyperglycemia using the SureStep Complete Blood Glucose monitor kit. Rats with blood glucose levels above 11.1 mM were considered diabetic. Diabetic and non-diabetic animals were randomly divided into five groups (6 rats per group) (i) Sham, (ii) Aβ+Vehicle, (iii) Aβ+IRL-1620, (iv) Aβ+BQ788 (v) Aβ+BQ788+IRL-1620. Aβ (1-40) was administered intracerebroventricularly (i.c.v.) (20 μg in 3 equally divided doses i.e. 6.67 μg were injected 3 times for a total of 20 μg dose) on day 1, 7, and 14. Specific $ET_B$ receptor agonist, IRL-1620 (3 μg) and specific $ET_B$ receptor antagonist, BQ788 (10 μg) were administered i.c.v. daily for 14 days starting from day 1 of Aβ injection. The doses of IRL-1620 and BQ788 were selected on the basis of previous studies conducted in our laboratory (Leonard et al., 2011).

Estimation of Oxidative Stress Markers

Malondialdehyde (MDA), reduced glutathione (GSH) and superoxide dismutase (SOD) were estimated on day 15 in the rat brains. Rats were decapitated and the brains quickly removed, cleaned with chilled saline and stored at −80° C. The biochemical analysis was performed within 48 hours.

Measurement of Lipid Peroxidation

MDA, a marker of lipid peroxidation, was measured spectrophotometrically (Ohkawa et al., 1979). Briefly, the whole brain of each animal was removed separately and was homogenized with 10 times (w/v) in 0.1M sodium phosphate buffer (pH 7.4). Acetic acid 1.5 ml (20%), pH 3.5, 1.5 ml thiobarbituric acid (0.8%) and 0.2 ml sodium dodecyl sulfate (8.1%) were added to 0.1 ml of processed tissue sample. The mixture was then heated at 100° C. for 60 minutes. The mixture was cooled, and 5 ml of butanol:pyridine (15:1% v/v) and 1 ml of distilled water were added. After centrifugation at 4,000 rpm for 10 minutes, the organic layer was withdrawn and absorbance was measured at 532 nm using a spectrophotometer.

Measurement of Glutathione

Glutathione was measured spectrophotometrically (Ellman, 1959). Briefly, whole brain was homogenized with 10 times (w/v) 0.1 M sodium phosphate buffer (pH 7.4). This homogenate was then centrifuged with 5% trichloroacetic acid to separate the proteins. To 0.1 ml of supernatant, 2 ml of phosphate buffer (pH 8.4), 0.5 ml of 5'5 dithiobis (2-nitrobenzoic acid) (DTNB) and 0.4 ml of double distilled water was added. The mixture was vortexed and the absorbance read at 412 nm within 15 min.

Measurement of Superoxide Dismutase

SOD was estimated as described by Kakkar et al (Kakkar et al., 1984). Briefly, whole brain was homogenized with 10 times (w/v) 0.1 M sodium phosphate buffer (pH 7.4). The reagents sodium pyrophosphate buffer 1.2 ml (0.052 M) pH 8.3, 0.1 ml phenazine methosulphate (186 μM), 0.3 ml nitro blue tetrazolium (300 μM) and 0.2 ml NADH (780 μM) were added to 0.1 ml of processed tissue sample. The mixture was then incubated for 90 min at 30° C. Then 4 ml of n-butanol and 1 ml of acetic acid were added. The mixture was shaken vigorously. After centrifugation at 4,000 rpm for 10 minutes, the organic layer was withdrawn and absorbance was measured at 560 nm using a spectrophotometer. Protein was estimated using Lowry's method (Lowry et al., 1951).

Morris Water Maze (MWM) Test for Cognitive Impairment

Spatial learning and memory of animals were tested in a MWM (Morris, 1984). A circular water tank (132 cm diameter, 60 cm height, painted white was filled with water (25±2° C.) to a depth of 40 cm, the water was rendered opaque by the addition of non-fat milk. The pool was divided into four equal quadrants, labeled north, south, east, and west. A circular, white escape platform (10 cm in diameter) was submerged approximately 2 cm below the surface of the water, 10 cm off the edge of the tank at a position designated as quadrant II (target quadrant). A video camera was mounted on the ceiling in the center of the pool. The escapes latency and swimming path length was monitored with a Videomex tracking system and data were collected using Videomex Water Maze Software (Columbus Instruments, Ohio, USA).

The platform remained in the same quadrant during the entire acquisition phase experiments and removed in probe trial. Acquisition trials (4 trials per day for 4 days) were started by placing rat in a pool facing the wall of the tank from different randomly chosen start positions, and time required to find the invisible platform was recorded. A trial lasted until the rat found the platform or until 60 seconds had elapsed and an inter-trial interval of approximately 30 seconds. If rat did not find the platform within 60 seconds, it was guided to the platform and placed on it for 60 seconds. Time to reach the platform (latency in seconds) and swimming path length (in centimeters) was measured. After completion of the fourth trial on each day, the rat was dried and returned to its home cage. Twenty four hours after the final acquisition trial, the platform was removed from the pool and a probe trial lasting 60 seconds was performed; the time spent in the target quadrant was recorded. Time spent in the target quadrant indicated the degree of memory consolidation which had taken place after learning.

Statistical Analysis

Results were expressed as Mean±S.E.M. In acquisition trials of Morris water maze following parameters were recorded: escape latency (time required to reach the platform from the releasing point in seconds), and path length (distance traveled by rat from the release point to reach platform in centimeters). Analysis of variance (ANOVA) was conducted on these data, with group as the between-subject factor and with repeated measures such as trial and day as within subject factors. Post hoc analysis (Tukey's test) was used to determine significance between the groups. For probe trial data, time spent in quadrant II were recorded and analyzed by one way ANOVA and post hoc analysis by Bonferroni's test. Oxidative stress measures were analyzed by one way ANOVA followed by post hoc analysis using Bonferroni's test. All analysis was carried out using Graph-Pad Prism Statistical Software, version 5.00 (GraphPad, San Diego, Calif., USA). $P<0.05$ represents level of significance.

Effect of Diabetes Mellitus Type 2 on Rats

Diabetic rats were sluggish and had decreased locomotion as compared to non-diabetic rats. However, diabetic and non-diabetic rats had similar performance in Morris water maze tests (FIG. 8-11). FIG. 7 illustrates that there was no difference in oxidative stress parameters between diabetic and non-diabetic rats.

Effect of $ET_B$ Receptor Agonist and Antagonist on Oxidative Stress Parameters in Aβ-Treated Non-Diabetic and Diabetic Rats To determine the involvement of $ET_B$ receptors in Aβ induced changes in oxidative stress parameters, malondialdehyde, reduced glutathione and superoxide dismutase levels in the brains of sham and Aβ treated rats were measured following administration of vehicle, IRL-1620 or BQ788+ IRL-1620 (FIG. 1).

Effect on Brain Malondialdehyde Levels

Figure 7A:
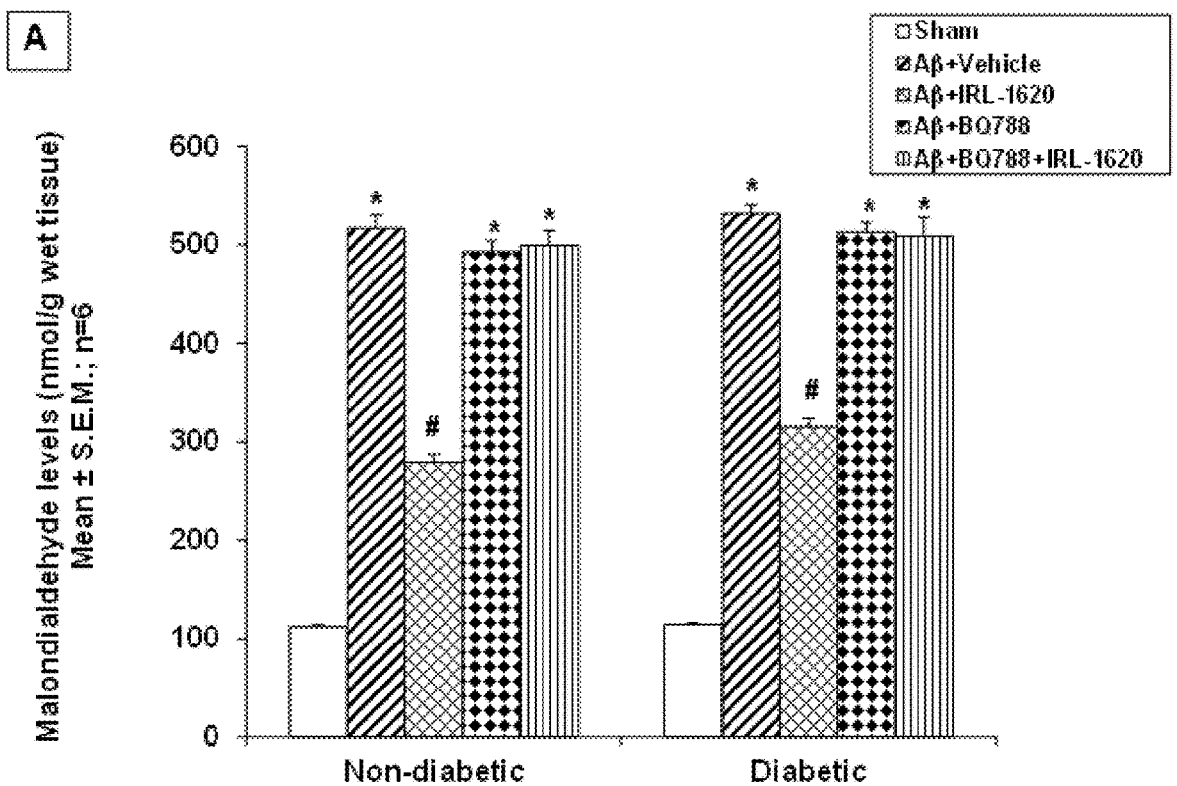
FIG. 7. Effect of an $ET_B$ receptor agonist, IRL-1620, in presence and absence of an $ET_B$ receptor antagonist, BQ788, on malondialdehyde (MDA) (A), reduced glutathione (GSH) (B) and superoxide dismutase (SOD) (C) levels in Aβ induced oxidative stress in the rat brain. Values are expressed as mean±SEM. *p<0.0001 compared to sham; #p<0.001 compared to Aβ+vehicle (N=6).

Brain levels of malondialdehyde (MDA) were measured to determine the effect of $ET_B$ receptor stimulation on lipid peroxidation following Aβ treatment (FIG. 7A). As expected, levels of MDA were significantly ($p<0.0001$) higher in Aβ treated rats for both non-diabetic and diabetic groups compared to sham groups. MDA level for non-diabetic Aβ treated animals was 516.13±14.02 nmol/g wet tissue which was greater compared to sham (112.1±1.84 nmol/g wet tissue) animals. In diabetic rats, MDA level was 531.58±9.02 nmol/g wet tissue in Aβ treated while it was 114.32±2.05 nmol/g wet tissue in sham animals. MDA levels were significantly ($P<0.001$) reduced in IRL-1620 treated rats compared to vehicle treated Aβ rats for both non-diabetic (278.47±8.55 nmol/g wet tissue) and diabetic (315.09±5.25 nmol/g wet tissue) animals. Administration of BQ788 prior to IRL-1620, blocked IRL-1620 induced change in MDA levels and the levels were similar to those seen in vehicle treated rats.

Effect on Brain Reduced Glutathione Levels

Figure 7B:
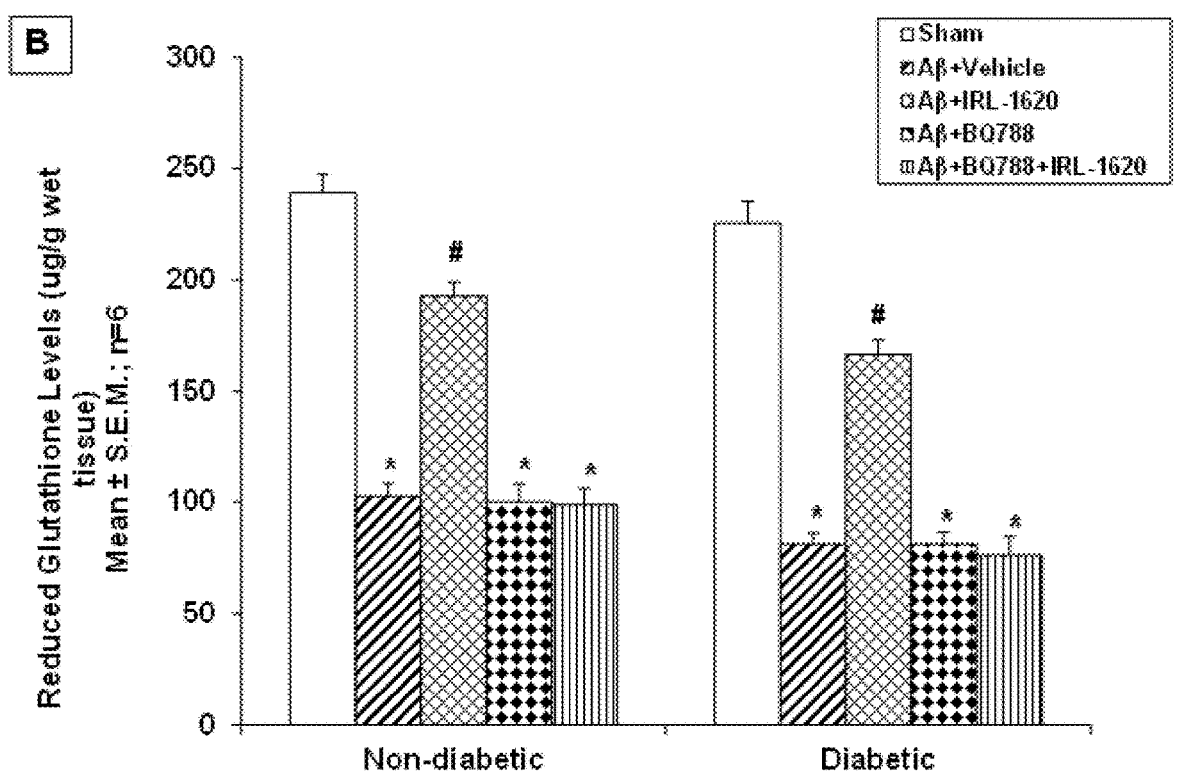

Reduced glutathione (GSH) levels in Aβ treated non-diabetic and diabetic animals were significantly ($P<0.0001$) lower than those of sham operated animals. The mean GSH level for non-diabetic and diabetic Aβ treated groups were 102.5±5.96 and 81.2±4.33 µg/g wet tissue, respectively, while that in sham rats it was 239.1±8.0 µg/g wet tissue. Treatment with IRL-1620 significantly ($P<0.001$) increased levels of GSH in the brains of Aβ treated non-diabetic and diabetic rats (192.74±6.26 and 166.42±6.63 µg/g wet tissue, respectively) (FIG. 7B). Pretreatment with BQ788 blocked the positive effect of IRL-1620 treatment on GSH levels (81.2±5.49 µg/g wet tissue; $P<0.001$).

Effect on Brain Superoxide Dismutase Levels

Figure 7C:
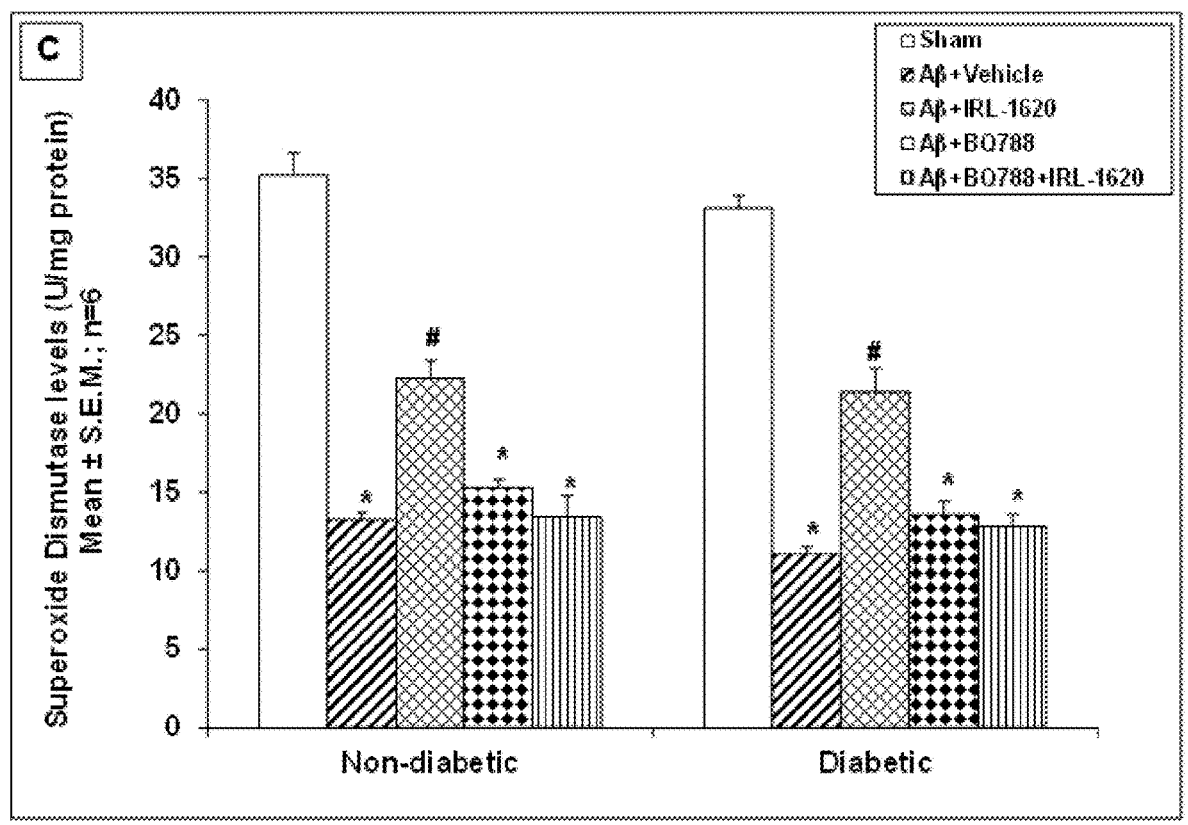

The levels of superoxide dismutase (SOD) in the brains of vehicle treated non-diabetic (13.23±0.53 U/mg protein) and diabetic (11.07±0.54 U/mg protein) Aβ rats were significantly ($P<0.0001$) lower than those of sham operated group (35.22±1.43 U/mg protein). Administration of IRL-1620 significantly improved SOD levels in non-diabetic and diabetic rats (22.26±1.16 and 21.4±1.65 U/mg protein, respectively) (FIG. 7C). Similar to GSH, SOD levels were significantly ($P<0.001$) lower when non-diabetic and diabetic Aβ animals were pretreated with BQ788 prior to IRL-1620 administration (15.32±0.44 and 16.52±0.45 U/mg protein, respectively).

Figure 8A:
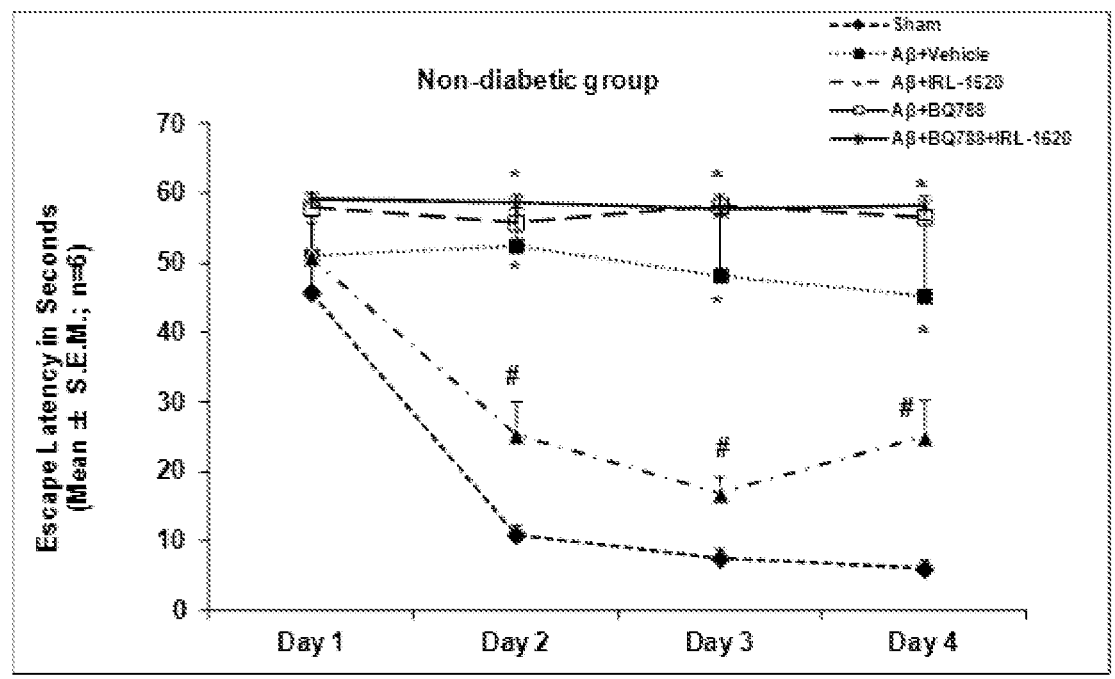
FIG. 8. Effect of an $ET_B$ receptor agonist, IRL-1620, in presence and absence of an $ET_B$ receptor antagonist, BQ788, on the escape latency (A) and path length (B) on each training day of the water maze task in non-diabetic rats. The animals were submitted to four daily trials to find a hidden platform for 4 training days. Values were expressed as mean±S.E.M. *p<0.001 compared to sham; #p<0.001 compared to Aβ+ vehicle (N=6).
Figure 8B:
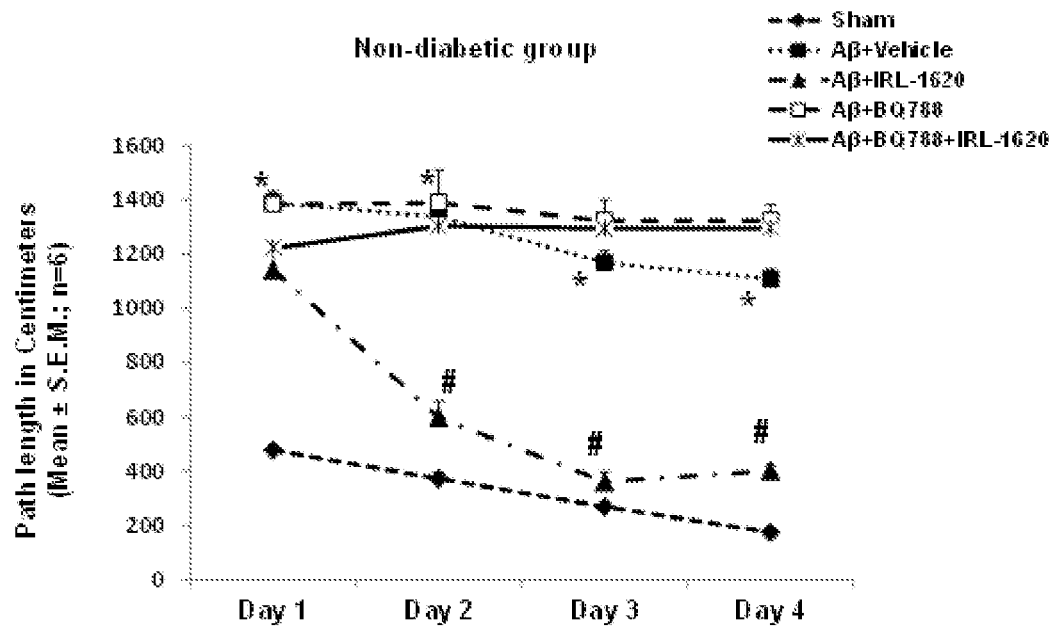
Figure 9A:
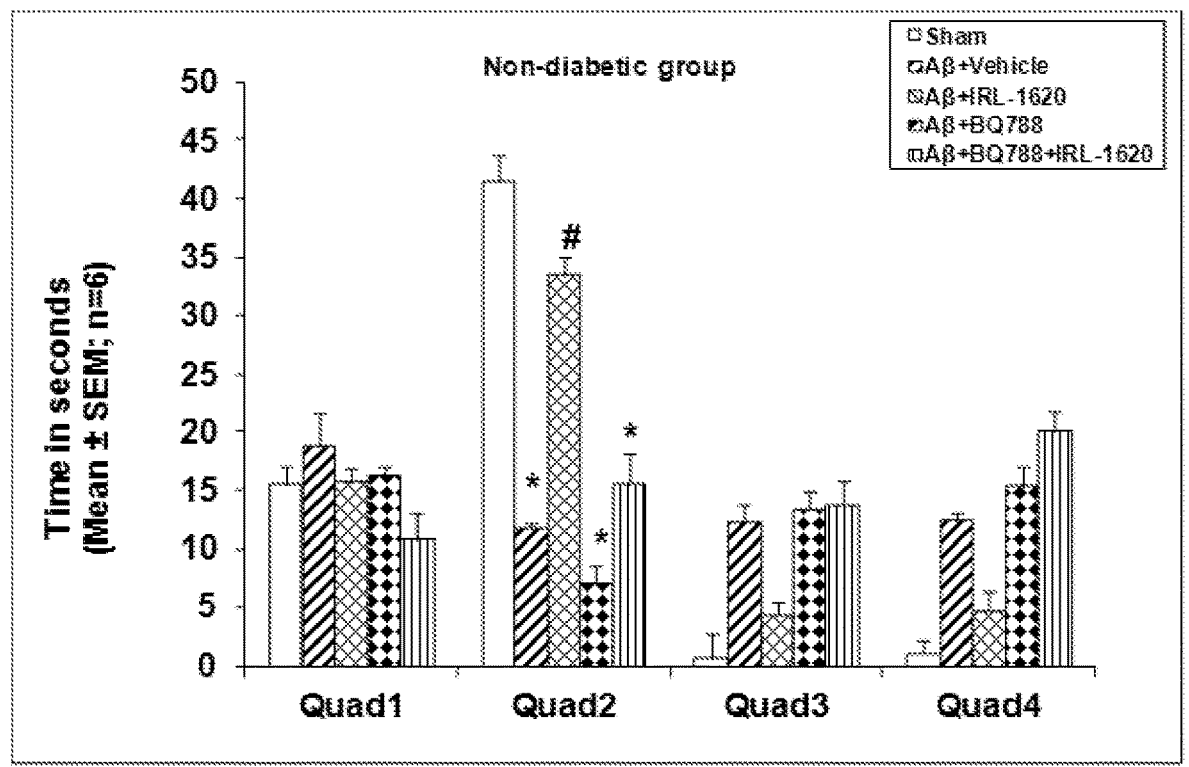
FIG. 9. Effect of an $ET_B$ receptor agonist, IRL-1620, in presence and absence of an $ET_B$ receptor antagonist, BQ788, in the water maze probe trial task. Time spent in each quadrant in the probe trial in non-diabetic rats (A). Representative trajectories of each group during probe trial in the water maze task (B). Values were expressed as mean±S.E.M. *p<0.001 compared to sham; #p<0.001 compared to Aβ+ vehicle (N=6).
Figure 9B:
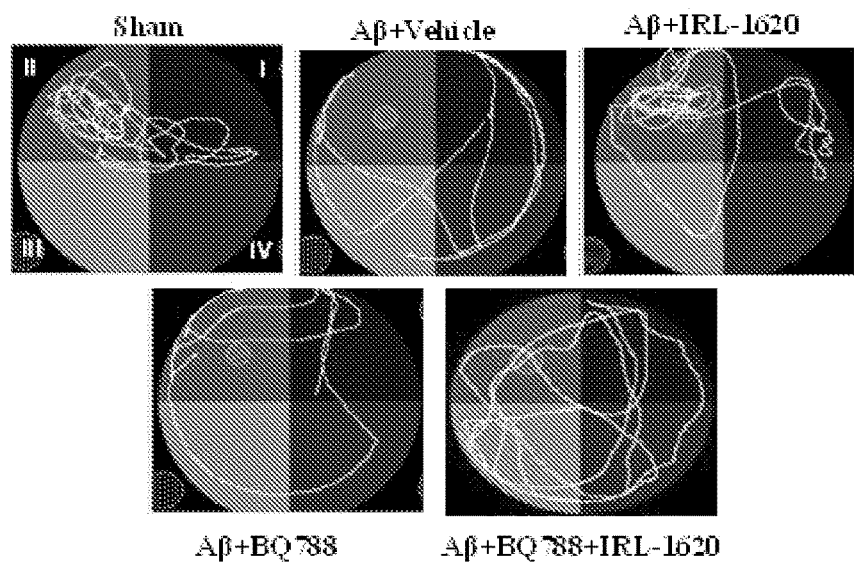
Figure 10A:
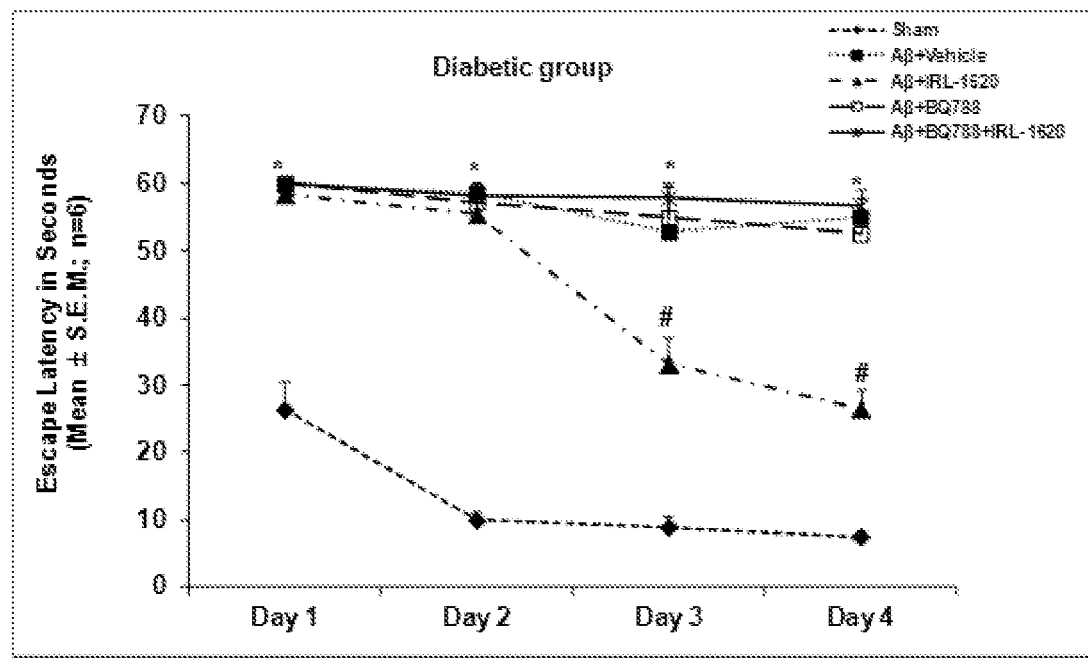
FIG. 10. Effect of an $ET_B$ receptor agonist, IRL-1620, in presence and absence of an $ET_B$ receptor antagonist, BQ788, on the escape latency (A) and path length (B) on each training day of the water maze task in diabetic rats. The animals were submitted to four daily trials to find a hidden platform for 4 training days. Values were expressed as mean±S.E.M. *p<0.001 compared to sham; #p<0.001 compared to Aβ+ vehicle (N=6).
Figure 10B:
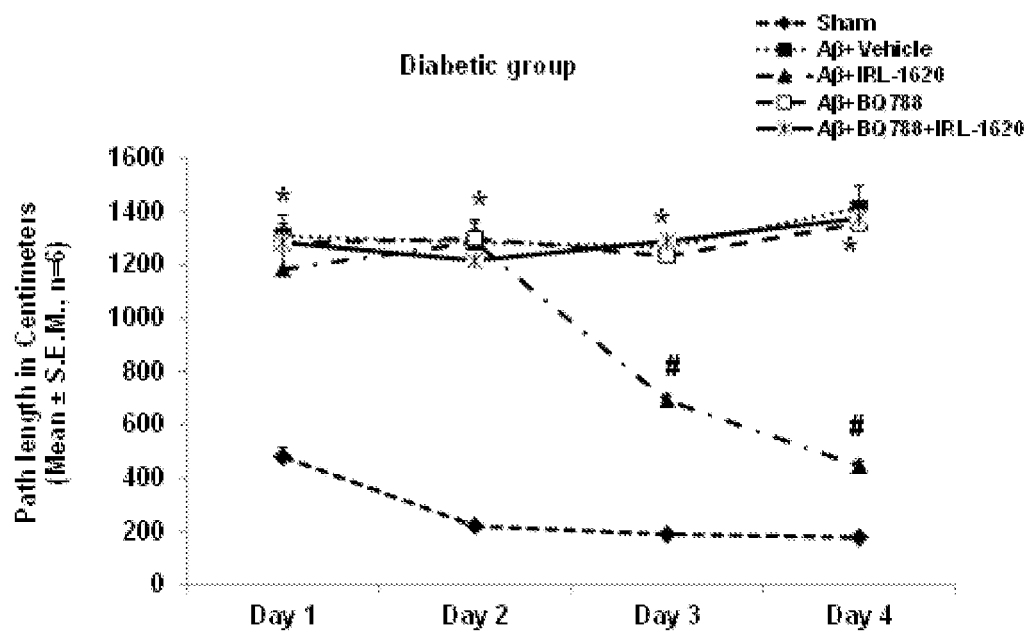
Figure 11A:
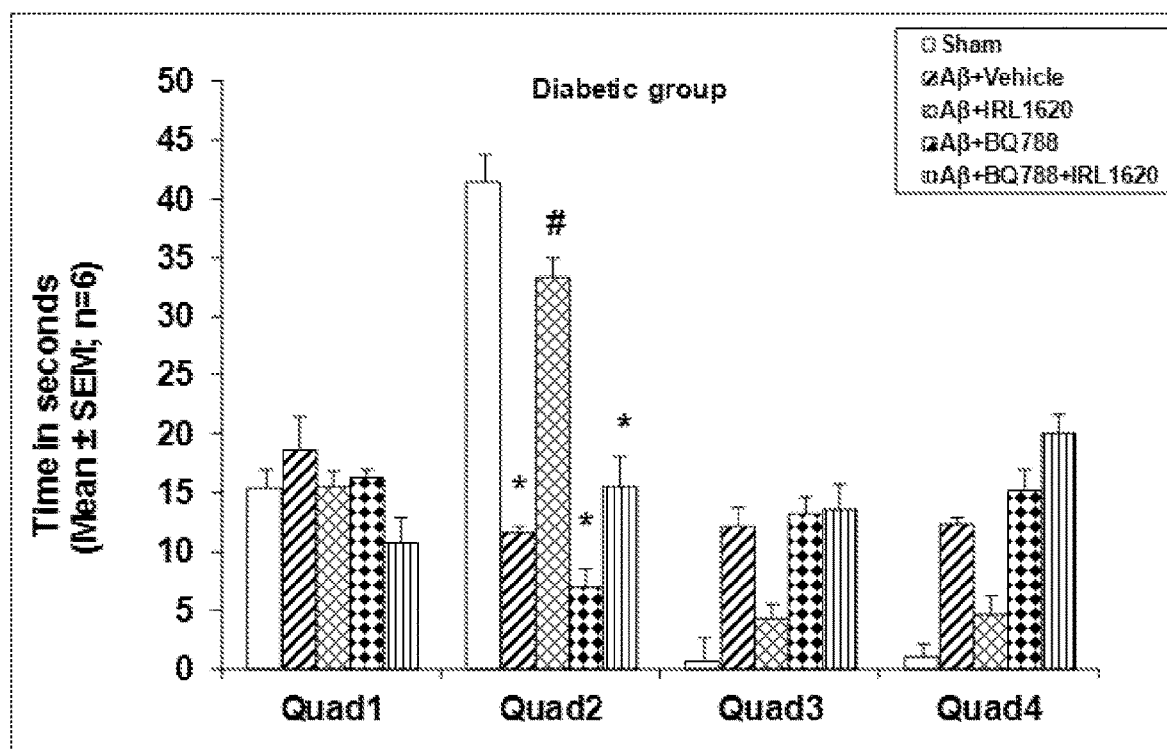
FIG. 11. Effect of an $ET_B$ receptor agonist, IRL-1620, in presence and absence of an $ET_B$ receptor antagonist, BQ788, in the water maze probe trial task. Time spent in each quadrant in the probe trial in diabetic rats (A). Representative trajectories of each group during probe trial in the water maze task (B). Values were expressed as mean±S.E.M. *p<0.001 compared to sham; #p<0.001 compared to Aβ+ vehicle (N=6).
Figure 11B:
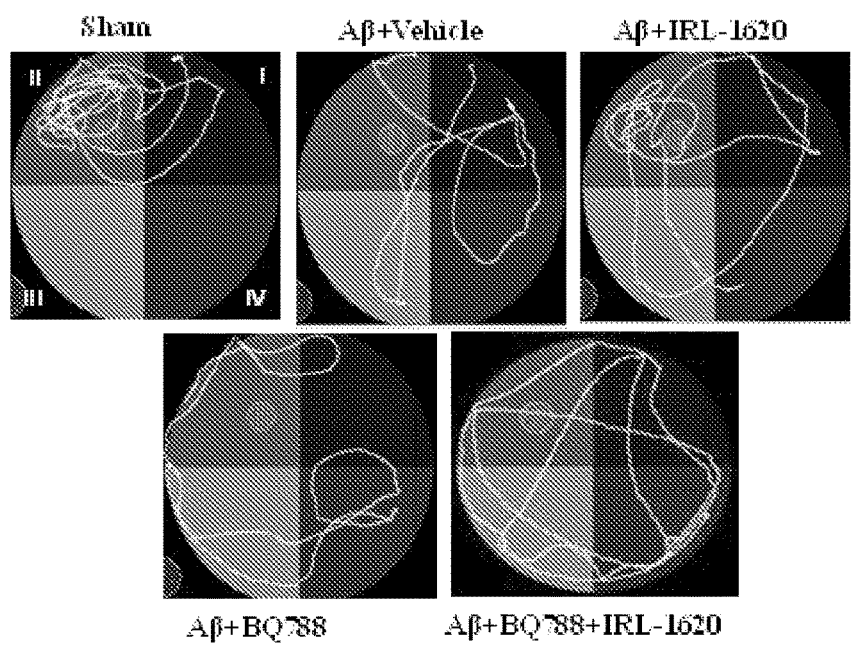

Effect of $ET_B$ Receptor Agonist and Antagonist on Memory Deficit in Aβ Treated Non-Diabetic and Diabetic Rats No significant difference was seen between non-diabetic and diabetic rats in water maze acquisition (FIGS. 8 and 10) and probe trial test (FIGS. 9 and 11). Rats treated with Aβ took significantly ($p<0.0001$) longer time (escape latency) to find the platform. Sham group improved their performance in the hidden platform test as indicated by a decrease in escape latencies across successive days (day effect, $F_{(3,100)}$=3.968, $p<0.001$). There was a significant difference between escape latencies on day 1, 2, 3 and 4 in Aβ rats treated with vehicle compared to sham ($F_{(3,59)}$=8.273, $p<0.0001$). However, when $ET_B$ receptor agonist, IRL-1620 was administered to AP treated rats, escape latency decreased significantly on day 3 and 4 of training when compared to Aβ rats treated with vehicle ($F_{(4,59)}$=19.602, $p<0.001$). IRL-1620 significantly improved cognitive impairment caused by Aβ treatment in rats. On the other hand, administration of an $ET_B$ receptor antagonist, BQ788, blocked the improvement in escape latency produced by IRL-1620 in Aβ rats (FIGS. 8 and 10). A difference in escape latency is also shown in representative trajectories of each group during an acquisition trial in the water maze task (FIGS. 8 and 10). The distance traveled by a rat to reach the platform (path length) decreased across days ($F_{(3,51)}$=76.3, $p<0.0001$), and there was also a significant day x group interaction ($F_{(12,100)}$=8.88, $p<0.0001$) indicating differences among groups within each trial day. There was a significant difference between sham, Aβ rats treated with vehicle and Aβ rats treated with IRL-1620 ($F_{(2,57)}$=24.2, $p<0.01$); post hoc analysis showed that Aβ rats treated with vehicle group swam longer path lengths as compared to sham group ($p<0.001$). Aβ rats treated with IRL-1620 group swam significantly ($p<0.001$) shorter path lengths as compared to vehicle group indicating beneficial effects of IRL-1620 treatment (FIGS. 8 and 10). Aβ produced significant impairment of cognitive function in rats which could be improved with $ET_B$ receptor agonist, and was blocked by specific $ET_B$ receptor antagonist.

Removal of platform from the target quadrant (quadrant II) resulted in a general tendency to swim preferentially in the target quadrant as opposed to other quadrants (probe trial). Therefore, time spent in quadrant II was compared for all the groups in order to observe effect of agents on memory retention. Time spent in other quadrants, specifically, does not reflect degree of memory consolidation and was therefore not subjected to analysis. In probe trial, time spent in the target quadrant was significantly decreased in rats treated with Aβ compared to sham treated rats indicating memory deficit in Aβ treated rats. Administration of $ET_B$ receptor agonist, IRL1620, significantly (p<0.0001) increased time spent in the target quadrant compared to vehicle treated Aβ rats (FIGS. 9 and 11). Administration of an $ET_B$ receptor antagonist, BQ788, to Aβ treated rats did not produce any improvement in time spent in the target quadrant. Difference in time spent in the target quadrant is shown in representative trajectories of each group during probe trial in the water maze task (FIGS. 9 and 11). Aβ produced significant memory deficit in rats which significantly improved with $ET_B$ receptor agonist treatment but was blocked by specific $ET_B$ receptor antagonist.

The purpose of this study was to determine the effect of selective $ET_B$ receptor stimulation by IRL-1620 on functional recovery following experimentally induced cognitive impairment by intracerebroventicular injections of Aβ in adult diabetic and non-diabetic rats. The current findings suggest that IRL-1620 produced a significant preventative effect in Aβ induced cognitive impairment in both diabetic and non-diabetic rats. In order to confirm that the effects of IRL-1620 were specific to stimulation of $ET_B$ receptors, a selective $ET_B$ receptor antagonist, BQ788, was used to block the effect of IRL-1620. Aβ treatment produced a significant increase in oxidative stress markers in non-diabetic and diabetic rats and treatment with selective $ET_B$ receptor agonist, IRL-1620, significantly reduced oxidative stress markers. The reduction in oxidative stress marker induced by IRL-1620 was blocked by pretreatment with specific $ET_B$ receptor antagonist, BQ788, in Aβ non-diabetic and diabetic rats.

The incidence of diabetes mellitus and AD increases with age, and the incidence of AD is significantly higher in patients with diabetes mellitus (Janson et al., 2004). Pathologically, both are associated with altered glucose homeostasis and extracellular accumulation of amyloid proteins. This suggests that there are common underlying mechanisms such as cross-seeding of amyloid proteins or metabolic dysfunction. Therefore, the effect of IRL-1620 was studied in both non-diabetic and diabetic rats treated with Aβ.

The prevalence of dementia, particularly of AD type is increasing and it is one of the most significant neurodegenerative disorders in the elderly. Recent studies support that metabolic and vascular dysfunctions are involved in pathology and progression of AD. Vascular alterations, with impairment of glucose utilization and blood flow changes, occur with and prior to AD diagnosis (Baquer et al., 2009; Casadesus et al., 2007; Meier-Ruge et al., 1994). These changes precede cognitive impairment and exacerbate underlying AD pathology. The discovery and prevention of vascular dysfunction could lead to new strategies to prevent or halt the progression of AD. Closely linked with vascular changes in AD is Aβ, the major protein component of senile plaques in AD brains. An elevated level of Aβ in the brain is one of the prominent features of AD (Hardy and Selkoe, 2002). Tissues that produce the most Aβ are the brain and skeletal muscles, both of which possess high metabolism and well-developed vascular networks (Cirrito et al., 2005; Ethell, 2010). Vascular damage and reactive gliosis are co-localized with amyloid deposits in AD brains, suggesting that vasculature may be a clinically significant site of AD pathology (Suo et al., 1998).

ET system has long been known to play an important role in the regulation of cerebral blood circulation. Several studies have demonstrated involvement of ET in AD. Due to highly potent vasoconstriction caused by ET-1 via $ET_A$ receptors, it was postulated that administration of an ET antagonist would decrease the damage associated with AD. $ET_A$ receptor antagonists, BQ123 and BMS 182874, demonstrated reduced oxidative stress and improve the learning and memory deficit following Aβ treatment in rats. However, a combined $ET_{A/B}$ receptor antagonist had no beneficial effect (Briyal et al., 2011). This led us to investigate the involvement of $ET_B$ receptors in AD. In fact, the ET binding sites in the brain are predominantly of $ET_B$ receptors, and $ET_B$ receptor agonists act as anti-apoptotic factor against the neurotoxicity of Aβ (Yagami et al., 2002). Elevation of Aβ is directly implicated in vascular pathology, and vascular dysfunction in AD is characterized by disruption of vascular architecture including lower capillary density and reduced blood flow (Bell and Zlokovic, 2009; de la Torre, 1994; Iadecola et al., 2009; Zlokovic, 2008). Conversely, activation of endothelial $ET_B$ receptors is known to elicit vasodilatation, and previous studies in our lab have indicated that this leads to an increase in CBF in normal rats (Leonard and Gulati, 2009), indicating a possible role of $ET_B$ agonists in the treatment and prevention of AD.

In the present study, Aβ treated rats received either vehicle or IRL-1620 for 14 days. On day 15, animals were evaluated for cognitive impairment and their brains were removed for analysis of oxidative stress markers. Treatment with IRL-1620 effectively reduced oxidative stress as measured by decreased levels of malondialdehyde (MDA) and increased levels of reduced glutathione (GSH) and superoxide dismutase (SOD) compared to vehicle treated group. Blockade of $ET_B$ receptors with BQ788, on the other hand, resulted in an increase in oxidative stress. Increased levels of MDA along with decreased levels of antioxidants GSH and SOD are all hallmarks of oxygen free radical generation occurring as an early event in AD pathology (Cutler et al., 2004; Nunomura et al., 2001). The etiology of AD is thought to be complex and initiates a variety of biochemical reactions leading to excess intracellular $Ca^{2+}$, glutamate excitotoxicity, production of reactive oxygen species, and eventual apoptosis. Agents that target these events in order to slow or prevent irreversible injury are labeled as neuroprotective. Oxidative stress and Aβ are related to each other (Hensley et al., 1994; Mark et al., 1997). Oxidative stress also contributes to vascular dysfunction. It has been reported that oxidative damage during pathogenesis of AD may be directly due to Aβ (Murray et al., 2007; Murray et al., 2005). It is disclosed herein that the $ET_B$ receptor agonist, IRL-1620, decreased the oxidative stress markers that were increased by Aβ. It appears that Aβ can produce vasoconstriction and an increase oxidative stress, both of which could be mediated through ET. Stimulation of endothelial $ET_B$ receptors is known to elicit vasodilatation, and previous studies in our lab have indicated that this leads to an increase in CBF. Hence, $ET_B$ receptor agonists may be quite effective in preventing the damage due to Aβ in AD.

Thus, it is disclosed herein that stimulation of $ET_B$ receptors following Aβ treatment leads to functional recovery. Behavioral studies were conducted using MWM to determine whether $ET_B$ receptor agonists are able to improve the impairment of learning and memory caused by Aβ. It was found that Aβ produced a significant impairment in spatial memory as evidenced by significantly longer escape latencies and no preference for the quadrant which previously contained the platform in the probe trial. Other researchers have also shown learning and memory deficits due to Aβ (Ahmed et al., 2010; Lopes et al., 2010; Tsukuda et al., 2009). It is shown herein that the specific $ET_B$ receptor agonist, IRL-1620, significantly improved the spatial memory deficit caused by Aβ treatment. On the other hand, antagonism of $ET_B$ receptors with BQ788, given prior to either vehicle or IRL-1620, resulted in learning and memory deficit similar to those seen in vehicle group. These results suggest that the improvement seen with IRL-1620 is due to selective stimulation of the $ET_B$ receptors. The observed functional deficits coincided with changes observed in oxidative stress markers.

Activation of $ET_B$ receptors with 1RL-1620 is known to cause cerebral vasodilatation and increased blood flow through release of nitric oxide (NO) (Kitazono et al., 1995; Leonard and Gulati, 2009; Tirapelli et al., 2005). Previous findings have revealed that cerebral neurovascular dysfunction in relation to bioavailability of NO formed by endothelial NO contributes to cognitive decline and neurodegeneration in AD (de la Torre et al., 2003). NO also plays an obligatory role in the regulation of CBF and cell viability and in the protection of nerve cells in AD (Toda et al., 2009). Recent studies have demonstrated that endothelial NO stimulation and increased CBF via pharmacological means enhance angiogenesis (Chen et al., 2007; Ding et al., 2008). Along these lines, the $ET_B$ receptor has been shown to enhance the formation of new blood vessels through eNOS (Goligorsky et al., 1999). Previous reports using an $ET_B$ receptor deficient model have indicated that this receptor promotes neuronal survival and decreases apoptosis in the hippocampus, dentate gyrus, and olfactory epithelium (Ehrenreich, 1999; Laziz et al., 2011; Riechers et al., 2004). Both induction of eNOS and direct anti-apoptotic neuronal effects of $ET_B$ receptor activation may play a role in reduction of oxidative stress and improvement in behavioral recovery following AD.

In conclusion, reduction in oxidative stress and improvement in cognitive impairment following $ET_B$ receptor agonist, IRL-1620, and attenuation of these effects by a specific $ET_B$ receptor antagonist, BQ788, in the current study indicates that $ET_B$ receptors may be a new therapeutic target for neuroprotection in AD.

Studies in Animal Model of Stroke

Effect of IRL-1620 on levels of brain endothelin receptors in middle cerebral artery occluded rats: $ET_B$ receptors are present in large number in the CNS and appear to play a key role in its development. It has been demonstrated that $ET_B$ receptors in the brain are overexpressed at the time of birth and their expression decreases with maturity of the brain (Briyal et al., 2012b). It has also been shown that acute ischemic phase is followed by an intense sprouting of neurons and capillaries (Carmichael, 2006; Murphy and Corbett, 2009) along with activation of glial cells to create an environment for neuronal growth and plasticity (Hermann and Zechariah, 2009; Zhang and Chopp, 2009). A regenerative response will be pharmacologically activated in the ischemic brain by stimulating $ET_B$ receptors. Stimulation of $ET_B$ receptors by IRL-1620 has been shown to provide neuroprotective effect in MCAO rats (Leonard et al., 2011; 2012; Leonard and Gulati, 2013). $ET_A$ receptors are increased in the infarcted hemisphere at 24 hours post ischemia and subsequently return to normal levels by one week, on the other hand a significant increase in $ET_B$ receptor expression occurs after 1 week only in the infarcted hemisphere of rats treated with IRL-1620 (Leonard et al., 2012). It is contemplated that IRL-1620 not only stimulates $ET_B$ receptors but in longer periods increases the number and affinity of these receptors.

Effect of IRL-1620 on neurological deficit following focal cerebral ischemia: In a preliminary study, the effect of selectively activating $ET_B$ receptors by IRL-1620 following permanent middle cerebral artery occlusion in rats was determined. Twenty-four hours after middle cerebral artery occlusion, there was a significantly (P<0.001) higher neurological deficit and poor motor function compared to sham-operated rats, indicative of neurological impairment following induction of cerebral ischemia. Animals treated with IRL-1620 showed significant improvement in all neurological and motor function tests when compared with vehicle-treated. In a longer term study, cerebral ischemia resulted in a distinct loss of motor coordination as measured by the foot fault error and rota rod tests at 1, 4, and 7 days post infarction. Whereas vehicle-treated occluded rats performed worse with each assessment, animals treated with $ET_B$ receptor agonist, IRL-1620, showed minimal deficit at day one following occlusion, and improved over the course of 7 days. Pretreatment with $ET_B$ receptor antagonist, BQ-788, followed by either vehicle or IRL-1620 resulted in significantly more deficits than both sham-operated (P<0.001) or IRL-1620 (P<0.05) treatment, indicating that the improvement observed with IRL-1620 is specific to the stimulation of $ET_B$ receptors (Leonard et al., 2011; 2012).

Figure 14A:
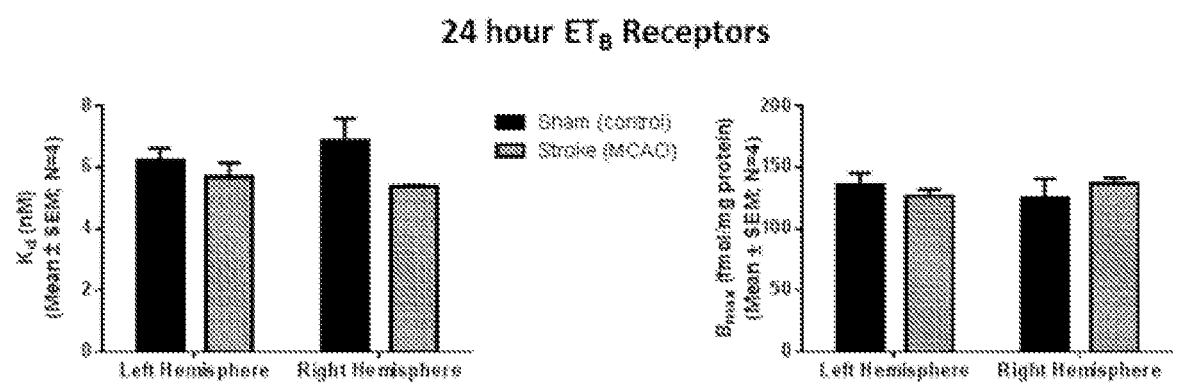
FIG. 14: Binding affinity ($K_d$) and receptor density ($B_{max}$) of $ET_B$ receptors in the left and right cerebral hemisphere in male Sprague Dawley rats (A) 24-hours and (B) 7 days following MCAO. Values are expressed as Mean±S.E.M, N=4 each group. No significant change in $K_d$ or $B_{max}$ was observed between left and right hemispheres in both sham (control) and stroke (MCAO) groups.
Figure 14B:
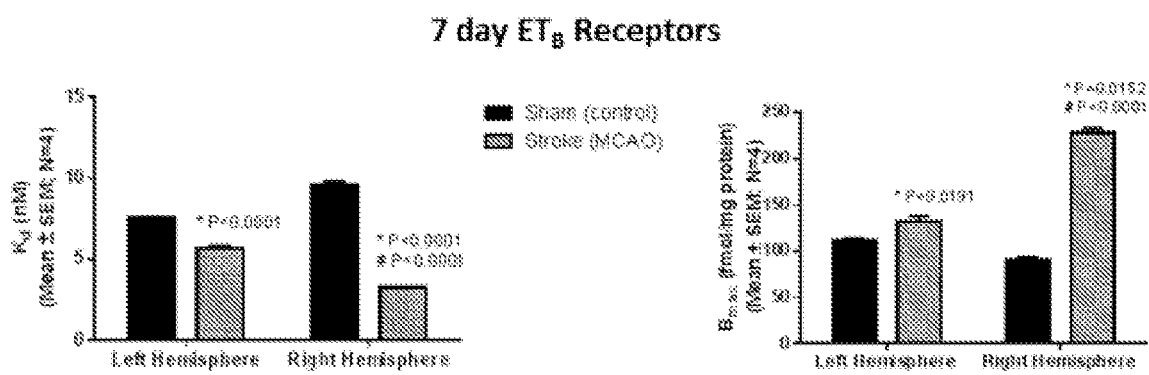
Figure 15:
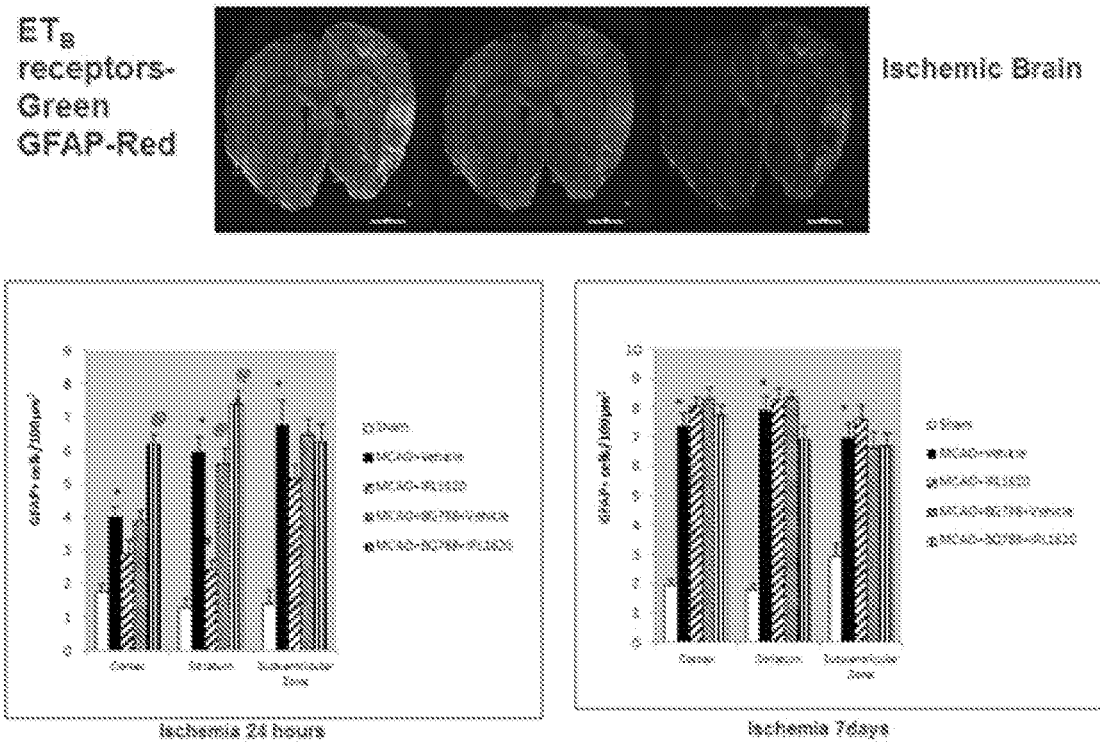
FIG. 15: Effect of $ET_B$ receptor agonist, IRL-1620 (3 doses of 5 µg/kg, i.v., at 2, 4 and 6 hours post ischemia), and antagonist, BQ788 (1 mg/kg, i.v.), on glial fibrillary acidic protein (GFAP) post middle cerebral artery occlusion. A. Representative 30 µm-thick ischemic brain slice stained for the $ET_B$ receptor (green) and GFAP (red). Scale bar=2000 p.m. Bottom panel shows number of reactive astrocytes (GFAP+ cells) per 100 µm² in the cortex, striatum, and subventricular zone of middle cerebral artery occluded rats at 24 h after infarct. *P<0.001 vs. sham. #P<0.0001 vs. MCAO+vehicle. @P<0.01 vs. MCAO+IRL-1620; and number of reactive astrocytes (GFAP+ cells) per 100 µm² in the cortex, striatum, and subventricular zone of middle cerebral artery occluded rats at 1 w after infarct. Values are expressed as mean±SEM (n=5/group). *P<0.001 vs. sham.
Figure 16A:
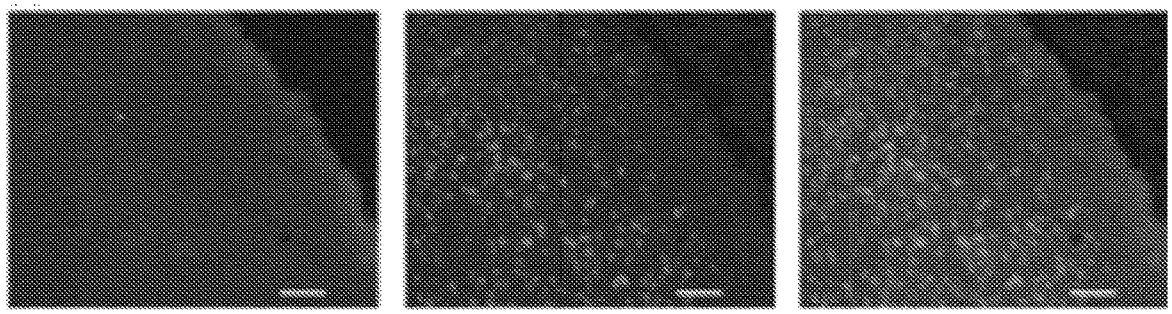
FIG. 16: Effect of ETB receptor agonist, IRL-1620 (three doses of 5 µg/kg, i.v., at 2, 4 and 6 h post ischemia), and antagonist, BQ788 (1 mg/kg, i.v.), on neuronal nuclei (NeuN) post middle cerebral artery occlusion. (A) Representative image of the cortex of an IRL-1620-treated animal 1 week following MCAO, stained for the ETB receptor (green) and NeuN (red). Scale bar=100 µm. (B) Representative image of the striatum of an IRL-1620-treated animal 1 week following MCAO, stained for the ETB receptor (green) and NeuN (red). Scale bar=10 µm. (C) Number of neuronal nuclei per 100 µm² in the cortex, striatum, and subventricular zone of middle cerebral artery occluded rats at 24 h after infarct. *P<0.05 vs. sham. #P<0.01 vs. MCAO+vehicle. @P<0.0001 vs. MCAO+IRL-1620. (D) Number of neuronal nuclei per 100 µm² in the cortex, striatum, and subventricular zone of middle cerebral artery occluded rats at 1 week after infarct. Values are expressed as mean±SEM (n=5/group). *P<0.0001 vs. sham. #P<0.0001 vs. MCAO+ vehicle. @P<0.0001 vs. MCAO+IRL-1620.
Figure 16B:
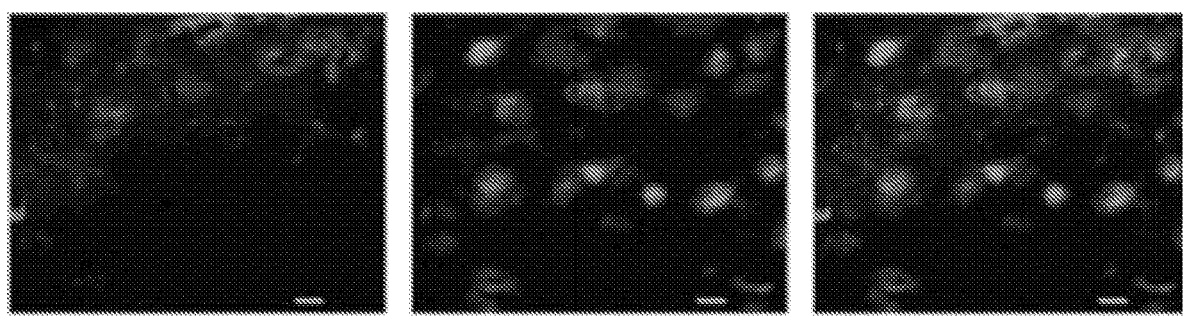
Figure 16C:
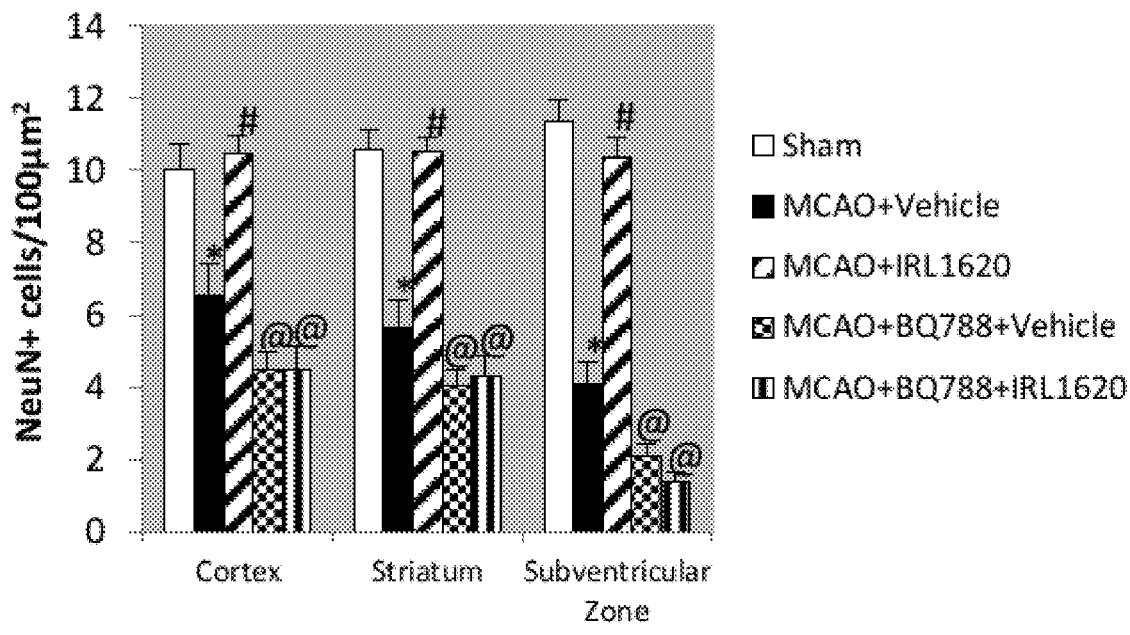
Figure 16D:
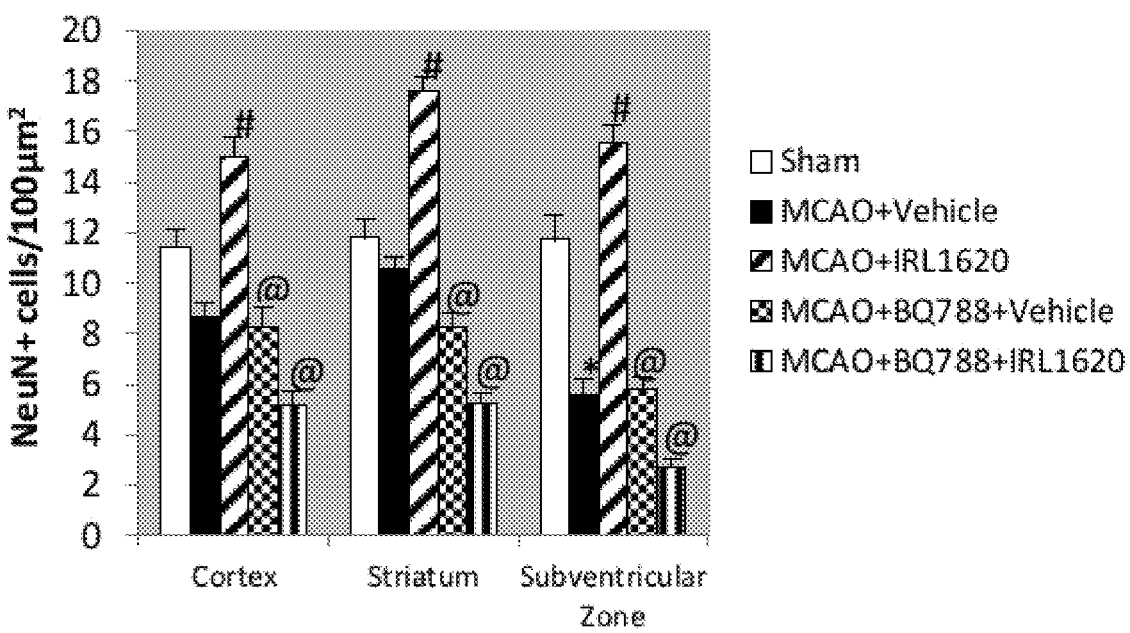
Figure 17:
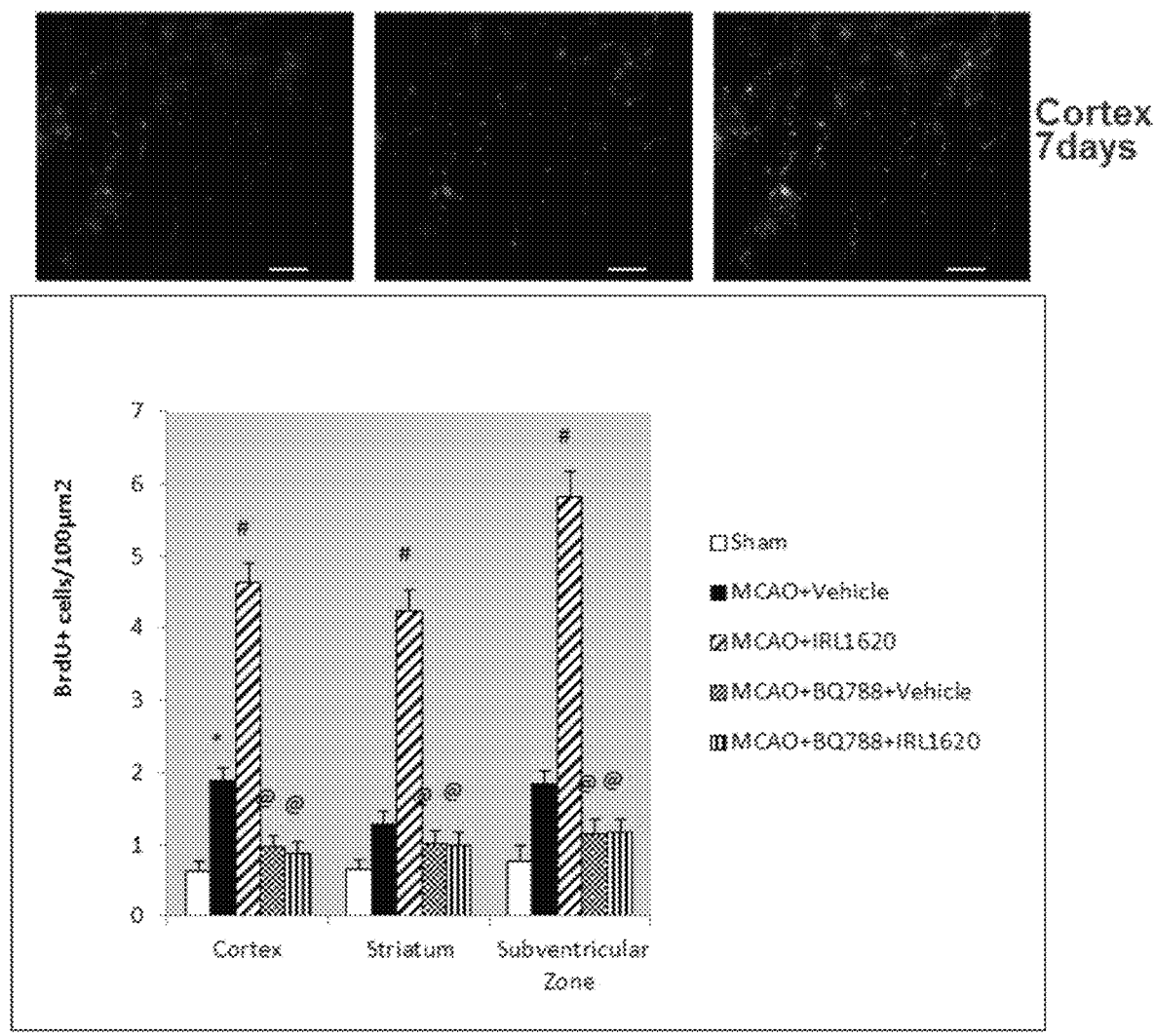
FIG. 17: Effect of $ET_B$ receptor agonist, IRL-1620 (3 doses of 5 µg/kg, i.v., at 2, 4 and 6 hours post ischemia), and antagonist, BQ788 (1 mg/kg, i.v.), on proliferating cells post middle cerebral artery occlusion. Representative image of the cortex of an IRL-1620-treated animal 1 week following MCAO depicting a cerebral blood vessel, stained for the $ET_B$ receptor (green) and BrdU (red). Scale bar=100 µm. Bottom panel shows number of proliferating cells (BrdU+) per 100 µm² in the cortex, striatum, and subventricular zone of middle cerebral artery occluded rats at 1 week after infarct. Values are expressed as mean±SEM (n=5/group). *P<0.01 vs. sham. #P<0.0001 vs. MCAO+vehicle. @P<0.0001 vs. MCAO+IRL-1620.

Effect of IRL-1620 on binding characteristics of $ET_B$ receptors following focal cerebral ischemia: Changes in binding characteristics of $ET_B$ receptors were determined in the brain, 1 and 7 days following MCAO. MCAO was produced in rats and binding studies were performed using $[^{125}I]$-IRL-1620 (specific activity 2200 Ci/mmol) as the radioligand and cold IRL-1620 (0-32 nM) as displacer. Non-specific binding was determined using 1 μM concentration of IRL-1620. $K_d$ and $B_{max}$ values were calculated using GraphPad Prism version 5.00 for Windows (GraphPad Software, San Diego). Binding characteristics ($K_d$ and $B_{max}$) were not altered at 24 hours post MCAO. However, a significant decrease in $K_d$ values of $ET_B$ receptor binding in both left and right hemispheres was observed 7 days post-MCAO. The decrease in $K_d$ in the right (ischemic) hemisphere was significantly (P<0.001) greater compared to left (non-ischemic) hemisphere. $B_{max}$ was increased in both left and right hemispheres with the right hemisphere showing a significantly (P<0.001) greater increase compared to the left hemisphere (FIG. 14). It can be concluded that an increase in the density and affinity of $ET_B$ receptors on the $7^{th}$ day of cerebral ischemia is an attempt to provide neuroprotection of ischemic brain.

Figure 12:
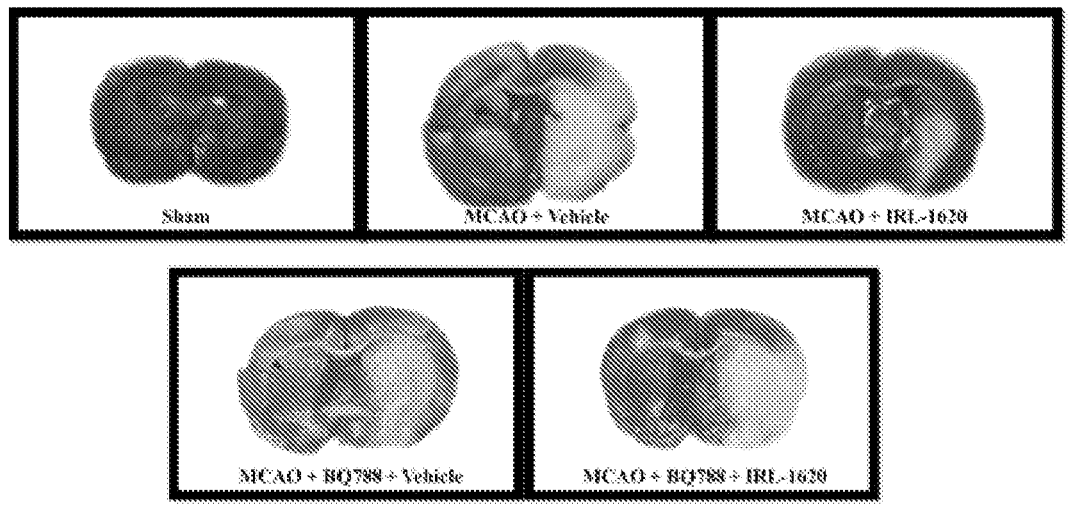
FIG. 12: Two mm coronal sections of brains stained with TTC to visualize the infarct area 7 days post middle cerebral artery occlusion (red indicates normal tissue and white indicates infarct tissue). Representative slices from groups are shown. IRL-1620 (5 µg/kg, IV) or isotonic saline (1 ml/kg, IV) was injected at 2, 4, and 6 hr post MCAO. BQ-788 (1 mg/kg, IV) was administered once 15 min prior to the first injection of IRL-1620 or vehicle.

Effect IRL-1620 on infarct volume in middle cerebral artery occluded rats: Middle cerebral artery occlusion for 7 days resulted in an infarct volume of 177.06±13.21 mm³ in vehicle-treated rats. Administration of IRL-1620 significantly reduced infarct volume (54.06±14.12 mm³; P<0.05) as compared with vehicle. Infarct volumes did not reduce when $ET_B$ receptor antagonist, BQ-788, was given with either vehicle or IRL-1620 (FIG. 12). A substantial edema was noted in the vehicle-treated animals, with the infarcted hemisphere 9.73±1.26% larger than the contralateral hemisphere, whereas IRL-1620-treated animals showed no significant edema, with infarcted hemisphere only 1.51±1.81% larger than non-infarcted hemisphere. Conversely, blockade of the $ET_B$ receptor with BQ-788 followed by either vehicle or IRL-1620 treatment significantly increased edema (17.02±3.17 and 17.97±5.17%, respectively, P<0.01) (Leonard et al., 2012).

Figure 13:
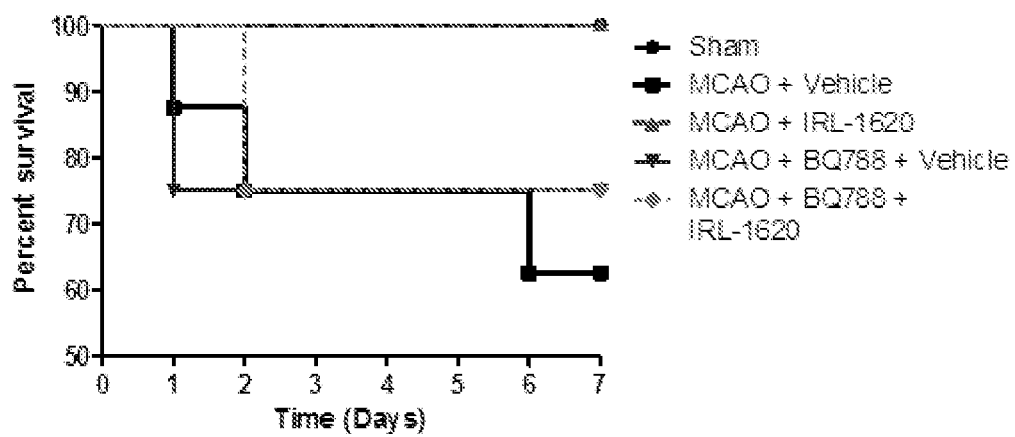
FIG. 13: Effect of $ET_B$ receptor agonist, IRL-1620, in presence and absence of BQ788 on 7 day survival of rats undergoing either sham surgery or middle cerebral artery occlusion.

Effect of IRL-1620 on 7 day survival of rats following focal cerebral ischemia: Studies were also conducted to determine the effect of stimulating $ET_B$ receptors using a selective agonist, IRL-1620, in rats with middle cerebral artery occlusion (MCAO). It was found that there was no mortality in sham treated rats throughout the 7 day observation period. However, MCAO rats in the vehicle treated group presented with 38% mortality by $7^{th}$ day. On the other hand, MCAO rats treated with IRL-1620 showed no mortality throughout the 7 day period. However, MCAO rats treated with an $ET_B$ receptor antagonist, BQ-788+vehicle or BQ-788+IRL-1620, showed 25% mortality during the 7 day observation (FIG. 13) (Leonard et al., 2012). Preliminary results and supporting literature have prompted the investigation of the mechanism involved in neuroprotective and neurorestorative effects of stimulating $ET_B$ receptors in rats with cerebral ischemia.

Figures 18A, 18B:
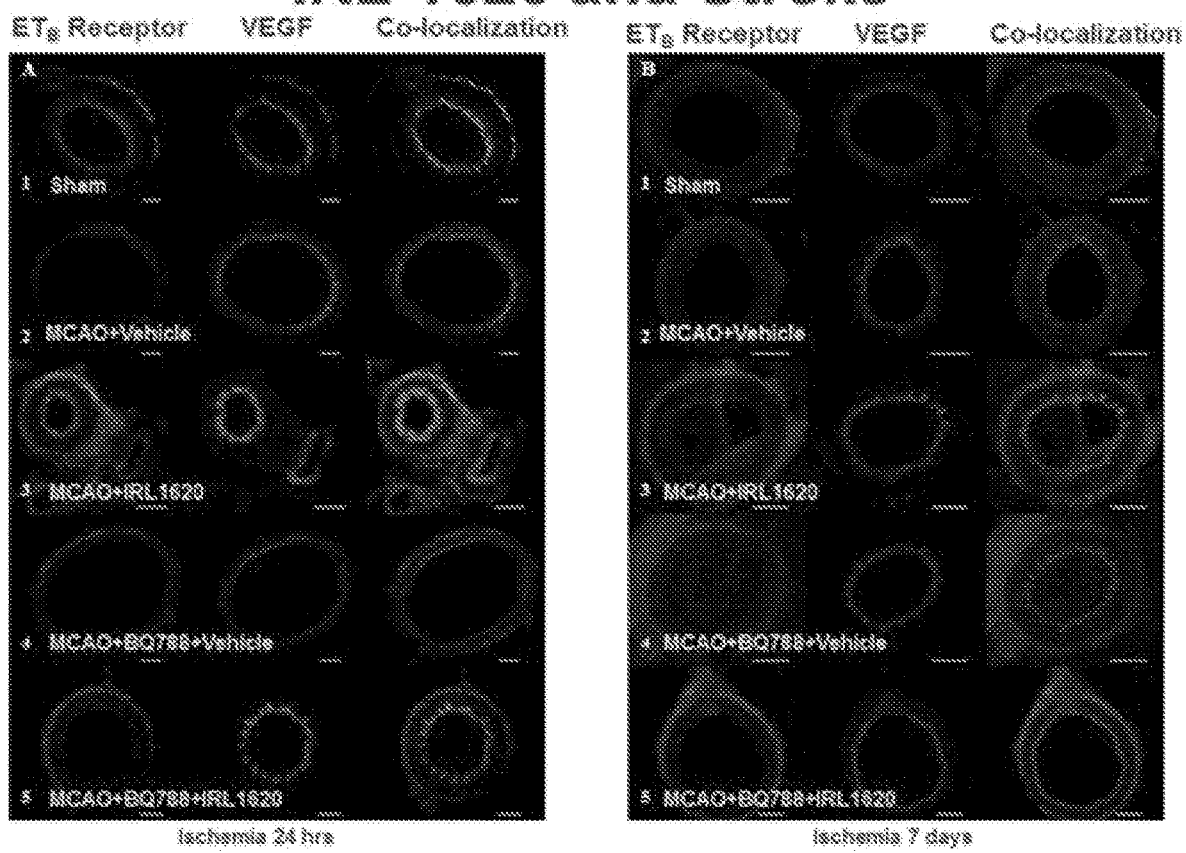
FIG. 18: Effect of $ET_B$ receptor agonist, IRL-1620 (3 doses of 5 µg/kg, i.v., at 2, 4 and 6 hours post ischemia), and antagonist, BQ788 (1 mg/kg, i.v.), on vascular endothelial growth factor (VEGF) post middle cerebral artery occlusion. A. Representative images of blood vessels in the rat cortex 24 h following MCAO, stained for the $ET_B$ receptor (green) and VEGF (red). Rows: 1. Sham; 2. MCAO+vehicle; 3. MCAO+IRL-1620; 4. MCAO+BQ788+vehicle; 5. MCAO+BQ788+IRL-1620. Scale bar=10 µm. B. Representative images of blood vessels in the rat cortex 1 week following MCAO, stained for the $ET_B$ receptor (green) and VEGF (red). Rows same as in (A 24 h). Scale bar=10 µm.
Figure 19:
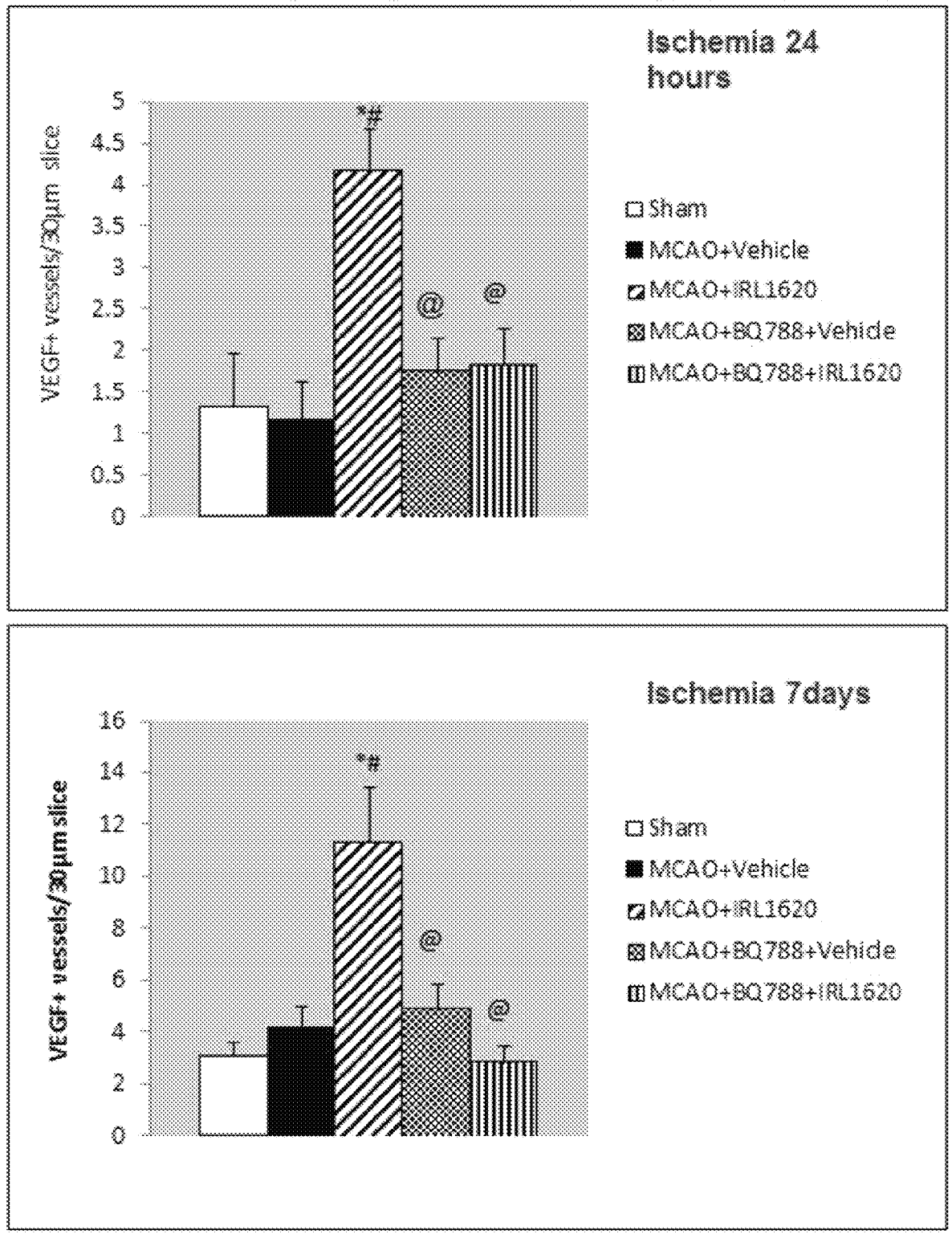
FIG. 19: Effect of $ET_B$ receptor agonist, IRL-1620 (3 doses of 5 µg/kg, i.v., at 2, 4 and 6 hours post ischemia), and antagonist, BQ788 (1 mg/kg, i.v.), on vascular endothelial growth factor (VEGF) post middle cerebral artery occlusion. Upper panel shows number of VEGF+vessels per 30 µm brain slice middle cerebral artery occluded rats at 24 h after infarct. *P<0.05 vs. sham. #P<0.01 vs. MCAO+vehicle. @P<0.05 vs. MCAO+IRL-1620. The lower panel shows number of VEGF+ vessels per 30 µm brain slice middle cerebral artery occluded rats at 1 week after infarct. Values are expressed as mean±SEM (n=5/group). *P<0.01 vs. sham. #P<0.01 vs. MCAO+vehicle. @P<0.05 vs. MCAO+IRL-1620.
Figure 20A:
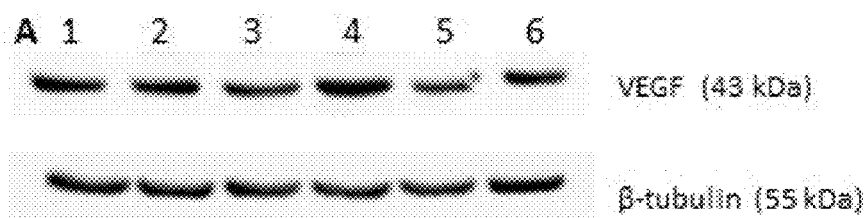
FIG. 20: Effect of $ET_B$ receptor agonist, IRL-1620 (3 doses of 5 µg/kg, i.v., at 2, 4 and 6 hours post ischemia), on protein levels of vascular endothelial growth factor (VEGF) post middle cerebral artery occlusion. A. Representative blot of VEGF protein levels in the rat brain 24 hours post MCAO with β-tubulin as a loading control. Lane 1—sham (LH), Lane 2—sham (RH), Lane 3—MCAO+Vehicle (LH), Lane 4—MCAO+Vehicle (RH), Lane 5—MCAO+IRL-1620 (LH), Lane 6—MCAO+IRL-1620 (RH). LH=left hemisphere, RH=right hemisphere. B. Representative blot of VEGF protein levels in the rat brain 1 week post MCAO with β-tubulin as a loading control, with lane distribution the same as in (A). C. Expression of VEGF protein levels in the rat brain 24 hours following MCAO. D. Expression of VEGF protein levels in the rat brain 1 week following MCAO. Values are expressed as mean±SEM (n=5/group). *P<0.001 vs. Sham. #P<0.01 vs MCAO+Vehicle.
Figure 20B:
Figure 20C:
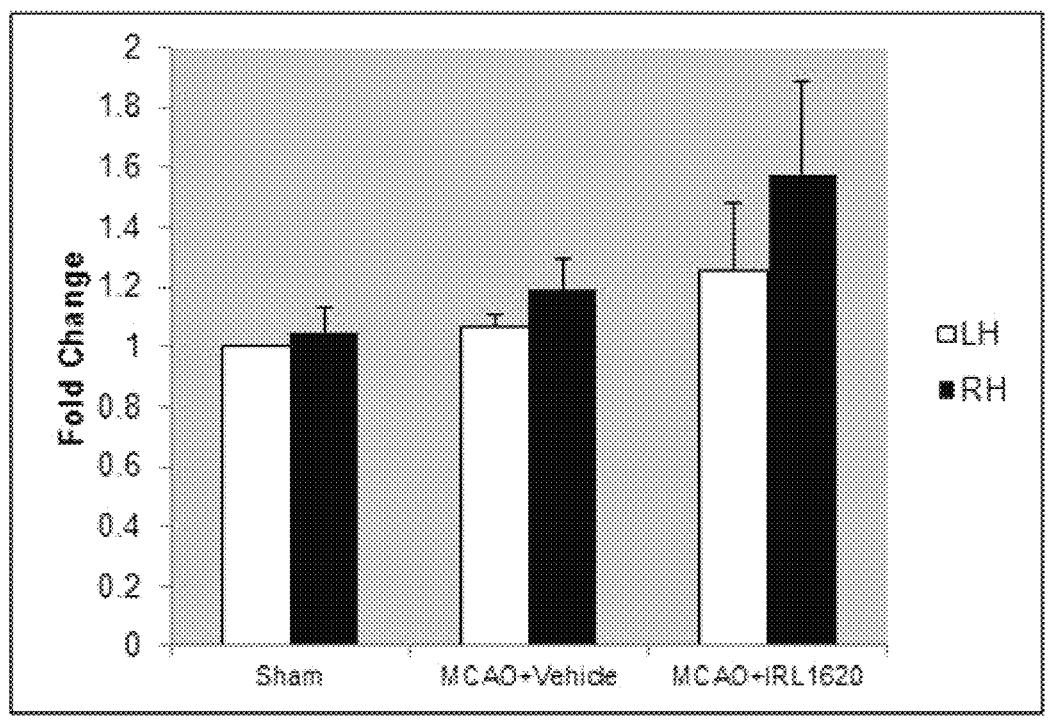
Figure 20D:
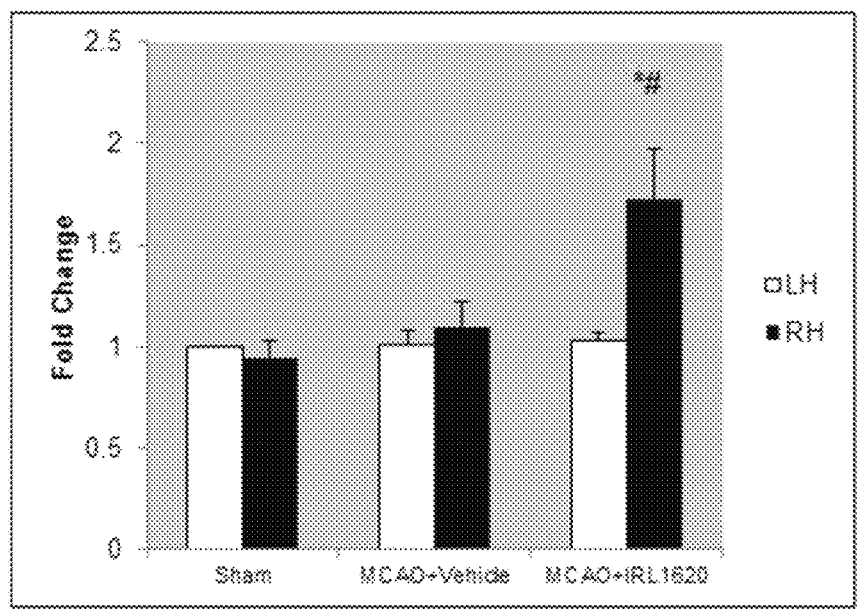
Figure 21A:
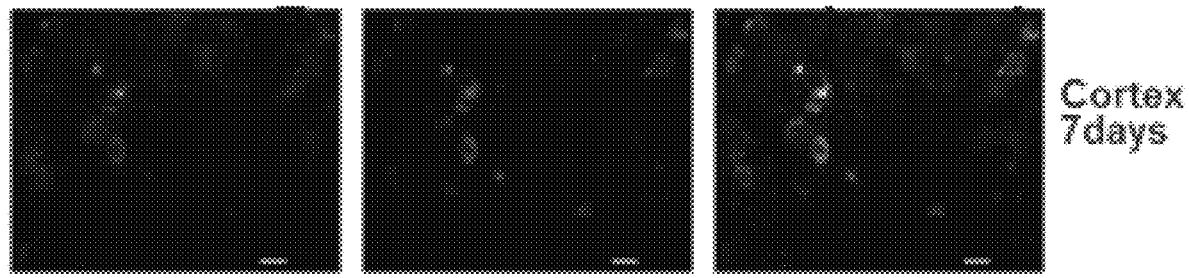
FIG. 21: Effect of $ET_B$ receptor agonist, IRL-1620 (3 doses of 5 µg/kg, i.v., at 2, 4 and 6 hours post ischemia), and antagonist, BQ788 (1 mg/kg, i.v.), on nerve growth factor (NGF) post middle cerebral artery occlusion. A. Representative image of the cortex of an IRL-1620-treated animal 1 week following MCAO, stained for the $ET_B$ receptor (green) and NGF (red). Scale bar=10 µm. B. Number of NGF+cells per 100 µm$^2$ in the cortex, striatum, and subventricular zone of middle cerebral artery occluded rats at 1 week after infarct. Values are expressed as mean±SEM (n=5/group). #P<0.0001 vs. MCAO+vehicle. @P<0.0001 vs. MCAO+IRL-1620.
Figure 21B:
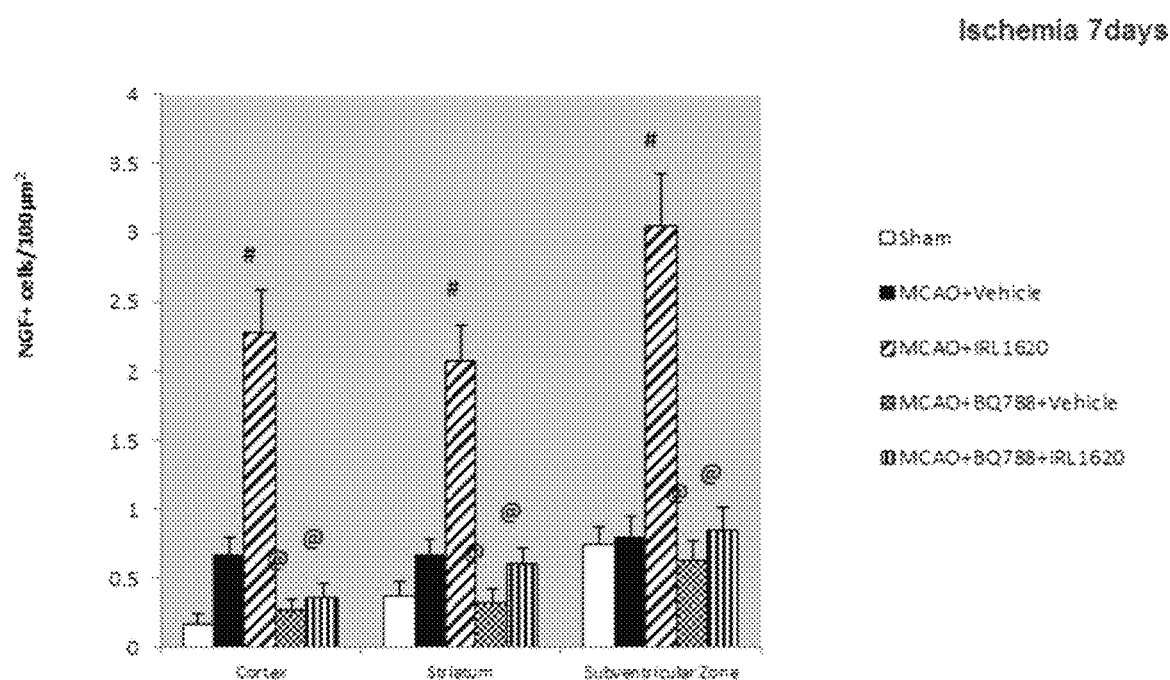
Figure 22A:
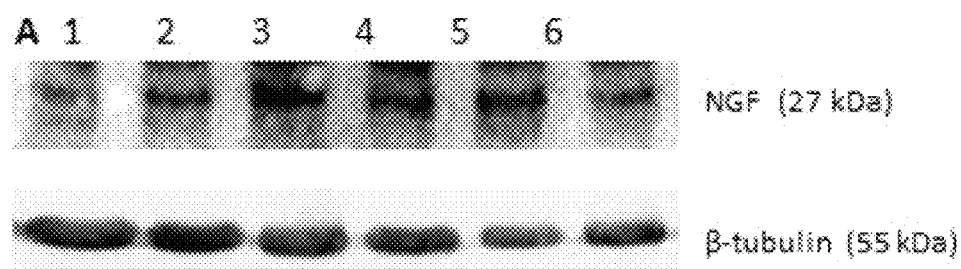
FIG. 22: Effect of $ET_B$ receptor agonist, IRL-1620 (3 doses of 5 µg/kg, i.v., at 2, 4 and 6 hours post ischemia), on protein levels of nerve growth factor (NGF) post middle cerebral artery occlusion. A. Representative blot of NGF protein levels in the rat brain 24 hours post MCAO with β-tubulin as a loading control. Lane 1—sham (LH), Lane 2—sham (RH), Lane 3—MCAO+Vehicle (LH), Lane 4—MCAO+Vehicle (RH), Lane 5—MCAO+IRL-1620 (LH), Lane 6—MCAO+IRL-1620 (RH). LH=left hemisphere, RH=right hemisphere. B. Representative blot of NGF protein levels in the rat brain 1 week post MCAO with β-tubulin as a loading control, with lane distribution the same as in (A). C. Expression of NGF protein levels in the rat brain 24 hours following MCAO. D. Expression of NGF protein levels in the rat brain 1 week following MCAO. Values are expressed as mean±SEM (n=5/group). *P<0.01 vs. Sham.
Figure 22B:
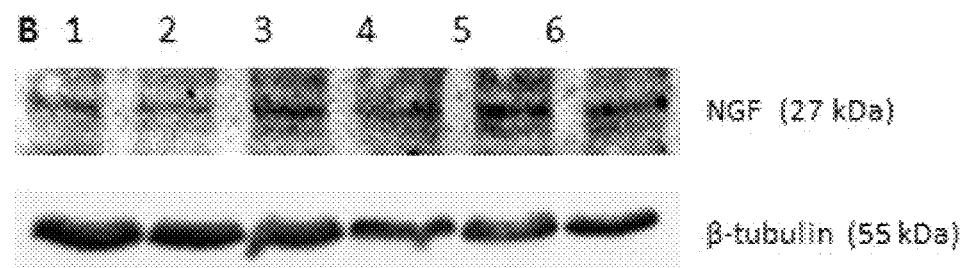
Figure 22C:
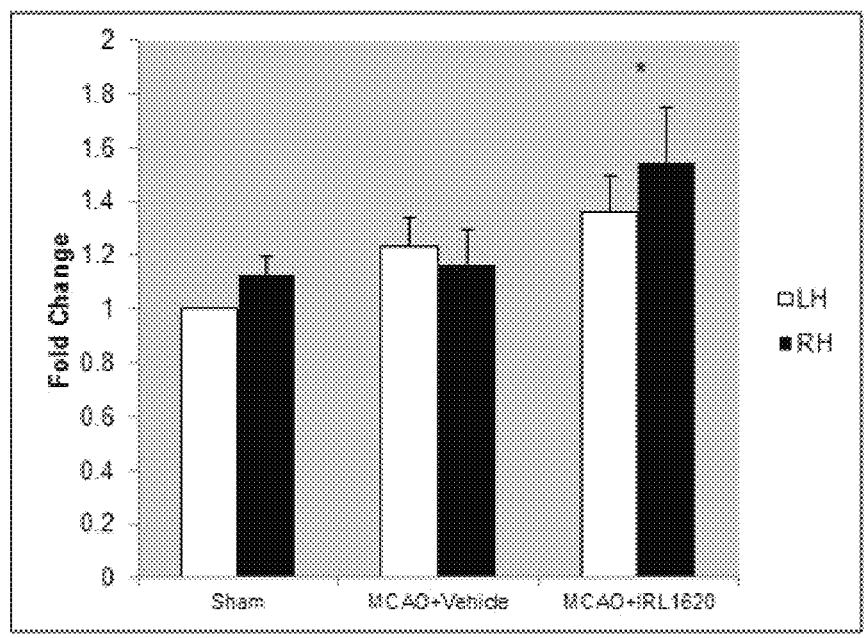
Figure 22D:
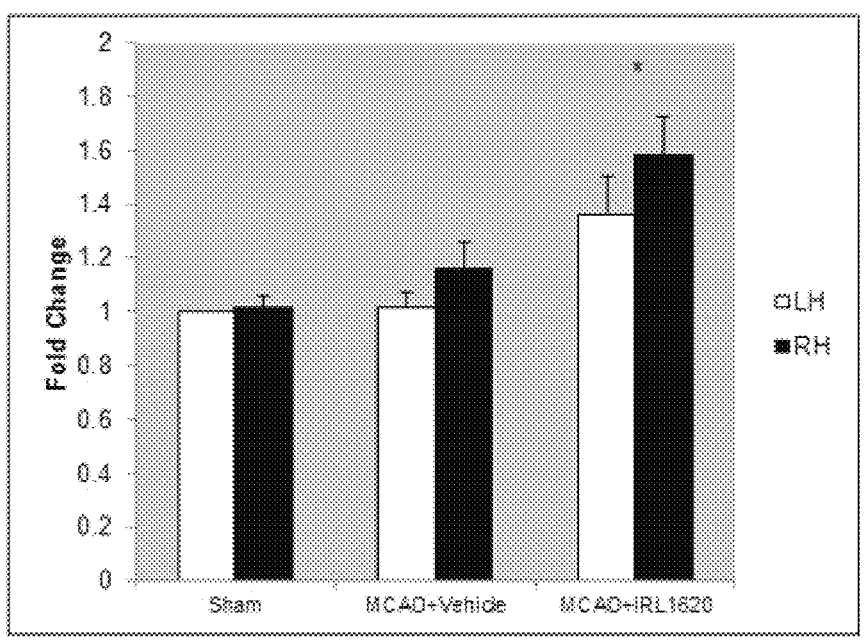

Effect of IRL-1620 on angiogenesis and neurogenesis following cerebral ischemia in rats: Angiogenesis and neurogenesis are the driving forces for the neurovascular remodeling that is essential post-stroke to restore normal brain function (Hawkins and Davis, 2005). VEGF is an endogenous protein known for its ability to promote angiogenesis and enhance vascular permeability. Under hypoxic conditions such as cerebral ischemia, VEGF expression is induced in neurons, astrocytes and endothelial cells via hypoxia-inducible factor-1 (HIF-1) (Breier and Risau, 1996). Once expressed, VEGF initiates both direct and indirect neuroprotective actions, inhibiting apoptosis, stimulating neurogenesis and angiogenesis, increasing glucose uptake and activating antioxidants (Gora-Kupilas and Josko, 2005). It has been shown that intracerebroventricular (i.c.v.) administration of an $ET_B$ receptor agonist in normal rats stimulates production of VEGF and activates VEGF receptors in the brain, while, in cultured astrocytes, this agonist increases VEGF-A mRNA as well as BrdU incorporation (Koyama et al., 2012; Koyama et al., 2011). $ET_B$ receptor agonist, IRL-1620, has been shown in our previous studies, to provide significant neuroprotection at both 24 hours and 1 week following permanent cerebral ischemia. Therefore, the neuroprotective and neurorestorative effect following stimulation of $ET_B$ receptors in cerebral ischemic rats was studied (Leonard and Gulati, 2013). At 24 hours post occlusion, it was found that IRL-1620 treatment increased $ET_B$ receptor expression and preserved neuronal numbers in the cortex, striatum and subventricular zone (SVZ) of the ischemic rat brain (FIGS. 15-22). IRL-1620 also enhanced the number of blood vessels labeled with vascular endothelial growth factor (VEGF) when compared to vehicle treatment (FIGS. 18-20). By 1 week following MCAO, VEGF-positive vessels/30 μm brain slice in the IRL-1620 group numbered 11.33±2.13 versus 4.19±0.79 in the vehicle group (P<0.01), indicating an increase in angiogenesis. Additionally, animals receiving IRL-1620 displayed an increased number of proliferating cells (P<0.0001) and cells positively staining for NGF (P<0.0001) in the infarcted brain. NGF-positive cells in the cortex, striatum and SVZ of IRL-1620 treated animals numbered 2.29±0.31, 2.08±0.26, and 3.05±0.38 per 100 $\mu m^2$, respectively, demonstrating a significant increase in neurogenesis as compared to the vehicle group, which averaged less than 1 NGF-positive cell per 100 $\mu m^2$ (FIGS. 21 and 22). Pretreatment with $ET_B$ antagonist, BQ-788, blocked the effects of IRL-1620 treatment, confirming the role of $ET_B$ receptors in the neurovascular remodeling actions of IRL-1620. Results of the present study indicate that IRL-1620, administered on the day of infarct, is neuroprotective and enhances angiogenic and neurogenic remodeling following cerebral ischemia (Leonard and Gulati, 2013).

ETB receptor agonist, IRL-1620, in the treatment of ischemic stroke: It is disclosed herein that specific ETA receptor antagonists prevent Aβ induced increase in expression of ETA receptors, oxidative stress and cognitive deficits. However, it was observed that when a combined ETA/B receptor antagonist was used, the beneficial effects were lost (Briyal et al., 2011). These findings led to the investigation of the role of ETB receptors in CNS disorders. ETB receptors are present in large number in the CNS and appear to play a key role in its development. It has been demonstrated that ETB receptors in the brain are overexpressed at the time of birth and their expression decreases with maturity of the brain (Briyal et al., 2012b). It has also been shown that damaged brain exhibits a re-emergence of childhood organizational patterns, reminiscent of an ontogenetic state and is primed for recovery. However, endogenous remodeling of the CNS is not sufficient to restore neurological function. It has been found that $ET_B$ receptor agonist, IRL-1620 [Suc-[Glu9,Ala11,15]-Endothelin-1(8-12)], can increase the expression of $ET_B$ receptors in the CNS. An increase in $ET_B$ receptors can produce reduction in apoptosis and promote angiogenesis and neurogenesis. It has been shown that expression of $ET_B$ receptors is increased in neurons, glia, and macrophages following ischemia. Additionally, studies demonstrate that $ET_B$ receptor activation enhanced proliferation of neurons and inhibit apoptosis. A regenerative response was pharmacologically activated in damaged brain by stimulating ETB receptors. ETB receptor stimulation, via selective ETB agonist, IRL-1620, significantly improved neurological deficit, motor functions, and oxidative stress markers and decreased infarct volume following ischemia in rats (Leonard et al., 2011; 2012). ETB receptor agonist, IRL-1620, provides significant neuroprotection at both 24 hours (Leonard et al., 2011) and 1 week (Leonard et al., 2012) following permanent cerebral ischemia and reduced infarct volume by 83.66% in acute study and 69.49% in chronic study. IRL-1620 treatment increased ETB receptor expression and preserved neuronal numbers in the cortex, striatum and subventricular zone (SVZ) of the ischemic rat brain. IRL-1620 also enhanced the number of blood vessels labeled with vascular endothelial growth factor (VEGF) when compared to vehicle treatment (Leonard and Gulati, 2013). Thus, IRL-1620 administered intravenously was found to be highly effective in preventing damage following stroke and aids in the neurovascular remodeling of ischemic brain by angiogenesis and neurogenesis (Leonard and Gulati, 2013). Studies further indicate that stimulation of ETB receptors by IRL-1620 provides neuroprotection (Leonard et al., 2011; 2012), and it can be used as a therapeutic agent for Alzheimer's disease (Briyal et al., 2011). It has been demonstrated that IRL-1620 prevents cognitive impairment and oxidative stress induced by Aβ (Briyal et al., 2011). It is contemplated that enhancement of possible survival mechanisms through stimulation of $ET_B$ receptors by IRL-1620 leads to a better recovery following cerebral ischemia. Most of the stroke patients show substantial neurological improvement (Dimyan and Cohen, 2011) indicating endogenous restorative mechanisms. Hence there is a potential to develop pharmacological agents that can stimulate and amplify these mechanisms. The two major approaches that can be used for the treatment of cerebral ischemia are neuroprotection, which requires an acute intervention, and neurorestoration, which can be instituted during the stroke recovery phase (Andres et al., 2011; Bacigaluppi et al., 2009; Liu et al., 2008). Several trials have been conducted or are in progress using pharmacological agents such as amphetamine, methylphenidate, levodopa, sildenafil, serotonin uptake inhibitors, erythropoietin, statins, and granulocyte colony stimulating factor but none involves stimulation of $ET_B$ receptors. It is contemplated herein that stimulation of $ET_B$ receptors produces, in various embodiments, neuroprotection, neurorestoration, or both.

REFERENCES

Ahmed T, Enam S A and Gilani AH (2010) Curcuminoids enhance memory in an amyloid-infused rat model of Alzheimer's disease. *Neuroscience* 169:1296-1306.

Andres R H, Horie N, Slikker W, Keren-Gill H, Zhan K, Sun G, Manley N C, Pereira M P, Sheikh L A, McMillan E L, Schaar B T, Svendsen C N, Bliss T M and Steinberg G K (2011) Human neural stem cells enhance structural plasticity and axonal transport in the ischaemic brain. *Brain: a journal of neurology* 134:1777-1789.

Asano T, Ikegaki I, Satoh S, Suzuki Y, Shibuya M, Sugita K and Hidaka H (1990) Endothelin: a potential modulator of cerebral vasospasm. *European journal of pharmacology* 190:365-372.

Bacigaluppi M, Pluchino S, Peruzzotti-Jametti L, Kilic E, Kilic U, Salani G, Brambilla E, West M J, Comi G, Martino G and Hermann D M (2009) Delayed post-ischaemic neuroprotection following systemic neural stem cell transplantation involves multiple mechanisms. *Brain: a journal of neurology* 132:2239-2251.

Baquer N Z, Taha A, Kumar P, McLean P, Cowsik S M, Kale R K, Singh R and Sharma D (2009) A metabolic and functional overview of brain aging linked to neurological disorders. *Biogerontology* 10:377-413.

Barone F C, Ohlstein E H, Hunter A J, Campbell C A, Hadingham S H, Parsons A A, Yang Y and Shohami E (2000) Selective antagonism of endothelin-A-receptors improves outcome in both head trauma and focal stroke in rat. *Journal of cardiovascular pharmacology* 36:S357-361.

Barone F C, White R F, Elliott J D, Feuerstein G Z and Ohlstein E H (1995) The endothelin receptor antagonist SB 217242 reduces cerebral focal ischemic brain injury. *Journal of cardiovascular pharmacology* 26 Suppl 3:S404-407.

Bath P M and Lees K R (2000) ABC of arterial and venous disease. Acute stroke. *BMJ* 320:920-923.

Bell R D and Zlokovic B V (2009) Neurovascular mechanisms and blood-brain barrier disorder in Alzheimer's disease. *Acta neuropathologica* 118:103-113.

Bredesen D E, Rao R V and Mehlen P (2006) Cell death in the nervous system. *Nature* 443:796-802.

Breier G and Risau W (1996) The role of vascular endothelial growth factor in blood vessel formation. *Trends in cell biology* 6:454-456.

Briyal S and Gulati A (2010) Endothelin-A receptor antagonist BQ123 potentiates acetaminophen induced hypothermia and reduces infarction following focal cerebral ischemia in rats. *European journal of pharmacology* 644:73-79.

Briyal S, Gulati A and Gupta Y K (2007) Effect of combination of endothelin receptor antagonist (TAK-044) and aspirin in middle cerebral artery occlusion model of acute ischemic stroke in rats. *Methods Find Exp Clin Pharmacol* 29:257-263.

Briyal S, Gulati K and Gulati A (2012a) Repeated administration of exendin-4 reduces focal cerebral ischemia-induced infarction in rats. *Brain research* 1427:23-34.

Briyal S, Lavhale M S and Gulati A (2012b) Repeated administration of centhaquin to pregnant rats did not affect postnatal development and expression of endothelin receptors in the brain, heart or kidney of pups. *Arzneimittel-Forschung* 62:670-676.

Briyal S, Philip T and Gulati A (2011) Endothelin-A receptor antagonists prevent amyloid-beta-induced increase in ETA receptor expression, oxidative stress, and cognitive impairment. *Journal of Alzheimer's disease:JAD* 23:491-503.

Carmichael S T (2006) Cellular and molecular mechanisms of neural repair after stroke: making waves. *Annals of neurology* 59:735-742.

Casadesus G, Moreira P I, Nunomura A, Siedlak S L, Bligh-Glover W, Balraj E, Petot G, Smith M A and Perry G (2007) Indices of metabolic dysfunction and oxidative stress. *Neurochemical research* 32:717-722.

Chen J, Cui X, Zacharek A, Jiang H, Roberts C, Zhang C, Lu M, Kapke A, Feldkamp C S and Chopp M (2007) Niaspan increases angiogenesis and improves functional recovery after stroke. *Annals of neurology* 62:49-58.

Chuquet J, Benchenane K, Toutain J, MacKenzie E T, Roussel S and Touzani O (2002) Selective blockade of endothelin-B receptors exacerbates ischemic brain damage in the rat. *Stroke; a journal of cerebral circulation* 33:3019-3025.

Cirrito J R, Yamada K A, Finn M B, Sloviter R S, Bales K R, May P C, Schoepp D D, Paul S M, Mennerick S and Holtzman D M (2005) Synaptic activity regulates interstitial fluid amyloid-beta levels in vivo. *Neuron* 48:913-922.

Cutler R G, Kelly J, Stone K, Pedersen W A, Tammara A, Hatanpaa K, Troncoso J C and Mattson M P (2004) Involvement of oxidative stress-induced abnormalities in ceramide and cholesterol metabolism in brain aging and Alzheimer's disease. *Proceedings of the National Academy of Sciences of the United States of America* 101:2070-2075.

de la Tone J C (1994) Impaired brain microcirculation may trigger Alzheimer's disease. *Neuroscience and biobehavioral reviews* 18:397-401.

de la Torre J C, Pappas B A, Prevot V, Emmerling M R, Mantione K, Fortin T, Watson M D and Stefano G B (2003) Hippocampal nitric oxide upregulation precedes memory loss and A beta 1-40 accumulation after chronic brain hypoperfusion in rats. *Neurological research* 25:635-641.

Deb P, Sharma S and Hassan K M (2010) Pathophysiologic mechanisms of acute ischemic stroke: An overview with emphasis on therapeutic significance beyond thrombolysis. *Pathophysiology* 17:197-218.

Dembowski C, Hofmann P, Koch T, Kamrowski-Kruck H, Riedesel H, Krammer H J, Kaup F T and Ehrenreich H (2000) Phenotype, intestinal morphology, and survival of homozygous and heterozygous endothelin B receptor-deficient (spotting lethal) rats. *J Pediatr Surg* 35:480-488.

Dimyan M A and Cohen L G (2011) Neuroplasticity in the context of motor rehabilitation after stroke. *Nature reviews Neurology* 7:76-85.

Ding G, Jiang Q, Li L, Zhang L, Zhang Z G, Ledbetter K A, Panda S, Davarani S P, Athiraman H, Li Q, Ewing J R and Chopp M (2008) Magnetic resonance imaging investigation of axonal remodeling and angiogenesis after embolic stroke in sildenafil-treated rats. *Journal of cerebral blood flow and metabolism: official journal of the International Society of Cerebral Blood Flow and Metabolism* 28:1440-1448.

Donnan G A, Fisher M, Macleod M and Davis S M (2008) Stroke. *Lancet* 371:1612-1623.

Ehrenreich H (1999) The astrocytic endothelin system: toward solving a mystery focus on "distinct pharmacological properties of ET-1 and ET-3 on astroglial gap junctions and Ca(2+) signaling". *The American journal of physiology* 277:C614-615.

Ehrenreich H, Nau T R, Dembowski C, Hasselblatt M, Barth M, Hahn A, Schilling L, Siren A L and Bruck W (2000) Endothelin b receptor deficiency is associated with an increased rate of neuronal apoptosis in the dentate gyrus. *Neuroscience* 95:993-1001.

Ehrenreich H, Oldenburg J, Hasselblatt M, Herms J, Dembowski C, Loffler B M, Bruck W, Kamrowski-Kruck H, Gall S, Siren A L and Schilling L (1999) Endothelin B receptor-deficient rats as a subtraction model to study the cerebral endothelin system. *Neuroscience* 91:1067-1075.

Ellman G L (1959) Tissue sulfhydryl groups. *Archives of biochemistry and biophysics* 82:70-77.

Ethell D W (2010) An amyloid-notch hypothesis for Alzheimer's disease. *The Neuroscientist: a review journal bringing neurobiology, neurology and psychiatry* 16:614-617.

Feigin V L, Lawes C M, Bennett D A, Barker-Collo S L and Parag V (2009) Worldwide stroke incidence and early case fatality reported in 56 population-based studies: a systematic review. *Lancet Neurol* 8:355-369.

Fisher M and Norrving B (2011) The International Agenda for Stroke, in *1st Global Conference on Healthy Lifestyles and Noncommunicable Diseases Control* (Association AH ed), American Heart Association, Moscow.

Font M A, Arboix A and Krupinski J (2010) Angiogenesis, neurogenesis and neuroplasticity in ischemic stroke. *Current cardiology reviews* 6:238-244.

Gil-Mohapel J, Boehme F, Kainer L and Christie B R (2010) Hippocampal cell loss and neurogenesis after fetal alcohol exposure: insights from different rodent models. *Brain Res Rev* 64:283-303.

Goligorsky M S, Budzikowski A S, Tsukahara H and Noiri E (1999) Co-operation between endothelin and nitric oxide in promoting endothelial cell migration and angiogenesis. *Clinical and experimental pharmacology & physiology* 26:269-271.

Gora-Kupilas K and Josko J (2005) The neuroprotective function of vascular endothelial growth factor (VEGF). *Folia neuropathologica/Association of Polish Neuropathologists and Medical Research Centre, Polish Academy of Sciences* 43:31-39.

Goto K, Kasuya Y, Matsuki N, Takuwa Y, Kurihara H, Ishikawa T, Kimura S, Yanagisawa M and Masaki T (1989) Endothelin activates the dihydropyridine-sensitive, voltage-dependent Ca2+ channel in vascular smooth muscle. *Proceedings of the National Academy of Sciences of the United States of America* 86:3915-3918.

Gulati A, Kumar A, Morrison S and Shahani B T (1997) Effect of centrally administered endothelin agonists on systemic and regional blood circulation in the rat: role of sympathetic nervous system. *Neuropeptides* 31:301-309.

Gulati A, Kumar A and Shahani B T (1996) Cardiovascular effects of centrally administered endothelin-1 and its relationship to changes in cerebral blood flow. *Life sciences* 58:437-445.

Gulati A, Rebello S, Roy S and Saxena P R (1995) Cardiovascular effects of centrally administered endothelin-1 in rats. *Journal of cardiovascular pharmacology* 26 Suppl 3:S244-246.

Gupta Y K, Briyal S, Sharma U, Jagannathan N R and Gulati A (2005) Effect of endothelin antagonist (TAK-044) on cerebral ischemic volume, oxidative stress markers and neurobehavioral parameters in the middle cerebral artery occlusion model of stroke in rats. *Life sciences* 77:15-27.

Han B H, Zhou M L, Abousaleh F, Brendza R P, Dietrich H H, Koenigsknecht-Talboo J, Cirrito J R, Milner E, Holtzman D M and Zipfel G J (2008) Cerebrovascular dysfunction in amyloid precursor protein transgenic mice: contribution of soluble and insoluble amyloid-beta peptide, partial restoration via gamma-secretase inhibition. *The Journal of neuroscience: the official journal of the Society for Neuroscience* 28:13542-13550.

Hardy J and Selkoe D J (2002) The amyloid hypothesis of Alzheimer's disease: progress and problems on the road to therapeutics. *Science* 297:353-356.

Hawkins B T and Davis T P (2005) The blood-brain barrier/neurovascular unit in health and disease. *Pharmacological reviews* 57:173-185.

Hensley K, Carney J M, Mattson M P, Aksenova M, Harris M, Wu J F, Floyd R A and Butterfield D A (1994) A model for beta-amyloid aggregation and neurotoxicity based on free radical generation by the peptide: relevance to Alzheimer disease. *Proceedings of the National Academy of Sciences of the United States of America* 91:3270-3274.

Hermann D M and Zechariah A (2009) Implications of vascular endothelial growth factor for postischemic neurovascular remodeling. *Journal of cerebral blood flow and metabolism: official journal of the International Society of Cerebral Blood Flow and Metabolism* 29:1620-1643.

Hoehn B D, Harik S I and Hudetz A G (2002) VEGF mRNA expressed in microvessels of neonatal and adult rat cerebral cortex. *Brain Res Mol Brain Res* 101:103-108.

Iadecola C, Park L and Capone C (2009) Threats to the mind: aging, amyloid, and hypertension. *Stroke; a journal of cerebral circulation* 40:S40-44.

Janson J, Laedtke T, Parisi J E, O'Brien P, Petersen R C and Butler P C (2004) Increased risk of type 2 diabetes in Alzheimer disease. *Diabetes* 53:474-481.

Johnson D K, Storandt M, Morris J C, Langford Z D and Galvin J E (2008) Cognitive profiles in dementia: Alzheimer disease vs healthy brain aging. *Neurology* 71:1783-1789.

Kakkar P, Das B and Viswanathan P N (1984) A modified spectrophotometric assay of superoxide dismutase. *Indian journal of biochemistry & biophysics* 21:130-132.

Kaundal R K, Deshpande T A, Gulati A and Sharma S S (2012) Targeting endothelin receptors for pharmacotherapy of ischemic stroke: current scenario and future perspectives. *Drug Discov Today* 17:793-804.

Kitazono T, Heistad D D and Faraci F M (1995) Enhanced responses of the basilar artery to activation of endothelin-B receptors in stroke-prone spontaneously hypertensive rats. *Hypertension* 25:490-494.

Kohzuki M, Onodera H, Yasujima M, Itoyama Y, Kanazawa M, Sato T and Abe K (1995) Endothelin receptors in ischemic rat brain and Alzheimer brain. *Journal of cardiovascular pharmacology* 26 Suppl 3:S329-331.

Kojima T, Isozaki-Fukuda Y, Takedatsu M, Hirata Y and Kobayashi Y (1992) Circulating levels of endothelin and atrial natriuretic factor during postnatal life. *Acta Paediatr* 81:676-677.

Koyama Y, Maebara Y, Hayashi M, Nagae R, Tokuyama S and Michinaga S (2012) Endothelins reciprocally regulate VEGF-A and angiopoietin-1 production in cultured rat astrocytes: implications on astrocytic proliferation. *Glia* 60:1954-1963.

Koyama Y, Nagae R, Tokuyama S and Tanaka K (2011) I.c.v administration of an endothelin ET(B) receptor agonist stimulates vascular endothelial growth factor-A production and activates vascular endothelial growth factor receptors in rat brain. *Neuroscience* 192:689-698.

Laziz I, Larbi A, Grebert D, Sautel M, Congar P, Lacroix M C, Salesse R and Meunier N (2011) Endothelin as a neuroprotective factor in the olfactory epithelium. *Neuroscience* 172:20-29.

Lee H O, Levorse J M and Shin M K (2003) The endothelin receptor-B is required for the migration of neural crest-derived melanocyte and enteric neuron precursors. *Dev Biol* 259:162-175.

Leonard M G, Briyal S and Gulati A (2011) Endothelin B receptor agonist, IRL-1620, reduces neurological damage following permanent middle cerebral artery occlusion in rats. *Brain research* 1420:48-58.

Leonard M G, Briyal S and Gulati A (2012) Endothelin B receptor agonist, IRL-1620, provides long-term neuroprotection in cerebral ischemia in rats. *Brain research* 1464:14-23.

Leonard M G and Gulati A (2009) Repeated administration of ET(B) receptor agonist, IRL-1620, produces tachyphylaxis only to its hypotensive effect. *Pharmacological research: the official journal of the Italian Pharmacological Society* 60:402-410.

Leonard M G and Gulati A (2013) Endothelin B receptor agonist, IRL-1620, enhances angiogenesis and neurogenesis following cerebral ischemia in rats. *Brain research* 1528:28-41.

Levin E R (1995) Endothelins. *The New England journal of medicine* 333:356-363.

Li L, Xiong Y, Qu Y, Mao M, Mu W, Wang H and Mu D (2008) The requirement of extracellular signal-related protein kinase pathway in the activation of hypoxia inducible factor 1 alpha in the developing rat brain after hypoxia-ischemia. *Acta neuropathologica* 115:297-303.

Liu Z, Li Y, Zhang X, Savant-Bhonsale S and Chopp M (2008) Contralesional axonal remodeling of the corticospinal system in adult rats after stroke and bone marrow stromal cell treatment. *Stroke; a journal of cerebral circulation* 39:2571-2577.

Loo L S, Ng Y K, Zhu Y Z, Lee H S and Wong P T (2002) Cortical expression of endothelin receptor subtypes A and B following middle cerebral artery occlusion in rats. *Neuroscience* 112:993-1000.

Lopes J P, Oliveira C R and Agostinho P (2010) Neurodegeneration in an Abeta-induced model of Alzheimer's disease: the role of Cdk5. *Aging cell* 9:64-77.

Lowry O H, Rosebrough N J, Farr A L and Randall R J (1951) Protein measurement with the Folin phenol reagent. *The Journal of biological chemistry* 193:265-275.

Ly J V, Zavala J A and Donnan G A (2006) Neuroprotection and thrombolysis: combination therapy in acute ischaemic stroke. *Expert Opin Pharmacother* 7:1571-1581.

Malik S, Vinukonda G, Vose L R, Diamond D, Bhimavarapu B B, Hu F, Zia M T, Hevner R, Zecevic N and Ballabh P (2013) Neurogenesis continues in the third trimester of pregnancy and is suppressed by premature birth. *The Journal of neuroscience: the official journal of the Society for Neuroscience* 33:411-423.

Mark R J, Lovell M A, Markesbery W R, Uchida K and Mattson M P (1997) A role for 4-hydroxynonenal, an aldehydic product of lipid peroxidation, in disruption of ion homeostasis and neuronal death induced by amyloid beta-peptide. *Journal of neurochemistry* 68:255-264.

Mathers C D, Boerma T and Ma Fat D (2009) Global and regional causes of death. *Br Med Bull* 92:7-32.

Meier-Ruge W, Bertoni-Freddari C and Iwangoff P (1994) Changes in brain glucose metabolism as a key to the pathogenesis of Alzheimer's disease. *Gerontology* 40:246-252.

Micieli G, Marcheselli S and Tosi P A (2009) Safety and efficacy of alteplase in the treatment of acute ischemic stroke. *Vasc Health Risk Manag* 5:397-409.

Minami M, Kimura M, Iwamoto N and Arai H (1995) Endothelin-1-like immunoreactivity in cerebral cortex of Alzheimer-type dementia. *Progress in neuro-psychopharmacology & biological psychiatry* 19:509-513.

Morris R (1984) Developments of a water-maze procedure for studying spatial learning in the rat. *Journal of neuroscience methods* 11:47-60.

Murphy T H and Corbett D (2009) Plasticity during stroke recovery: from synapse to behaviour. *Nature reviews Neuroscience* 10:861-872.

Murray I V, Liu L, Komatsu H, Uryu K, Xiao G, Lawson J A and Axelsen P H (2007) Membrane-mediated amyloidogenesis and the promotion of oxidative lipid damage by amyloid beta proteins. *The Journal of biological chemistry* 282:9335-9345.

Murray I V, Sindoni M E and Axelsen P H (2005) Promotion of oxidative lipid membrane damage by amyloid beta proteins. *Biochemistry* 44:12606-12613.

Nitta A, Itoh A, Hasegawa T and Nabeshima T (1994) beta-Amyloid protein-induced Alzheimer's disease animal model. *Neuroscience letters* 170:63-66.

Niwa K, Carlson G A and Iadecola C (2000) Exogenous A beta1-40 reproduces cerebrovascular alterations resulting from amyloid precursor protein overexpression in mice. *Journal of cerebral blood flow and metabolism: official journal of the International Society of Cerebral Blood Flow and Metabolism* 20:1659-1668.

Niwa K, Kazama K, Younkin L, Younkin S G, Carlson G A and Iadecola C (2002) Cerebrovascular autoregulation is profoundly impaired in mice overexpressing amyloid precursor protein. *American journal of physiology Heart and circulatory physiology* 283:H315-323.

Niwa K, Porter V A, Kazama K, Cornfield D, Carlson G A and Iadecola C (2001) A beta-peptides enhance vasoconstriction in cerebral circulation. *American journal of physiology Heart and circulatory physiology* 281:H2417-2424.

Nowacka M M and Obuchowicz E (2012) Vascular endothelial growth factor (VEGF) and its role in the central nervous system: a new element in the neurotrophic hypothesis of antidepressant drug action. *Neuropeptides* 46:1-10.

Nunomura A, Perry G, Aliev G, Hirai K, Takeda A, Balraj E K, Jones P K, Ghanbari H, Wataya T, Shimohama S, Chiba S, Atwood C S, Petersen R B and Smith M A (2001) Oxidative damage is the earliest event in Alzheimer disease. *Journal of neuropathology and experimental neurology* 60:759-767.

Ogunshola O O, Stewart W B, Mihalcik V, Solli T, Madri J A and Ment L R (2000) Neuronal VEGF expression correlates with angiogenesis in postnatal developing rat brain. *Brain research Developmental brain research* 119: 139-153.

Ohkawa H, Ohishi N and Yagi K (1979) Assay for lipid peroxides in animal tissues by thiobarbituric acid reaction. *Analytical biochemistry* 95:351-358.

Paris D, Quadros A, Humphrey J, Patel N, Crescentini R, Crawford F and Mullan M (2004) Nilvadipine antagonizes both Abeta vasoactivity in isolated arteries, and the reduced cerebral blood flow in APPsw transgenic mice. *Brain research* 999:53-61.

Patel T R, Galbraith S L, McAuley M A, Doherty A M, Graham D I and McCulloch J (1995) Therapeutic potential of endothelin receptor antagonists in experimental stroke. *Journal of cardiovascular pharmacology* 26 Suppl 3:S412-415.

Quinn R (2005) Comparing rat's to human's age: how old is my rat in people years? *Nutrition* 21:775-777.

Rebello S, Roy S, Saxena P R and Gulati A (1995a) Systemic hemodynamic and regional circulatory effects of centrally administered endothelin-1 are mediated through ETA receptors. *Brain research* 676:141-150.

Rebello S, Singh G and Gulati A (1995b) Elevated levels of endothelin-1 following unilateral cerebral-ischemia in rats. *Faseb Journal* 9:A937-A.

Riechers C C, Knabe W, Siren A L, Gariepy C E, Yanagisawa M and Ehrenreich H (2004) Endothelin B receptor deficient transgenic rescue rats: a rescue phenomenon in the brain. *Neuroscience* 124:719-723.

Roger V L, Go A S, Lloyd-Jones D M, Benjamin E J, Berry J D, Borden W B, Bravata D M, Dai S, Ford E S, Fox C S, Fullerton H J, Gillespie C, Hailpern S M, Heit J A, Howard V J, Kissela B M, Kittner S J, Lacidand D T, Lichtman J H, Lisabeth L D, Makuc D M, Marcus G M, Marelli A, Matchar D B, Moy C S, Mozaffarian D, Mussolino M E, Nichol G, Paynter N P, Soliman E Z, Sorlie P D, Sotoodehnia N, Turan T N, Virani S S, Wong N D, Woo D and Turner M B (2012) Heart disease and stroke statistics—2012 update: a report from the American Heart Association. *Circulation* 125:e2-e220.

Rosenstein J M, Krum J M and Ruhrberg C (2010) VEGF in the nervous system. *Organogenesis* 6:107-114.

Rubinsztein D C (2006) The roles of intracellular protein-degradation pathways in neurodegeneration. *Nature* 443: 780-786.

Schiffrin E L, Intengan H D, Thibault G and Touyz R M (1997) Clinical significance of endothelin in cardiovascular disease. *Curr Opin Cardiol* 12:354-367.

Schinelli S (2006) Pharmacology and physiopathology of the brain endothelin system: an overview. *Curr Med Chem* 13:627-638.

Schneider M P, Boesen E I and Pollock D M (2007) Contrasting actions of endothelin ET(A) and ET(B) receptors in cardiovascular disease. *Annu Rev Pharmacol Toxicol* 47:731-759.

Shin H K, Jones P B, Garcia-Alloza M, Borrelli L, Greenberg S M, Bacskai B J, Frosch M P, Hyman B T, Moskowitz M A and Ayata C (2007) Age-dependent cerebrovascular dysfunction in a transgenic mouse model of cerebral amyloid angiopathy. *Brain: a journal of neurology* 130:2310-2319.

Sims N R and Muyderman H (2009) Mitochondria, oxidative metabolism and cell death in stroke, in *Biochimica et biophysica acta* pp 80-91.

Smith C C, Stanyer L and Betteridge D J (2004) Soluble beta-amyloid (A beta) 40 causes attenuation or potentiation of noradrenaline-induced vasoconstriction in rats depending upon the concentration employed. *Neuroscience letters* 367:129-132.

Steinwachs D M, Collins-Nakai R L, Cohn L H, Garson A, Jr. and Wolk M J (2000) The future of cardiology: utilization and costs of care. *J Am Coll Cardiol* 35:91B-98B.

Strong K, Mathers C and Bonita R (2007) Preventing stroke: saving lives around the world. *Lancet Neurol* 6:182-187.

Suo Z, Humphrey J, Kundtz A, Sethi F, Placzek A, Crawford F and Mullan M (1998) Soluble Alzheimers beta-amyloid constricts the cerebral vasculature in vivo. *Neuroscience letters* 257:77-80.

Tirapelli C R, Casolari D A, Yogi A, Montezano A C, Tostes R C, Legros E, D'Orleans-Juste P and de Oliveira A M (2005) Functional characterization and expression of endothelin receptors in rat carotid artery: involvement of nitric oxide, a vasodilator prostanoid and the opening of K+ channels in ETB-induced relaxation. *British journal of pharmacology* 146:903-912.

Toda N, Ayajiki K and Okamura T (2009) Cerebral blood flow regulation by nitric oxide: recent advances. *Pharmacological reviews* 61:62-97.

Trollmann R, Schneider J, Keller S, Strasser K, Wenzel D, Rascher W, Ogunshola O O and Gassmann M (2008) HIF-1-regulated vasoactive systems are differentially involved in acute hypoxic stress responses of the developing brain of newborn mice and are not affected by levetiracetam. *Brain research* 1199:27-36.

Tsukahara H, Ende H, Magazine H I, Bahou W F and Goligorsky M S (1994) Molecular and functional characterization of the non-isopeptide-selective ETB receptor in endothelial cells. Receptor coupling to nitric oxide synthase. *The Journal of biological chemistry* 269:21778-21785.

Tsukuda K, Mogi M, Iwanami J, Min L J, Sakata A, Jing F, Iwai M and Horiuchi M (2009) Cognitive deficit in amyloid-beta-injected mice was improved by pretreatment with a low dose of telmisartan partly because of peroxisome proliferator-activated receptor-gamma activation. *Hypertension* 54:782-787.

Vidovic M, Chen M M, Lu Q Y, Kalloniatis K F, Martin B M, Tan A H, Lynch C, Croaker G D, Cass D T and Song Z M (2008) Deficiency in endothelin receptor B reduces proliferation of neuronal progenitors and increases apoptosis in postnatal rat cerebellum. *Cellular and molecular neurobiology* 28:1129-1138.

Viossat I, Duverger D, Chapelat M, Pirotzky E, Chabrier P E and Braquet P (1993) Elevated tissue endothelin content during focal cerebral ischemia in the rat. *Journal of cardiovascular pharmacology* 22 Suppl 8:S306-309.

Virgintino D, Errede M, Robertson D, Girolamo F, Masciandaro A and Bertossi M (2003) VEGF expression is developmentally regulated during human brain angiogenesis. *Histochem Cell Biol* 119:227-232.

Weller R O, Massey A, Newman T A, Hutchings M, Kuo Y M and Roher A E (1998) Cerebral amyloid angiopathy: amyloid beta accumulates in putative interstitial fluid drainage pathways in Alzheimer's disease. *The American journal of pathology* 153:725-733.

Yagami T, Ueda K, Asakura K, Kuroda T, Hata S, Sakaeda T, Kambayashi Y and Fujimoto M (2002) Effects of endothelin B receptor agonists on amyloid beta protein (25-35)-induced neuronal cell death. *Brain research* 948: 72-81.

Yagami T, Ueda K, Sakaeda T, Okamura N, Nakazato H, Kuroda T, Hata S, Sakaguchi G, Itoh N, Hashimoto Y and Fujimoto M (2005) Effects of an endothelin B receptor agonist on secretory phospholipase A2-IIA-induced apoptosis in cortical neurons. *Neuropharmacology* 48:291-300.

Yoshizawa T, Iwamoto H, Mizusawa H, Suzuki N, Matsumoto H and Kanazawa I (1992) Cerebrospinal fluid endothelin-1 in Alzheimer's disease and senile dementia of Alzheimer type. *Neuropeptides* 22:85-88.

Zhang R L, Zhang C, Zhang L, Roberts C, Lu M, Kapke A, Cui Y, Ninomiya M, Nagafuji T, Albala B, Zhang Z G and Chopp M (2008) Synergistic effect of an endothelin type A receptor antagonist, S-0139, with rtPA on the neuroprotection after embolic stroke. *Stroke; a journal of cerebral circulation* 39:2830-2836.

Zhang W W, Badonic T, Hoog A, Jiang M H, Ma K C, Nie X J and Olsson Y (1994) Astrocytes in Alzheimer's disease express immunoreactivity to the vaso-constrictor endothelin-1. *Journal of the neurological sciences* 122:90-96.

Zhang Y, Belayev L, Zhao W, Irving E A, Busto R and Ginsberg M D (2005) A selective endothelin ET(A) receptor antagonist, SB 234551, improves cerebral perfusion following permanent focal cerebral ischemia in rats. *Brain research* 1045:150-156.

Zhang Z G and Chopp M (2009) Neurorestorative therapies for stroke: underlying mechanisms and translation to the clinic. *Lancet Neurol* 8:491-500.

Zlokovic B V (2008) New therapeutic targets in the neurovascular pathway in Alzheimer's disease. *Neurotherapeutics: the journal of the American Society for Experimental Neuro Therapeutics* 5:409-414.

TABLE 1

Effect of $ET_B$ receptor agonist, IRL-1620, and antagonist, BQ788, on neurological deficit and motor function post middle cerebral artery occlusion. IRL-1620 (5 µg/kg, i.v.) or isotonic saline (1 ml/kg, i.v.) was injected at 2, 4, and 6 h post MCAO. BQ788 (1 mg/kg, i.v.) was administered 15 min prior to the first injection of IRL-1620 or vehicle. Values are expressed as mean ± SEM (n = 5-8/group). *$P < 0.05$ vs. sham. #$P < 0.05$ vs. MCAO + vehicle. @$P < 0.05$ vs. MCAO + IRL-1620.

| Treatment Groups | | Neurological Evaluation (6 point scale) | Grip Test (6 point scale) | Foot Fault Error (%) | Rota Rod Duration (sec) | Distance Traveled (cm) | Vertical Breaks |
|---|---|---|---|---|---|---|---|
| Sham | Baseline | 0 ± 0 | 4.00 ± 0.29 | 3.96 ± 0.82 | 88.89 ± 9.18 | 4968 ± 242 | 65.62 ± 3.18 |
| | Day 1 | 0 ± 0 | 4.00 ± 0.29 | 4.04 ± 1.02 | 144.89 ± 9.23 | 3325 ± 324 | 37.63 ± 3.33 |
| | Day 4 | 0 ± 0 | 3.67 ± 0.24 | 4.57 ± 0.91 | 150.67 ± 8.80 | 5323 ± 474 | 58.67 ± 1.53 |
| | Day 7 | 0 ± 0 | 4.00 ± 0.41 | 7.04 ± 2.50 | 136.67 ± 19.61 | 4306 ± 314 | 53.67 ± 12.31 |
| MCAO + Vehicle | Baseline | 0 ± 0 | 3.89 ± 0.26 | 4.56 ± 0.89 | 100.33 ± 7.54 | 5069 ± 329 | 54.56 ± 7.65 |
| | Day 1 | 3.11 ± 0.31* | 1.00 ± 0.29* | 57.64 ± 7.39* | 24.33 ± 5.87* | 764 ± 216* | 1.33 ± 0.53* |
| | Day 4 | 2.75 ± 0.57* | 1.25 ± 0.32* | 72.74 ± 6.63* | 32.50 ± 13.57* | 2353 ± 787* | 15.00 ± 7.53* |
| | Day 7 | 2.75 ± 0.57* | 1.50 ± 0.43* | 58.19 ± 10.85* | 50.00 ± 18.55 | 2366 ± 660 | 20.25 ± 7.80* |
| MCAO + IRL-1620 | Baseline | 0 ± 0 | 3.86 ± 0.46 | 4.05 ± 1.31 | 113.29 ± 8.34 | 5073 ± 334 | 61.50 ± 4.94 |
| | Day 1 | 1.29 ± 0.36# | 2.71 ± 0.52# | 18.85 ± 6.48# | 78.71 ± 22.59* | 1611 ± 325* | 12.75 ± 4.76* |
| | Day 4 | 0.67 ± 0.22# | 2.33 ± 0.58 | 14.00 ± 3.66# | 97.33 ± 2.08 | 2898 ± 451 | 26.33 ± 2.08 |
| | Day 7 | 0.67 ± 0.22# | 3.33 ± 0.22 | 8.28 ± 1.09# | 123.67 ± 7.28 | 3472 ± 732 | 34.33 ± 3.78 |
| MCAO + BQ788 | Baseline | 0 ± 0 | 3.33 ± 0.33 | 5.96 ± 1.75 | 102.00 ± 5.14 | 5141 ± 285 | 55.17 ± 3.74 |
| | Day 1 | 3.00 ± 0.58*@ | 0.67 ± 0.33*@ | 52.12 ± 11.93*@ | 37.83 ± 20.87* | 1168 ± 417* | 5.33 ± 2.47* |
| | Day 4 | 3.33 ± 0.62*@ | 0.33 ± 0.24* | 68.89 ± 12.27*@ | 37.67 ± 14.92* | 1246 ± 410* | 4.33 ± 1.52* |
| | Day 7 | 3.00 ± 0.82*@ | 1.67 ± 0.62 | 75.00 ± 17.67*@ | 49.67 ± 17.56 | 2280 ± 836 | 11.00 ± 3.97* |
| MCAO + BQ788 + IRL-1620 | Baseline | 0 ± 0 | 4.50 ± 0.34 | 4.92 ± 1.50 | 127.33 ± 16.77 | 5642 ± 358 | 48.00 ± 9.68 |
| | Day 1 | 3.00 ± 0.37*@ | 1.67 ± 0.33* | 61.01 ± 10.82*@ | 51.17 ± 19.11* | 742 ± 85* | 2.00 ± 1.48* |
| | Day 4 | 3.67 ± 0.47*@ | 1.00 ± 0.40* | 60.26 ± 14.59*@ | 62.00 ± 23.25 | 1223 ± 414 | 6.67 ± 3.42* |
| | Day 7 | 3.00 ± 0.82*@ | 1.33 ± 0.62* | 57.63 ± 17.63*@ | 54.00 ± 35.04 | 2185 ± 818 | 17.33 ± 8.56* |

What is claimed is:

1. A method of treating a patient suffering from Alzheimer's disease comprising administering to the patient a therapeutically effective amount of an endothelin-B receptor agonist, wherein the endothelin-B receptor agonist is selected from the group consisting of IRL-1620, BQ-3020, [Ala$^{1,3,11,15}$]-Endothelin, Sarafotoxin S6c, endothelin-3, and a mixture thereof.

2. The method of claim 1 wherein the endothelin-B receptor agonist is co-administered with an additional agent to treat the Alzheimer's disease.

3. The method of claim 2, wherein the additional agent is selected from the group consisting of an antidepressant, an anti-inflammatory agent, a CNS stimulant, a neuroleptic, and an anti-proliferative agent.

4. The method of claim 1 wherein the endothelin-B receptor agonist is administered at a dose of at least about 0.0002 mg/kg and less than about 0.0005 mg/kg.

5. The method of claim 1 wherein the endothelin-B receptor agonist is administered at intervals of 1 to 6 hours.

6. The method of claim 1, wherein the endothelin-B receptor agonist is IRL-1620.

7. The method of claim 6, wherein the administering comprises three doses of IRL-1620.

8. The method of claim 1, wherein the therapeutically effective amount of the endothelin-B agonist is from about 0.0001 mg/kg to about 0.5 mg/kg.

* * * * *